United States Patent
Unger et al.

(10) Patent No.: US 10,106,846 B2
(45) Date of Patent: Oct. 23, 2018

(54) OPTICAL LENS SYSTEM AND METHOD FOR MICROFLUIDIC DEVICES

(71) Applicant: Fluidigm Corporation, South San Francisco, CA (US)

(72) Inventors: Marc A. Unger, San Mateo, CA (US); Geoffrey Richard Facer, San Francisco, CA (US); Barry Clerkson, Palo Alto, CA (US); Christopher G. Cesar, Sunnyvale, CA (US); Neil Switz, Oakland, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 15/495,695

(22) Filed: Apr. 24, 2017

(65) Prior Publication Data
US 2017/0321249 A1 Nov. 9, 2017

Related U.S. Application Data

(60) Continuation of application No. 14/960,754, filed on Dec. 7, 2015, now Pat. No. 9,663,821, which is a
(Continued)

(51) Int. Cl.
  *G01N 21/00* (2006.01)
  *G01N 15/06* (2006.01)
  (Continued)

(52) U.S. Cl.
  CPC .............. *C12Q 1/686* (2013.01); *G01N 21/64* (2013.01); *G01N 21/6452* (2013.01);
  (Continued)

(58) Field of Classification Search
  CPC .............. G01N 21/8483; G01N 21/16; G01N 27/44721; G01N 21/6486; G01N 21/6456;
  (Continued)

(56) References Cited

U.S. PATENT DOCUMENTS

| 4,155,862 A | 5/1979 | Mohn et al. |
| 4,540,534 A | 9/1985 | Grendol |

(Continued)

FOREIGN PATENT DOCUMENTS

| CN | 1323393 A | 11/2001 |
| CN | 2575662 Y | 9/2003 |

(Continued)

OTHER PUBLICATIONS

ABI Prism 7000 Sequence Detection System User Guide, Applied Biosystems, 2001, 256 pages.
(Continued)

*Primary Examiner* — William Choi

(74) *Attorney, Agent, or Firm* — Kilpatrick Townsend & Stockton LLP

(57) ABSTRACT

An apparatus for imaging one or more selected fluorescence indications from a microfluidic device. The apparatus includes an imaging path coupled to least one chamber in at least one microfluidic device. The imaging path provides for transmission of one or more fluorescent emission signals derived from one or more samples in the at least one chamber of the at least one microfluidic device. The chamber has a chamber size, the chamber size being characterized by an actual spatial dimension normal to the imaging path. The apparatus also includes an optical lens system coupled to the imaging path. The optical lens system is adapted to transmit the one or more fluorescent signals associated with the chamber.

20 Claims, 30 Drawing Sheets

Related U.S. Application Data continuation of application No. 14/547,442, filed on Nov. 19, 2014, now Pat. No. 9,234,237, which is a continuation of application No. 13/937,340, filed on Jul. 9, 2013, now Pat. No. 8,926,905, which is a continuation of application No. 13/253,703, filed on Oct. 5, 2011, now Pat. No. 8,512,640, which is a continuation of application No. 12/862,621, filed on Aug. 24, 2010, now Pat. No. 8,048,378, which is a continuation of application No. 12/538,641, filed on Aug. 10, 2009, now Pat. No. 7,906,072, which is a division of application No. 11/953,538, filed on Dec. 10, 2007, now Pat. No. 7,588,672, which is a continuation of application No. 11/148,157, filed on Jun. 7, 2005, now Pat. No. 7,307,802.

(60) Provisional application No. 60/578,106, filed on Jun. 7, 2004.

(51) Int. Cl.
| | |
|---|---|
| *C12Q 1/686* | (2018.01) |
| *G02B 21/36* | (2006.01) |
| *G01N 21/75* | (2006.01) |
| *G01N 21/64* | (2006.01) |
| *G01N 21/84* | (2006.01) |
| *G02B 21/16* | (2006.01) |
| *G01N 27/447* | (2006.01) |
| *B01L 7/00* | (2006.01) |
| *B01L 3/00* | (2006.01) |

(52) U.S. Cl.
CPC ..... *G01N 21/6456* (2013.01); *G01N 21/6486* (2013.01); *G01N 21/75* (2013.01); *G01N 21/8483* (2013.01); *G01N 27/44721* (2013.01); *G02B 21/16* (2013.01); *G02B 21/36* (2013.01); *B01J 2219/00576* (2013.01); *B01J 2219/00704* (2013.01); *B01L 3/5027* (2013.01); *B01L 7/52* (2013.01); *G01N 2021/6421* (2013.01); *G01N 2201/061* (2013.01)

(58) Field of Classification Search
CPC . G01N 2021/6421; B01L 7/52; B01L 3/5027; B01J 2219/00704; B01J 2219/00576; G02B 21/16
USPC ................. 422/68.1; 204/602, 603
See application file for complete search history.

(56) References Cited

U.S. PATENT DOCUMENTS

| | | |
|---|---|---|
| 4,580,895 A | 4/1986 | Patel |
| 4,626,684 A | 12/1986 | Landa |
| 4,628,026 A | 12/1986 | Gardell et al. |
| 4,629,862 A | 12/1986 | Kitagawa et al. |
| 4,683,202 A | 7/1987 | Mullis |
| 4,774,055 A | 9/1988 | Wakatake et al. |
| 4,778,763 A | 10/1988 | Makiguchi et al. |
| 4,798,428 A | 1/1989 | Karim et al. |
| 4,889,818 A | 12/1989 | Gelfand et al. |
| 5,038,852 A | 8/1991 | Johnson et al. |
| 5,096,807 A | 3/1992 | Leaback |
| 5,121,256 A | 6/1992 | Corle et al. |
| 5,171,995 A | 12/1992 | Gast et al. |
| 5,210,015 A | 5/1993 | Gelfand et al. |
| 5,255,976 A | 10/1993 | Connelly |
| 5,290,513 A | 3/1994 | Berthold et al. |
| 5,314,825 A | 5/1994 | Weyrauch et al. |
| 5,317,452 A | 5/1994 | Prentiss et al. |
| 5,324,635 A | 6/1994 | Kawase et al. |
| 5,340,747 A | 8/1994 | Eden |
| 5,355,215 A | 10/1994 | Schroeder et al. |
| 5,376,252 A | 12/1994 | Ekstrom et al. |
| 5,383,023 A | 1/1995 | Walleczek |
| 5,415,839 A | 5/1995 | Zaun et al. |
| 5,436,134 A | 7/1995 | Haugland et al. |
| 5,436,718 A | 7/1995 | Fernandes et al. |
| 5,463,564 A | 10/1995 | Agrafiotis et al. |
| 5,487,972 A | 1/1996 | Gelfand et al. |
| 5,496,519 A | 3/1996 | Schacher |
| 5,525,300 A | 6/1996 | Danssaert et al. |
| 5,538,848 A | 7/1996 | Livak et al. |
| 5,557,398 A | 9/1996 | Wechsler et al. |
| 5,583,351 A | 12/1996 | Brown et al. |
| 5,585,277 A | 12/1996 | Bowie et al. |
| 5,589,351 A | 12/1996 | Harootunian |
| 5,599,504 A | 2/1997 | Hosoi et al. |
| 5,631,734 A | 5/1997 | Stern et al. |
| 5,658,751 A | 8/1997 | Yue et al. |
| 5,679,582 A | 10/1997 | Bowie et al. |
| 5,710,028 A | 1/1998 | Eyal et al. |
| 5,723,591 A | 3/1998 | Livak et al. |
| 5,729,393 A | 3/1998 | Lee et al. |
| 5,748,365 A | 5/1998 | Chen |
| 5,764,613 A | 6/1998 | Yamamoto et al. |
| 5,776,191 A | 7/1998 | Mazzocco |
| 5,804,375 A | 9/1998 | Gelfand et al. |
| 5,815,306 A | 9/1998 | Sheridon et al. |
| 5,842,787 A | 12/1998 | Kopf-Sill et al. |
| 5,846,710 A | 12/1998 | Bajaj |
| 5,856,092 A | 1/1999 | Dale et al. |
| 5,888,819 A | 3/1999 | Goelet et al. |
| 5,932,799 A | 8/1999 | Moles |
| 5,939,709 A | 8/1999 | Ghislain et al. |
| 5,945,283 A | 8/1999 | Kwok et al. |
| 5,994,056 A | 11/1999 | Higuchi |
| 5,995,280 A | 11/1999 | Beach |
| 6,004,744 A | 12/1999 | Goelet et al. |
| 6,020,141 A | 2/2000 | Pantoliano et al. |
| 6,030,787 A | 2/2000 | Livak et al. |
| 6,036,920 A | 3/2000 | Pantoliano et al. |
| 6,046,056 A | 4/2000 | Parce et al. |
| 6,100,541 A | 8/2000 | Nagle et al. |
| 6,133,576 A | 10/2000 | Shafer et al. |
| 6,177,990 B1 | 1/2001 | Kain et al. |
| 6,181,478 B1 | 1/2001 | Mandella |
| 6,200,737 B1 | 3/2001 | Walt et al. |
| 6,214,293 B1 | 4/2001 | Pantoliano et al. |
| 6,236,513 B1 | 5/2001 | Mallary |
| 6,268,218 B1 | 7/2001 | Pantoliano et al. |
| 6,270,696 B1 | 8/2001 | Jain et al. |
| 6,277,545 B1 | 8/2001 | Iida et al. |
| 6,298,026 B1 | 10/2001 | Suzuki et al. |
| 6,301,055 B1 | 10/2001 | Legrand et al. |
| 6,307,689 B1 | 10/2001 | Ichimura et al. |
| 6,316,781 B1 | 11/2001 | Nagle et al. |
| 6,353,475 B1 | 3/2002 | Jensen et al. |
| 6,369,957 B1 | 4/2002 | Ishida |
| 6,408,878 B2 | 6/2002 | Unger et al. |
| 6,503,831 B2 | 1/2003 | Speakman |
| 6,540,895 B1 | 4/2003 | Spence et al. |
| 6,548,171 B1 | 4/2003 | Barbera-Guillem et al. |
| 6,560,030 B2 | 5/2003 | Legrand et al. |
| 6,608,726 B2 | 8/2003 | Legrand et al. |
| 6,614,598 B1 | 9/2003 | Quake et al. |
| 6,706,471 B1 | 3/2004 | Brow et al. |
| 6,713,389 B2 | 3/2004 | Speakman |
| 6,742,661 B1 | 6/2004 | Schulte et al. |
| 6,767,706 B2 | 7/2004 | Quake et al. |
| 6,781,690 B2 | 8/2004 | Armstrong et al. |
| 6,818,395 B1 | 11/2004 | Quake et al. |
| 6,836,384 B2 | 12/2004 | Legrand et al. |
| 6,875,619 B2 | 4/2005 | Blackburn |
| 6,885,982 B2 | 4/2005 | Harris et al. |
| 6,911,345 B2 | 6/2005 | Quake et al. |
| 6,929,030 B2 | 8/2005 | Unger et al. |
| 6,951,632 B2 | 10/2005 | Unger et al. |
| 6,960,437 B2 | 11/2005 | Enzelberger et al. |
| 7,023,007 B2 | 4/2006 | Gallagher |

(56) References Cited

U.S. PATENT DOCUMENTS

| | | |
|---|---|---|
| 7,042,649 B2 | 5/2006 | Quake et al. |
| 7,052,545 B2 | 5/2006 | Quake et al. |
| 7,059,348 B2 | 6/2006 | Nat |
| 7,062,418 B2 | 6/2006 | Lee et al. |
| 7,078,663 B2 | 7/2006 | Takamizawa |
| 7,097,809 B2 | 8/2006 | Van Dam et al. |
| 7,143,785 B2 | 12/2006 | Maerkl et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef et al. |
| 7,291,512 B2 | 11/2007 | Unger |
| 7,294,503 B2 | 11/2007 | Quake et al. |
| 7,307,802 B2 | 12/2007 | Unger |
| 7,351,376 B1 | 4/2008 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,583,853 B2 | 9/2009 | Taylor et al. |
| 7,588,672 B2 | 9/2009 | Unger et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,695,683 B2 | 4/2010 | Quan et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 7,906,072 B2 | 3/2011 | Unger et al. |
| 8,048,378 B2 | 11/2011 | Unger et al. |
| 8,512,640 B2 | 8/2013 | Unger et al. |
| 8,721,968 B2 | 5/2014 | Unger et al. |
| 8,926,905 B2 | 1/2015 | Unger et al. |
| 9,234,237 B2 | 1/2016 | Unger et al. |
| 9,663,821 B2 | 5/2017 | Unger et al. |
| 2002/0034027 A1 | 3/2002 | Legrand et al. |
| 2002/0037499 A1 | 3/2002 | Quake et al. |
| 2002/0139936 A1 | 10/2002 | Dumas |
| 2002/0145231 A1 | 10/2002 | Quake et al. |
| 2002/0159162 A1 | 10/2002 | Ramm et al. |
| 2003/0008308 A1 | 1/2003 | Enzelberger et al. |
| 2003/0032204 A1 | 2/2003 | Walt et al. |
| 2003/0076649 A1 | 4/2003 | Speakman |
| 2003/0096310 A1 | 5/2003 | Hansen et al. |
| 2003/0134129 A1 | 7/2003 | Lammertink et al. |
| 2003/0138829 A1 | 7/2003 | Unger et al. |
| 2003/0138941 A1 | 7/2003 | Gong et al. |
| 2003/0203497 A1 | 10/2003 | Pantoliano et al. |
| 2003/0219754 A1 | 11/2003 | Oleksy et al. |
| 2004/0027707 A1 | 2/2004 | Legrand et al. |
| 2004/0072278 A1 | 4/2004 | Chou et al. |
| 2004/0096960 A1 | 5/2004 | Burd Mehta et al. |
| 2004/0112442 A1 | 6/2004 | Maerkl et al. |
| 2004/0115731 A1 | 6/2004 | Hansen et al. |
| 2004/0178370 A1 | 9/2004 | Oldham et al. |
| 2004/0180377 A1 | 9/2004 | Manger et al. |
| 2004/0185504 A1 | 9/2004 | Pantoliano et al. |
| 2004/0224380 A1 | 11/2004 | Chou et al. |
| 2004/0248167 A1 | 12/2004 | Quake et al. |
| 2005/0019792 A1 | 1/2005 | McBride et al. |
| 2005/0036222 A1 | 2/2005 | Legrand et al. |
| 2005/0048540 A1 | 3/2005 | Inami et al. |
| 2005/0052754 A1 | 3/2005 | Quake et al. |
| 2005/0053952 A1 | 3/2005 | Hong et al. |
| 2005/0084421 A1 | 4/2005 | Unger et al. |
| 2005/0129581 A1 | 6/2005 | McBride et al. |
| 2005/0142033 A1 | 6/2005 | Glezer et al. |
| 2005/0145496 A1 | 7/2005 | Goodsaid et al. |
| 2005/0164376 A1 | 7/2005 | Balagadde et al. |
| 2005/0196785 A1 | 9/2005 | Quake et al. |
| 2005/0201901 A1 | 9/2005 | Grossman et al. |
| 2005/0214173 A1 | 9/2005 | Facer et al. |
| 2005/0221373 A1 | 10/2005 | Enzelberger et al. |
| 2005/0233335 A1 | 10/2005 | Wittwer et al. |
| 2005/0252773 A1 | 11/2005 | McBride et al. |
| 2006/0006067 A1 | 1/2006 | Unger |
| 2006/0019253 A1 | 1/2006 | Wittwer et al. |
| 2006/0172408 A1 | 8/2006 | Quake et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0088952 A1 | 4/2008 | Unger et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2009/0294703 A1 | 12/2009 | Unger et al. |
| 2009/0317798 A1 | 12/2009 | Heid et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2012/0035080 A1 | 2/2012 | Unger et al. |
| 2012/0264226 A1 | 10/2012 | Unger et al. |
| 2014/0011204 A1 | 1/2014 | Unger et al. |
| 2014/0024559 A1 | 1/2014 | Unger et al. |

FOREIGN PATENT DOCUMENTS

| | | |
|---|---|---|
| CN | ZL200580025595.5 | 1/2010 |
| CN | 101793826 A | 8/2010 |
| CN | 102680440 A | 9/2012 |
| CN | 103884698 A | 6/2014 |
| EP | 0 266 881 A2 | 5/1988 |
| EP | 0 362 993 A2 | 4/1990 |
| EP | 0 512 334 A2 | 11/1992 |
| EP | 0 329 822 B1 | 6/1994 |
| EP | 0 310 229 B1 | 3/1996 |
| EP | 0 640 828 B1 | 5/2000 |
| EP | 2 701 194 A2 | 2/2014 |
| EP | 2 752 874 A1 | 7/2014 |
| HK | 1107183 | 9/2010 |
| JP | 60-156521 | 8/1985 |
| JP | 61-215948 A | 9/1986 |
| JP | 62-105031 A | 5/1987 |
| JP | 3-25598 | 2/1991 |
| JP | 03-122552 A | 5/1991 |
| JP | 03-259099 A | 11/1991 |

(56) References Cited

FOREIGN PATENT DOCUMENTS

| JP | 04-027399 A | 1/1992 |
|---|---|---|
| JP | 04-084751 A | 3/1992 |
| JP | 7-36118 | 2/1995 |
| JP | 09-243813 A | 9/1997 |
| JP | 2000-258340 | 9/2000 |
| JP | 2003-536058 A | 6/2001 |
| JP | 2003-84210 | 3/2003 |
| JP | 4911722 | 1/2012 |
| JP | 2012-53070 | 3/2012 |
| JP | 2012-058260 | 3/2012 |
| WO | 87/06270 A1 | 10/1987 |
| WO | 89/09835 A1 | 10/1989 |
| WO | 91/09950 A1 | 7/1991 |
| WO | 92/03556 A1 | 3/1992 |
| WO | 92/05278 A2 | 4/1992 |
| WO | 92/16657 A1 | 10/1992 |
| WO | 94/05394 | 3/1994 |
| WO | 97/22719 A1 | 6/1997 |
| WO | 98/15969 A2 | 4/1998 |
| WO | 98/19854 A1 | 5/1998 |
| WO | 01/01025 A2 | 1/2001 |
| WO | 01/04617 A1 | 1/2001 |
| WO | 2001/067369 A2 | 9/2001 |
| WO | 01/94635 A2 | 12/2001 |
| WO | 02/14058 A2 | 2/2002 |
| WO | 02/30486 A2 | 4/2002 |
| WO | 02/43615 A2 | 6/2002 |
| WO | 02/43937 A2 | 6/2002 |
| WO | 02/081729 A2 | 10/2002 |
| WO | 2004/015133 A2 | 2/2004 |
| WO | 2004/028955 A2 | 4/2004 |
| WO | 2004/089810 A2 | 10/2004 |
| WO | 2004/104228 A1 | 12/2004 |
| WO | 2005/069980 A2 | 8/2005 |
| WO | 2005/107938 A2 | 11/2005 |
| WO | 2005/121864 A2 | 12/2005 |
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |
| WO | 2011/053790 A2 | 5/2011 |

OTHER PUBLICATIONS

Berg, "*Dynamic Properties of Bacterial Flagellar Motors*", Nature. May 3, 1974;249(452):77-79.
Berry et al., "*Absence of a barrier to Backwards Rotation of the Bacterial Flagellar Motor Demonstrated With Optical Tweezers*", Proc. Natl. Acad. Sci. USA., Dec. 1997; 94:14433-14437.
Brody et al., "*A Self-Assembled Microlensing Rotational Probe*", Applied Physics Letters,. , Jan. 4, 1999; 74(1):144-146.
Chavan et al., "*Interaction of Nucleotides with Acidic Fibroblast Growth Factor (FGF-1)*", Biochemistry, vol. 33, No. 23, 1994, pp. 7193-7202.
Chou et al., "*Prevention of pre-PCR mispriming and primer dimerization improves low-copy-number amplifications*", Nucleic Acids Research, vol. 20, No. 7, pp. 1717-1723, 1992.
Eftink, M.R. "*The Use of Fluorescence Methods to Monitor Unfolding Transitions in Proteins*" Biophysical Journal, vol. 66, Feb. 1994, pp. 482-501.
Elson, "*Fluorescence Correlation Spectroscopy and Photobleaching Recovery*", Ann. Rev. Phys. Chem., 1985; 36:379-406.
European Search Report for corresponding European Patent Application No. 13194084.3 dated Jun. 12, 2014, 6 pages.
European Search Report for corresponding European Patent Application No. 13194088.4 dated Jun. 12, 2014 , 11 pages.
Finer et al., "*Single Myosin Molecule Mechanics: Piconewton Forces and Nanometre Steps*", Nature 1994; 368( 6467):113-119.

Freire, "*Methods in Enzymology*", vol. 259: Energetics of Biological Macromolecules, ed. Johnson, M.L. and G.K Ackers, pp. 144-168, (1995).
Guatelli et al., "*Isothermal, in vitro amplification of nucleic acids by a multienzyme reaction modeled after retro viral replication*", Proc. Natl. Acad. Sci. USA, 1990; 87:1874-1878.
Guatelli et al., "*Isothermal, in vitro amplification of nucleic acids by a multienzyme reaction modeled after retro viral replication*", Proc. Natl. Acad. Sci. USA, vol. 87, pp. 1874-1878, 1990.
Haff et al., "*A High-Performance System for Automation of the Polymerase Chain Reaciton*", BioTechniques: The Journal of Laboratory Technology for Bio-research, vol. 10, No. 1, Jan. 1991.
Higuchi et al., "*Kinetic PCR Analysis: Real-time Monitoring of DNA Amplification Reactions,*" Bio/Technology, vol. 11, Sep. 1993, pp. 1026-1030.
Higuchi et al., "*Simultaneous Amplification and Detection of Specific DNA Sequences*", Bio/Technology, vol. 10, pp. 413-417, Apr. 1992.
Hong et al., "*A Nanoliter-Scale Nucleic Acid Processor with Parallel Architecture*", Nat Biotechnol. Apr. 2004;22(4):435-9. Epub Mar. 14, 2004.
Innis et al. eds, "*PCR Protocols a Guide to Methods and Applications*", Academic Press, Inc., 1990, 8 pages.
Jameson et al., "*Chapter 4: Time-Resolved Fluorescence in Biology and Biochemistry*", Biophysical and Biochemical Aspects of Fluorescence Spectroscopy; Plenum Press, pp. 2 cover pages and 105-133, 1991.
Kinosita Jr. et al., "*F1-ATPase: A Rotary Motor Made of a Single Molecule*", Cell, Apr. 3; vol. 93: 21-24.
Kwoh et al., "*Transcription-based amplification system and detection of amplified human immunodeficiency virus type 1 with a bead-based sandwich hybridization format*", Proc. Natl. Acad. Sci. USA 1989; 86:1173-1177.
Landergen et al., "*A ligase-mediated gene detection technique*", Science 1988; 241(4869):1077-1080.
Liu et al., "*Solving the World-to-Chip Interface Problem with a Microfluidic Matrix*", Analytical Chemistry, American Chemical Society, United States, vol. 75, No. 18, Sep. 15, 2003, pp. 4718-4723.
Lizardi et al., "*Exponential Amplification of Recombinant-RNA Hybridization Probes*", Bio/Technology, vol. 6, pp. 1197-1202, 1988.
Mervis et al., "*Aligning and Attaching a Lens to an Optical Fiber Using Light Pressure Force*", Opt Lett. Mar. 1, 1993;18(5):325-327.
Míguez, et al., "*Photonic Crystal Properties of Packed Submicrometric SiO2 Spheres*", Appl. Phys. Lett., Applied Physics Letters, Sep. 1, 1997; 71( 9):1148-1150.
Morton et al., "*Energetic Origins of Specificity of Ligand Binding in a Interior Nopolar Cavity of T4 Lysozmye,*" Biochemistry. vol. 34, No. 27, 1995, p. 8564-8575.
Neri et al., "*Transferring automation for large-scale development and production of Invader SNP assays*", Proceedings—SPIE The International Society for Optical Engineering, 2000; 3826:117-125.
Perkins et al., "*Relaxation of a Single DNA Molecule Observed by Optical Microscopy*", Science, May 6, 1994; 264:822-826.
Piatek et al., "*Molecular beacon sequence analysis for detecting drug resistance in Mycobacterium tuberculosis*", Nat. Biotechnol. 1998; 16:359-363.
Pilch et al., "*Ligand-induced formation of nucleic acid triple helices,*" Proceedings of the National Acadmey of Sciences USA, vol. 91, Sep. 1994, pp. 9332-9336.
Qinghui et al., "*An Integrated Software Solution for Real-Time PCR Analysis Based on Microfluidic Biochip*", Proceeding SPIE, vol. 5119, Apr. 2003, pp. 77-86, 11 pages.
Ramm, "*Imaging Systems in Assay Screening*", Drug Discovery Today, vol. 4, No. 9, Sep. 1, 1999, pp. 401-410.
Ramsay et al., "*A Multidimensional Spectrophotometer for Monitoring Thermal Unfolding Transitions of Macromolecules*", Biophysical Journal, vol. 31, Feb. 1994, pp. 9332-9336.
Shingyoji et al., "*Dynein Arms Are Oscillating Force Generators*", Nature, Jun. 18, 1998; 393, pp. 711-714.
Silverman et al., "*Flagellar Rotation and the Mechanism of Bacterial Motility*", Nature, May 3, 1974; 249:73-74.

(56) References Cited

OTHER PUBLICATIONS

Smith et al., "*Inexpensive Optical Tweezers for Undergraduate Laboratories*", Am. J. Phys., Jan. 1999; 67(1):26-35, Jan. 1999.

Solinas et al., "*Duplex Scorpion primers in SNP analysis and FRET applications*", Nucleic Acids Research, 2001; 29(20):20 e96.

Sooknanan et al., "*NASBA: a detection and amplification system uniquely suited for RNA*", BioTechnology, Jun. 1995; 13: 563-565.

Svoboda et al., "*Direct Observation of Kinesin Stepping by Optical Trapping Interferometry*", Nature, Oct. 21, 1993; 365:721-727.

Thelwell et al., "*Mode of action and application of Scorpion primers to mutation detection*", Nucleic Acids Research, 2000; 28:3752-3761.

Fluidigm, Thermo Fisher Scientific Claim Chart for ABI Prism 7000 User Manual dated Feb. 27, 2014, 12 pages.

Fluidigm, Thermo Fisher Scientific Claim Chart for European Patent No. 640 828 dated Feb. 27, 2014, 10 pages.

Thorsen et al., "*Microfluidic Large-Scale Integration*", Science. Oct. 18, 2002;298(5593):580-4. Epub Sep. 26, 2002.

Tsai et al., "*Formulation Design of Acidic Fibroblast Growth Factor*", Pharmaceutical Research, vol. 10, No. 5, May 1993, pp. 649-659.

Tyagi et al, "*Molecular Beacons: Probes that Fluoresce upon Hybridization*", Nat. Biotechnology, 1996; 14:303-308.

Tyagi, et al., "*Multicolor Molecular Beacons for Allele Discrimination*", Nat. Biotechnol. 1998; 16:49-53.

Unger, "*Monolithic Microfabricated Valves and Pumps by Multilayer Soft Lithography*", Science. Apr. 7, 2000;288(5463):113-6.

Van Brunt, "*Amplifying Genes: PCR and its Alternatives*", Bio/Technology, vol. 8, pp. 291-294, Apr. 1990.

Volkin et al., "*Physical Stabilization of Acidic Fibroblast Growth Factor by Polyanions*", Archives of Biochemistry and Biophysics, vol. 300, No. 1, pp. 30-41, (Jan. 1993).

Volkin et al., "*The Effect of Polyanions of the Stabilization of Acidic Fibroblast Growth Factor*", Harnessing Biotechnology for the 21th Century, ed. Ladisch, M. and A Bose, pp. 298-302, (1992).

Waring, "*Stabilization of Two-Stranded Robohomopolymer Helices and Destabilization of a Three-Stranded Helix by Ethidium Bromide*", The Biochemical Journal, vol. 143, 1974, pp. 483-486.

Waring, "*Stereochemical aspects of the interactions between steroidal diamines and DNA*", Nucleic Acids Research, vol. 2, No. 4, Apr. 1975, pp. 567-585.

Weber et al., "*Structure-Based Design of Synthetic Azobenzene Ligands for Streptavidin*", Journal of the American Chemical Society, vol. 116, No. 7, 1994, pp. 2717-2724.

Wu et al., "*The ligation amplification reaction (LAR)—amplification of specific DNA sequences using sequential rounds of template-dependent ligation*", Genomics 1989; 4(4):560-569.

Zhu et al., "*High-Sensitivity Capillary Electrophoresis of Double-Stranded DNA Fragments Using Monomeric and Dimeric Fluorescent Intercalating Dyes*", Anal. Chem. 1994; 66:1941-1948.

Summons to Attend Oral Proceedings Pursuant to Rule 115(1) EPC received in European Patent Application No. 13194084.3, dated Oct. 13, 2017. 7 pages.

Brief Communication re Oral Proceedings received in European Patent Application No. 13194084.3, dated Feb. 20, 2018. 2 pages.

Communication Under Rule 71(3) EPC received in European Patent Application No. 13194084.3, dated Mar. 20, 2018. 7 pages.

OPTICAL LENS SYSTEM AND METHOD FOR MICROFLUIDIC DEVICES

CROSS-REFERENCES TO RELATED APPLICATIONS

The present application is a continuation of U.S. Ser. No. 14/960,754 filed Dec. 7, 2015, which is a continuation of U.S. Ser. No. 14/547,442 filed Nov. 19, 2014 (now U.S. Pat. No. 9,234,237), which is a continuation of U.S. Ser. No. 13/937,340 filed Jul. 9, 2013 (now U.S. Pat. No. 8,926,905), which is a continuation of U.S. Ser. No. 13/253,703 filed Oct. 5, 2011 (now U.S. Pat. No. 8,512,640), which is a continuation of U.S. Ser. No. 12/862,621 filed Aug. 24, 2010 (now U.S. Pat. No. 8,048,378), which is a continuation of U.S. Ser. No. 12/538,641 filed Aug. 10, 2009 (now U.S. Pat. No. 7,906,072), which is a division of U.S. Ser. No. 11/953,538 filed Dec. 10, 2007 (now U.S. Pat. No. 7,588,672), which is a continuation of U.S. Ser. No. 11/148,157 filed Jun. 7, 2005 (now U.S. Pat. No. 7,307,802), which claims priority to U.S. Provisional Application No. 60/578,106 filed Jun. 7, 2004—the disclosures of which are all incorporated herein by reference in their entirety for all purposes.

BACKGROUND OF THE INVENTION

The present invention relates generally to microfluidic techniques. In particular, the invention provides a method and system for imaging one or more entities in a chamber of a microfluidic device (e.g., suspended in a volume of fluid). More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

Concerted efforts to develop and manufacture microfluidic systems to perform various chemical and biochemical analyses and syntheses have occurred. Such systems have been developed for preparative and analytical applications. A goal to make such micro-sized devices arises from significant benefits achieved from miniaturization of conventional macro scale analyses and syntheses, which are often cumbersome and less efficient. A substantial reduction in time, lower costs, and more efficient space allocation are achieved as benefits using these microfluidic systems. Additional benefits may include a reduction in human operator involvement with automated systems using these microfluidic devices. Automated systems also decrease operator errors and other operator type limitations. Microfluidic devices have been proposed for use in a variety of applications, including, for instance, capillary electrophoresis, gas chromatography and cell separations.

Microfluidic devices adapted to conduct nucleic acid amplification processes are potentially useful in a wide variety of applications. For example, such devices could be used to determine the presence or absence of a particular target nucleic acid in a sample, as an analytical tool. Examples of utilizing microfluidic device as an analytical tool include:

testing for the presence of particular pathogens (e.g., viruses, bacteria or fungi);
  identification processes (e.g., paternity and forensic applications);
  detecting and characterizing specific nucleic acids associated with particular diseases or genetic disorders;
  detecting gene expression profiles/sequences associated with particular drug behavior (e.g. for pharmacogenetics, i.e. choosing drugs which are compatible/especially efficacious for/not hazardous with specific genetic profiles); and
  conducting genotyping analyses and gene expression analyses (e.g., differential gene expression studies).

Alternatively, the devices can be used in a preparative fashion to amplify nucleic acids, producing an amplified product at sufficient levels needed for further analysis. Examples of these analysis processes include sequencing of the amplified product, cell-typing, DNA fingerprinting, and the like. Amplified products can also be used in various genetic engineering applications. These genetic engineering applications include (but are not limited to) the production of a desired protein product, accomplished by insertion of the amplified product into a vector that is then used to transform cells into the desired protein product.

Despite these potential applications, imaging systems (also referred to as readers) adapted to collect and process imaging data, for example, fluorescence data, from such microfluidic devices have various shortcomings. Some conventional readers operate in a scanning mode, in which a laser beam is raster scanned over the microfluidic device. In other such systems, the device or both the laser and the device are translated. These scanners collect fluorescence data from the reaction chambers present in the microfluidic device in a sequential manner associated with the raster scanning of the laser source/device. Other conventional scanners operate in a stitching mode, sequentially imaging small areas, for example, areas less than 1 mm$^2$ in size, and stitching these small images together to form an image of the microfluidic device under test.

Both scanning and stitching systems have shortcomings. For example, both types of systems operate at a relatively low system frequency, which is proportional to the area imaged as a function of time. Conventional systems operate at frequencies on the order of 1-20 cm$^2$ per minute. For some interesting assays, such as protein calorimetry and nucleic acid amplification, system frequencies greater than about 1-20 cm$^2$ per minute are generally required to image the fluorescent processes occurring in the reaction vessels of the microfluidic device. Conventional scanning and stitching systems are not able to meet these performance goals. In addition to slowing system throughput, these scanning and stitching system can limit the potential for utilizing certain assays, e.g., performance of real-time PCR.

Therefore, there is a need in the art for improved methods and systems for imaging one or more entities suspended in a volume of fluid in a chamber of a microfluidic device.

SUMMARY OF THE INVENTION

According to the present invention, techniques for microfluidic systems are provided. In particular, the invention provides a method and system for imaging one or more entities suspended in a volume of fluid in a chamber of a microfluidic device. More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

In a specific embodiment, the present invention provides an apparatus for imaging one or more selected fluorescence indications from a microfluidic device. The apparatus includes an imaging path coupled to least one chamber in at least one microfluidic device. The imaging path provides for transmission of one or more fluorescent emission signals derived from one or more samples in the at least one chamber of the at least one microfluidic device. The chamber has a chamber size, the chamber size being characterized by an actual spatial dimension normal to the imaging path. The apparatus also includes an optical lens system coupled to the imaging path. The optical lens system is adapted to transmit the one or more fluorescent signals associated with the chamber.

In another specific embodiment, a method of imaging one or more selected fluorescence indications from at least one chamber of a microfluidic device is provided. The method includes transmitting one or more fluorescent emission signals derived from one or more samples in the at least one chamber of at least one microfluidic device along an imaging path coupled to the at least one chamber. The at least one chamber has a chamber size, the chamber size being characterized by an actual spatial dimension normal to the imaging path. The method also includes transmitting the one or more fluorescent emission signals associated with the chamber through an optical lens system coupled to the imaging path. The optical lens system is adapted to reduce a size of the actual spatial dimension to a determined level.

In yet another specific embodiment of the present invention, a system for imaging one or more indications from one or more chambers of a microfluidic device is provided. The system includes an optical path, the optical path being capable of transmitting one or more images of a portion of a spatial region of a microfluidic device from the portion of the spatial region of the microfluidic device. In an embodiment, the portion of the spatial region of the microfluidic device is characterized by a first dimension. The system also includes a first lens system coupled to a first portion of the optical path. The first lens system is characterized by a first optical characteristic. The system further includes a second lens system coupled to a second portion of the optical path. The second lens system is characterized by a second optical characteristic. The system additionally includes a detector device coupled to a third portion of the optical path. The detector device is operable to capture the one or more images of the portion of the spatial region. Moreover, the detector is adapted to capture the one or more images. The one or more images have a determined size at the detector device of about the first dimension or less.

In an alternative embodiment, a method for imaging one or more indications from one or more chambers of a microfluidic device. The method includes transmitting one or more images of a portion of a spatial region of a microfluidic device from the portion of the spatial region of the microfluidic device along an optical path. The portion of the spatial region of the microfluidic device is characterized by a first dimension. The method also includes coupling a first lens system to a first portion of the optical path. The first lens system is characterized by a first optical characteristic. The method additionally includes coupling a second lens system to a second portion of the optical path. The second lens system is characterized by a second optical characteristic. Moreover, the method includes capturing the one or more images of the portion of the spatial region using a detector device. The detector device is coupled to a third portion of the optical path and the one or more images have a determined size at the detector device of about the first dimension or less.

In another alternative embodiment, a method of imaging microfluidic devices is provided the method includes capturing an image of a spatial region associated with at least a determined number of chambers of a microfluidic device using an image detection spatial region during a time frame of less than one minute. In a specific embodiment, the capturing of the image of the spatial region is substantially free from a stitching and/or scanning process.

In yet another alternative embodiment, an apparatus for imaging one or more selected fluorescence indications from a microfluidic device is provided. The apparatus includes an imaging path coupled to least one chamber in at least one microfluidic device. The imaging path provides for transmission of one or more fluorescent emission signals derived from one or more samples in the at least one chamber of the at least one microfluidic device. The apparatus also includes an optical filter device coupled to a first spatial portion of the imaging path provided for transmission of the one or more emission signals. The optical filter device is adapted to transmit a selected spectral bandwidth from the one or more fluorescent emission signals and is adapted to process one or more chromatic aberrations associated with the one or more fluorescent emission signals to a determined level.

In a particular embodiment, a method of analyzing processes in elastomeric microfluidic devices is provided. The method includes capturing an image of at least 96 chambers in a time period of less than one minute. In an embodiment, each of the chambers in the at least 96 chambers is in fluidic isolation from any of the other chambers in the at least 96 chambers. The method also includes processing the image.

In another particular embodiment, an apparatus for imaging an microfluidic device comprising a plurality of processing sites is provided. The plurality of processing sites contain at least one sample selected from M samples and at least one reagent selected from N reagents. The apparatus includes an illumination system coupled to the microfluidic device and adapted to illuminate the microfluidic device with electromagnetic radiation. The apparatus also includes an imaging system coupled to the microfluidic device and adapted to receive electromagnetic radiation emitted from the plurality of processing sites. The apparatus additionally includes a detector coupled to the imaging system.

In yet another particular embodiment, an optical imaging system is provided. The optical imaging system includes a computer and an optical illumination system adapted to illuminate an elastomeric microfluidic array device including at least 1,536 reaction chambers in fluidic isolation. The elastomeric microfluidic array device includes an elastomeric block formed from a plurality of layers. At least one layer of the plurality of layers has at least one recess formed therein. The recess has at least one deflectable membrane integral to the layer with the recess. The optical imaging system also includes an optical detection system.

In yet another alternative particular embodiment, a method of imaging one or more selected fluorescence indications from a plurality of chambers in a microfluidic device is provided. The method includes transmitting one or more fluorescent emission signals along an imaging path, the one or more fluorescent emission signals derived from one or more samples in at least one of the plurality of chambers in the microfluidic device. The method also includes selectively transmitting a subset of the one or more fluorescent emission signals along the imaging path utilizing an optical filter device adapted to pass fluorescent emission signals within a predetermined spectral bandwidth and adapted to process one or more chromatic aberrations associated with the one or more fluorescent emission signals to a determined level.

In a specific embodiment, the method further includes reading a portion of the subset of the one or more fluorescent emission signals at a detector, capturing the one or more fluorescent emission signals derived from the one or more samples in at least one of the plurality of chambers in the microfluidic device, irradiating at least 96 chambers in the at least one microfluidic device, wherein each of the chambers in a group of more than 48 chambers is in fluidic isolation from any of the other chambers in the group of more than 48 chambers, and maintaining the at least one microfluidic device at a predetermined temperature at a determined time, wherein the predetermined temperature at the predetermined time is a portion of a multi-step thermocycling profile. In another specific embodiment, processing the one or more chromatic aberrations associated with the one or more fluorescent emission signals includes reducing the one or more chromatic aberrations to a predetermined level. The predetermined level is characterized by a predetermined shift in a focal point associated with a first ray characterized by a first color and a second ray characterized by a second color. In yet another specific embodiment, the optical filter device includes a plurality of zero-power doublets and a plurality of spectral filters.

In an embodiment according to the present invention, the use of an optical imaging system to collect information related to an microfluidic device is provided. In a specific embodiment, the use of the imaging system includes a microfluidic device comprising greater than 63 chambers. In another specific embodiment, the use of the imaging system includes a microfluidic device that has an elastomeric microfluidic device. In an alternative embodiment, the use of the imaging system includes a microfluidic device comprising greater than 95 chambers. In another alternative embodiment, the use of the imaging system includes a microfluidic device comprising greater than 383 chambers. In yet another alternative embodiment, the use of the imaging system includes a microfluidic device comprising greater than 511 chambers. In an additional embodiment, the use of the imaging system includes a microfluidic device comprising greater than or equal to 2,304 chambers. In another additional embodiment, the use of the imaging system includes a microfluidic device comprising greater than or equal to 9,216 chambers. In yet another additional embodiment, the use of the imaging system includes a microfluidic device comprising greater than or equal to 100,000 chambers.

According to another embodiment of the present invention, the use of an optical imaging system to collect information related to an microfluidic device is provided. The use of the optical system includes an elastomeric microfluidic device adapted to perform protein crystallization processes in a particular embodiment. In another embodiment, the use of imaging system includes an elastomeric microfluidic device that is adapted to perform fluorescence processes. In yet another embodiment, the use of the imaging system includes an elastomeric microfluidic device that is adapted to perform reactions at a selected temperature or range of temperatures over time. In another specific embodiment, the optical imaging system is used to collect information related to PCR reactions. In yet another specific embodiment, the use of the imaging system includes a microfluidic device comprising closed reaction chambers in microfluidic isolation. In other embodiments, the use of the imaging system includes a thermal controller that is coupled to the microfluidic device.

In an alternative embodiment, the use of an optical imaging system to image a microfluidic device is provided. In this alternative embodiment, the optical imaging system has a plurality of doublets adapted to reduce a value of chromatic aberration to a predetermined level. In an embodiment, the optical imaging system is characterized by an NA greater than 0.23. In another embodiment, the optical imaging system has an NA greater than or equal to 0.36. In yet another embodiment, the optical imaging system has an NA greater than 0.2. In a specific embodiment, the optical imaging system comprises a first spectral filter coupled to a first doublet and a second spectral filter coupled to a second doublet. Moreover, in an additional embodiment, the first doublet reduces a value of chromatic aberration at a first wavelength passed by the first spectral filter to a first predetermined level and the second doublet reduces a value of chromatic aberration at a second wavelength passed by the second spectral filter to a second predetermined level. In some embodiments, the first doublet and the second doublet are zero-power doublets. In other embodiments, the first spectral filter, the first doublet, the second spectral filter, and the second doublet are arranged as a filter wheel.

In another embodiment of the present invention, the use of a fluorescence imaging system to acquire a plurality of images, including one or more fluorescent emission signals, from an microfluidic device is provided. The use of the fluorescence imaging system includes a microfluidic device that has greater than 63 reaction chambers in fluidic isolation from other reaction chambers. In an embodiment, the use of the fluorescence imaging system includes a microfluidic device that has an elastomeric microfluidic device. In another embodiment, the use of the fluorescence imaging system includes a plurality of reaction chambers that are characterized by a volume of less than 10 nl. In yet another embodiment, the use of the fluorescence imaging system includes an elastomeric microfluidic device that is characterized by an array density greater than or equal to 100 reaction chambers per $cm^2$. In an alternative embodiment, the fluorescence imaging system includes an optical filter device, the optical filter device being adapted to pass a selected spectral bandwidth from the one or more fluorescent emission signals and being adapted to process one or more chromatic aberrations associated with the one or more fluorescent emission signals to a determined level.

In an embodiment of the present invention, an optical system for interrogating samples in a microfluidic system is provided. In the optical system provided by this embodiment, the detector consists of an array (e.g. a CCD) equal to or larger in dimensions than the microfluidic system which is imaged onto it. In another embodiment, the detector is optically coupled to the microfluidic device using at least one lens. In yet another embodiment, the detector is not in conformal contact with the microfluidic device. In a specific embodiment, the detector is in conformal contact with the microfluidic device. In another specific embodiment, chromatic aberration correction systems as discussed throughout the specification are utilized in the optical train.

In another embodiment, an optical system for interrogating a microfluidic device is provided. The optical system has a magnification $M \geq NA_o/NA_{det}$, where $NA_o$ is the object/sample-side NA and $NA_{det}$ is the maximum NA allowable onto the detector before losses due to reflection occurring at the detector face pass a threshold value. In a specific embodiment, the detector is a CCD and $NA_{det}=0.36$. In another embodiment, the detector is a CCD and $0.23 \leq NA_{det} \leq 0.5$.

In an additional embodiment, an optical system for interrogating samples in a microfluidic system is provided. The detector comprises an array (e.g. a CCD) equal to M times the dimensions of the area of the microfluidic device containing reaction chambers. In an embodiment, the area of the microfluidic device includes the sample chambers to be interrogated. In this embodiment, $M=NA_o/NA_{det}+/-10\%$, where $NA_o$ is the maximum NA acceptable as determined by depth-of-focus considerations related to the acceptable crosstalk between reaction chambers, their XY spacing and size, and their extent along the Z axis, and $NA_{det}$ is such that ≤40% of incident light is lost at the detector surface due to reflections, vignetting, and the like. In a specific embodiment, the $NA_{det}$ is such that ≤30% of incident light is lost at the detector surface due to reflections, vignetting, and the like. In another specific embodiment, the $NA_{det}$ is such that ≤20% of incident light is lost at the detector surface due to reflections, vignetting, and the like. In yet another specific embodiment, the $NA_{det}$ is such that ≤10% of incident light is lost at the detector surface due to reflections, vignetting, and the like. In an alternative embodiment, M is ≥1. In another alternative embodiment, M=1.

Numerous benefits are achieved using the present invention over conventional techniques. Some embodiments provide optical imaging systems to generate and detect fluorescence from a microfluidic device. Additionally, embodiments of the present invention provide optical systems that reduce chromatic aberration through the use of zero-power achromatic doublets coupled to spectral filters.

The capability of performing a number of applications on a single platform are provided by embodiments of the present invention. For example genomics applications including gene expression and genotyping are performed using embodiments of the present invention. Moreover, Digital Isolation and Detection (DID) applications are made possible. As an example, applications related to cancer detection as well as single cell macro molecule detection and quantification are provided. Furthermore, proteomics applications including protein-ligand binding and an immunoassay processes are provided through embodiments of the present invention.

Additionally, depending upon the embodiments of the present invention, certain benefits and/or advantages may be achieved to overcome certain limitations associated with other techniques. The following has been determined based upon calculations:

Some scanning systems have a desired resolution of 10 um. In these systems, there are a total of 3000×3000 (=approximately $10^{67}$) "spots" for which fluorescence is desirably quantified. For example, to accomplish this in 10 seconds, the residence time at each spot is ~1 microsecond. Accordingly, a linescan (3000 points) would be complete in 3 ms. To get equivalent signal-to-noise to that achieved using embodiments of the present invention, the light intensity should be ~$10^6$ times as bright in the spot as would be achieved by an imaging system according to the present invention acquiring a signal over a period of 1 second. To raster a spot across 3 cm in 3 ms, 1000 times per second, is often mechanically challenging. In addition, collection of the emission signal with high efficiency is desired. This generally requires either a large field optic or a high NA flying head (e.g., moving at >=10 m/s). In this case, the data collected at the lower right hand corner of a device will be 10 seconds older than the data collected in the upper left hand corner of the device, which is undesirable in some applications.

Some stitching systems acquire multiple images and stitch them together to form a composite image. In one system, in order to stitch together an image from multiple 3 mm×3 mm images, 100 images are utilized. The total time used to acquire these individual images would be 100 ms. Assuming that approximately half the time is spent moving and half the time is spent acquiring an image, the image time will be ~50 ms. This system would generally require a light intensity ~20 times as intense as utilized in embodiments of the present invention acquiring a signal over a period of 1 second, and/or a higher-NA objective. In addition, these systems generally need a fast stage—capable of moving 3 mm and coming to a complete stop in 50 ms. Additionally, these systems generally require careful calibration of both motion and light intensity to eliminate image artifacts from stitching. The data collected at the lower right hand corner of the device will be 10 seconds older than the data collected in the upper left hand corner, which is undesirable in some applications.

Some embodiments of the present invention provide imaging systems in which the area of the microfluidic device is imaged all at once. In an embodiment in which 10 seconds per image is available, several seconds of integration time are available. Synchronization problems are reduced or eliminated as data is collected from all the pixels at the same time. Moreover, embodiments of the present invention generally illuminate the entire microfluidic device (~31 mm×31 mm area) at once and utilize lens systems with high NAs and a large field of view. As described throughout the present specification, embodiments of the present invention provide methods and systems that are less complex and more powerful than conventional systems. Depending upon the embodiment, one or more of these limitations may be overcome by the present methods and systems according to embodiments of the present invention. Further details of the present invention may be found throughout the present specification and more particularly below. Depending upon the embodiment, one or more of these benefits may exist. These and other benefits have been described throughout the present specification and more particularly below.

Various additional objects, features and advantages of the present invention can be more fully appreciated with reference to the detailed description and accompanying drawings that follow.

DETAILED DESCRIPTION OF SPECIFIC EMBODIMENTS

Figure 1A:
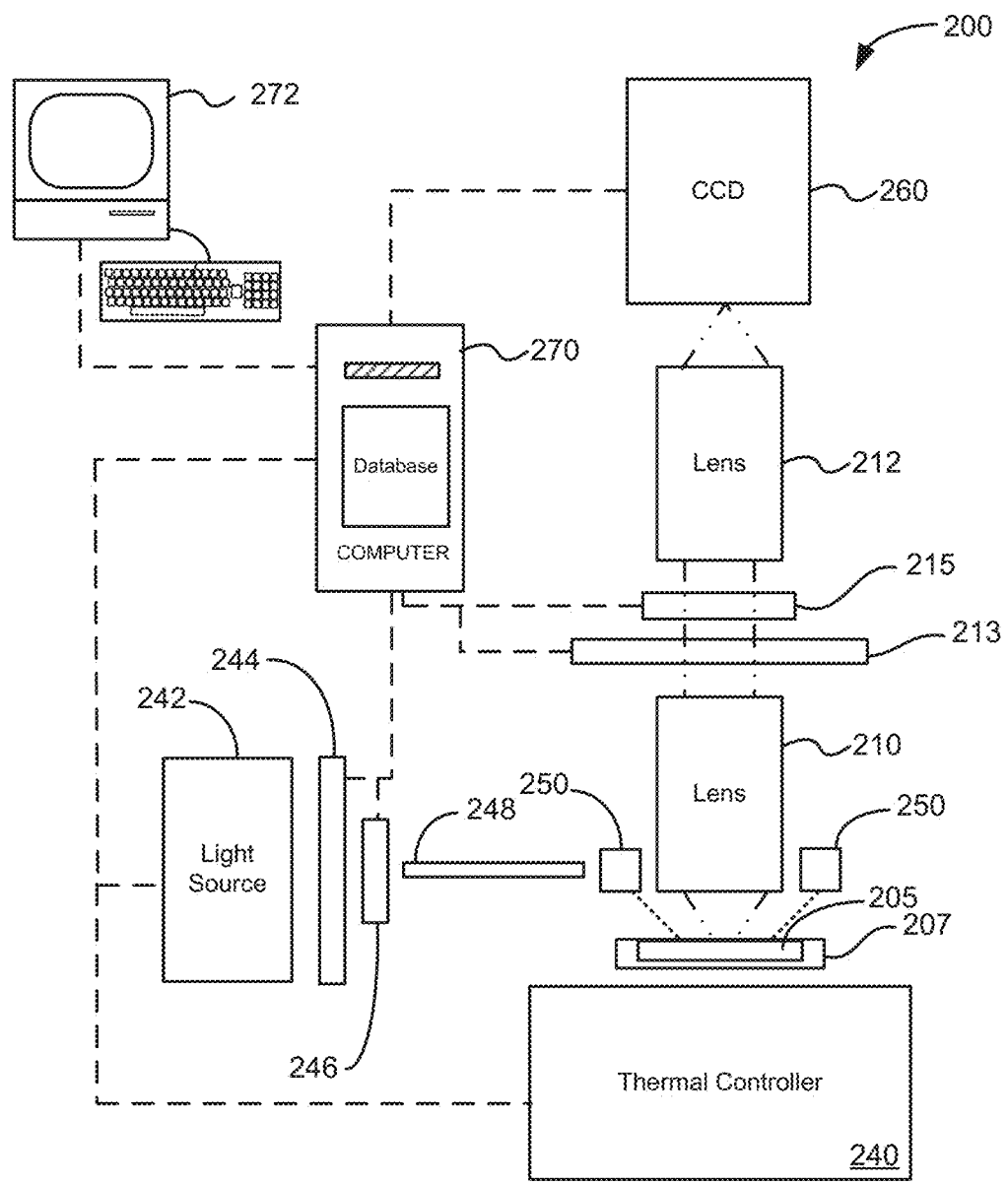
FIG. 1A is a simplified schematic diagram illustrating an optical imaging system according to an embodiment of the present invention.

According to the present invention, techniques for microfluidic systems are provided. In particular, the invention provides a method and system for imaging one or more entities suspended in a volume of fluid in a chamber of a microfluidic device. More particularly, the present method and system for imaging uses indications from a fluorescence signal associated with the one or more entities in the microfluidic device. Merely by way of example, the techniques for microfluidic methods and systems are applied using fluorescent, chemiluminescent, and bioluminescent readers coupled to the microfluidic device, but it would be recognized that the invention has a much broader range of applicability.

In the present application, references are made to certain types of "reaction" chambers in a microfluidic device. In general, these "reaction chambers" include processing sites, processing chambers, and/or reaction sites, any combination of these, and the like. These chambers may be closed, partially closed, open, partially open, sealed, or combinations thereof, including any temporary or transient conditions involving any of these states, and the like. In some embodiments, the chambers are sealed, capable of being sealed, closeable, isolated, capable of being isolated, and combinations thereof, and any combination or single condition of any temporary or transient conditions involving any of these states, and the like. Therefore, use of the term reaction chamber is not intended to limit the present invention, but to include these other structures. Additionally, the term chamber is not intended to limit the present invention, but should be used in its ordinary meaning, unless specific features associated with the chamber have been recited. Of course, there can be other variations, modifications, and alternatives.

Moreover, through the present application, references are made to fluorescent indications from a microfluidic device. Included within the scope of the present invention are not only fluorescent indications, but luminescent indications, including chemiluminescent, electroluminescent, electrochemiluminescent, and phospholuminescent, bioluminescent, and other luminescent processes, or any other processing involving any other type of indications that may be detected using a detection device. As will be evident to one of skill in the art, methods and systems operable in the detection and analysis of these fluorescent and luminescent indications are transferable from one indication to another. Additionally, although some embodiments of the present invention utilize spectral filters as optical elements, this is not required by the present invention. Some fluorescent and luminescent applications do not utilize spectral filters in the optical excitation path, the optical emission path, or both. As described herein, other embodiments utilize spectral filters. One of skill in the art will appreciate the differences associated with particular applications.

In some embodiments, a variety of devices and methods for conducting microfluidic analyses are utilized herein, including devices that can be utilized to conduct thermal cycling reactions such as nucleic acid amplification reactions. The devices differ from conventional microfluidic devices in that they include elastomeric components; in some instances, much or all of the device is composed of elastomeric material. For example, amplification reactions can be linear amplifications, (amplifications with a single primer), as well as exponential amplifications (i.e., amplifications conducted with a forward and reverse primer set).

The methods and systems provided by some embodiments of the present invention utilize blind channel type devices in performing nucleic acid amplification reactions. In these devices, the reagents that are typically deposited within the reaction sites are those reagents necessary to perform the desired type of amplification reaction. Usually this means that some or all of the following are deposited: primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. As discussed in more detail throughout the present specification, when a matrix device is utilized to conduct an amplification reaction, samples containing nucleic acid template are flowed through the vertical flow channels and the amplification reagents through the horizontal flow channels or vice versa.

PCR is perhaps the best known amplification technique. The devices utilized in embodiments of the present invention are not limited to conducting PCR amplifications. Other types of amplification reactions that can be conducted include, but are not limited to, (i) ligase chain reaction (LCR) (see Wu and Wallace, *Genomics* 4:560 (1989) and Landegren et al., *Science* 241:1077 (1988)); (ii) transcription amplification (see Kwoh et al., *Proc. Natl. Acad. Sci. USA* 86:1173 (1989)); (iii) self-sustained sequence replication (see Guatelli et al., *Proc. Nat. Acad. Sci. USA,* 87:1874 (1990)); and (iv) nucleic acid based sequence amplification (NASBA) (see, Sooknanan, R. and Malek, L., *BioTechnology* 13: 563-65 (1995)). Each of the foregoing references are incorporated herein by reference in their entirety for all purposes.

Moreover, certain devices are designed to conduct thermal cycling reactions (e.g., PCR) with devices that include one or more elastomeric valves to regulate solution flow through the device. Thus, methods for conducting amplification reactions with devices of this design are also provided.

Amplification products (amplicons) can be detected and distinguished (whether isolated in a reaction chamber or at any subsequent time) using routine methods for detecting nucleic acids. Amplicons comprising double-stranded DNA can be detected using intercalation dyes such as SYBR™, Pico Green (Molecular Probes, Inc., Eugene, Oreg.), ethidium bromide and the like (see Zhu et al., 1994, Anal. Chem. 66:1941-48) and/or gel electrophoresis. More often, sequence-specific detection methods are used (i.e., amplicons are detected based on their nucleotide sequence). Examples of detection methods include hybridization to arrays of immobilized oligo or polynucleotides, and use of differentially labeled molecular beacons or other "fluorescence resonance energy transfer" (FRET)-based detection systems. FRET-based detection is a preferred method for detection according to some embodiments of the present invention. In FRET-based assays a change in fluorescence from a donor (reporter) and/or acceptor (quencher) fluorophore in a donor/acceptor fluorophore pair is detected. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur and can be detected. A variety of assays are known including, for example and not limitation, template extension reactions, quantitative RT-PCR, Molecular Beacons, and Invader assays, these are described briefly below.

FRET and template extension reactions utilize a primer labeled with one member of a donor/acceptor pair and a nucleotide labeled with the other member of the donor/acceptor pair. Prior to incorporation of the labeled nucleotide into the primer during an template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719. The reactions can optionally be thermocycled to increase signal using the temperature control methods and apparatus described throughout the present specification.

A variety of so-called "real time amplification" methods or "real time quantitative PCR" methods can also be used to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method. See, for example, U.S. Pat. No. 5,723,591.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the 'stem-loop' format and the 'duplex' format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., Advances in Nucleic Acid and Protein Analysis 3826:117-125, 2000) and U.S. Pat. No. 6,706,471.

A variety of multiplex amplification systems can be used in conjunction with the present invention. In one type, several different targets can be detected simultaneously by using multiple differently labeled probes each of which is designed to hybridize only to a particular target. Since each probe has a different label, binding to each target to be detected based on the fluorescence signals. By judicious choice of the different labels that are utilized, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Many diseases linked to genome modifications, either of the host organism or of infectious organisms, are the consequence of a change in a small number of nucleotides, frequently involving a change in a single nucleotide. Such single nucleotide changes are referred to as single nucleotide polymorphisms or simply SNPs, and the site at which the SNP occurs is typically referred to as a polymorphic site. The devices described herein can be utilized to determine the identity of a nucleotide present at such polymorphic sites. As an extension of this capability, the devices can be utilized in genotyping analyses. Genotyping involves the determination of whether a diploid organism (i.e., an organism with two copies of each gene) contains two copies of a reference allele (a reference-type homozygote), one copy each of the reference and a variant allele (i.e., a heterozygote), or contains two copies of the variant allele (i.e., a variant-type homozygote). When conducting a genotyping analysis, the methods of the invention can be utilized to interrogate a single variant site. However, as described further below in the section on multiplexing, the methods can also be used to determine the genotype of an individual in many different DNA loci, either on the same gene, different genes or combinations thereof.

Devices to be utilized for conducting genotyping analyses are designed to utilize reaction sites of appropriate size to ensure from a statistical standpoint that a copy of each of the two alleles for a diploid subject are present in the reaction site at a workable DNA concentrations. Otherwise, an analysis could yield results suggesting that a heterozygote is a homozygote simply because a copy of the second allele is not present at the reaction site. Table 1 below indicates the number of copies of the genome present in a 1 nl reaction volume at various exemplary DNA concentrations that can be utilized with the devices described herein.

TABLE 1

Number of genome copies present in a 1 nanoliter volume at the indicated DNA concentration.

| Volume (nanoliter) | [DNA] (µg/µL) | N |
|---|---|---|
| 1 | 0.33 | 100 |
| 1 | 0.10 | 32 |
| 1 | 0.05 | 16 |
| 1 | 0.01 | 3 |
| 1 | 0.003 | 1 |

As a general matter, due to stochastic proportioning of the sample, the copy number present before an amplification reaction is commenced determines the likely error in the measurement. Genotyping analyses using certain devices are typically conducted with samples having a DNA concentration of approximately 0.10 µg/µL, although the current inventors have run successful TaqMan reactions at concentrations in which there is a single genome per reaction site.

Genotyping analyses can be conducted using a variety of different approaches. In these methods, it is generally sufficient to obtain a "yes" or "no" result, i.e., detection need only be able to answer the question whether a given allele is present. Thus, analyses can be conducted only with the primers or nucleotides necessary to detect the presence of one allele potentially at a polymorphic site. However, more typically, primers and nucleotides to detect the presence of each allele potentially at the polymorphic site are included.

Single Base Pair Extension (SBPE) reactions are one technique specifically developed for conducting genotyping analyses. Although a number of SPBE assays have been developed, the general approach is quite similar. Typically, these assays involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods and related methods are discussed, for example, in U.S. Pat. Nos. 5,846,710; 6,004,744; 5,888,819; 5,856,092; and 5,710,028; and in WO 92/16657.

Genotyping analyses can also be conducted using quantitative PCR methods. In this case, differentially labeled probes complementary to each of the allelic forms are included as reagents, together with primers, nucleotides and polymerase. However, reactions can be conducted with only a single probe, although this can create ambiguity as to whether lack of signal is due to absence of a particular allele or simply a failed reaction. For the typical biallelic case in which two alleles are possible for a polymorphic site, two differentially labeled probes, each perfectly complementary to one of the alleles are usually included in the reagent mixture, together with amplification primers, nucleotides and polymerase. Sample containing the target DNA is introduced into the reaction site. If the allele to which a probe is complementary is present in the target DNA, then amplification occurs, thereby resulting in a detectable signal as described in the detection above. Based upon which of the differential signal is obtained, the identity of the nucleotide at the polymorphic site can be determined. If both signals are detected, then both alleles are present. Thermocycling during the reaction is performed as described in the temperature control section supra.

Gene expression analysis involves determining the level at which one or more genes is expressed in a particular cell. The determination can be qualitative, but generally is quantitative. In a differential gene expression analysis, the levels of the gene(s) in one cell (e.g., a test cell) are compared to the expression levels of the same genes in another cell (control cell). A wide variety of such comparisons can be made. Examples include, but are not limited to, a comparison between healthy and diseased cells, between cells from an individual treated with one drug and cells from another untreated individual, between cells exposed to a particular toxicant and cells not exposed, and so on. Genes whose expression levels vary between the test and control cells can serve as markers and/or targets for therapy. For example, if a certain group of genes is found to be up-regulated in diseased cells rather than healthy cells, such genes can serve as markers of the disease and can potentially be utilized as the basis for diagnostic tests. These genes could also be targets. A strategy for treating the disease might include procedures that result in a reduction of expression of the up-regulated genes.

The design of the microfluidic devices utilized in embodiments of the present invention is helpful in facilitating a variety of gene expression analyses. Because the devices contain a large number of reaction sites, a large number of genes and/or samples can be tested at the same time. Using the blind flow channel devices, for instance, the expression levels of hundreds or thousands of genes can be determined at the same time. The devices also facilitate differential gene expression analyses. With the matrix design, for example, a sample obtained from a healthy cell can be tested in one flow channel, with a sample from a diseased cell run in an immediately adjacent channel. This feature enhances the ease of detection and the accuracy of the results because the two samples are run on the same device at the same time and under the same conditions.

A variety of matrix or array-based devices are also utilized according to embodiments of the present invention. Certain of these devices include: (i) a first plurality of flow channels formed in an elastomeric substrate, (ii) a second plurality of flow channels formed in the elastomeric substrate that intersect the first plurality of flow channels to define an array of reaction sites, (iii) a plurality of isolation valves disposed within the first and second plurality of flow channels that can be actuated to isolate solution within each of the reaction sites from solution at other reaction sites, and (iv) a plurality of guard channels overlaying one or more of the flow channels and/or one or more of the reaction sites to prevent evaporation of solution therefrom. The foregoing devices can be utilized to conduct a number of different types of reactions, including those involving temperature regulation (e.g., thermocycling of nucleic acid analyses).

Some of the microfluidic devices utilize a design typically referred to herein as "blind channel" or "blind fill" and are characterized in part by having a plurality of blind channels, which are flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction site. During manufacture of this type of device, one or more reagents for conducting an analysis are deposited at the reaction sites, thereby resulting in a significant reduction in the number of input and outputs. Additionally, the blind channels are connected to an interconnected network of channels such that all the reaction sites can be filled from a single, or limited number, of sample inputs. Because of the reduction in complexity in inputs and outputs and the use of only a single valve to isolate each reaction site, the space available for reaction sites is increased. Thus, the features of these devices means that each device can include a large number of reaction sites (e.g., up to tens of thousands) and can achieve high reaction site densities (e.g., over 1,000-4,000 reaction sites/cm$^2$). Individually and collectively, these features also directly translate into a significant reduction in the size of these devices compared to traditional microfluidic devices.

Other microfluidic devices that are disclosed herein utilize a matrix design. In general, microfluidic devices of this type utilize a plurality of intersecting horizontal and vertical flow channels to define an array of reaction sites at the points of intersection. Thus, devices of this design also have an array or reaction sites; however, there is a larger number of sample inputs and corresponding outputs to accommodate the larger number of samples with this design. A valve system referred to as a switchable flow array architecture enables solution be flowed selectively through just the horizontal or flow channels, thus allowing for switchable isolation of various flow channels in the matrix. Hence, whereas the blind channel devices are designed to conduct a large number of analyses under different conditions with a limited number of samples, the matrix devices are constructed to analyze a large number of samples under a limited number of conditions. Still other devices are hybrids of these two general design types.

Other microfluidic devices are massively partitioning devices (DID) such as described in PCT publication WO 2004/089810, U.S. patent application Ser. No. 10/819,088 filed Apr. 5, 2004 (now U.S. Pat. No. 7,691,333), commonly assigned patent application No. 60/687,010 filed Jun. 2, 2006 entitled "Analysis using microfluidic partitioning devices," each of which are incorporated by reference in their entirety for all purposes. Using massively partitioning devices, a sample can be partitioned into a multitude of isolated reaction chambers, and reactions carried out simultaneously in each chamber.

The microfluidic devices that are described herein are further characterized in part by utilizing various components such as flow channels, control channels, valves and/or pumps fabricated from elastomeric materials. In some instances, essentially the entire device is made of elastomeric materials. Consequently, such devices differ significantly in form and function from the majority of conventional microfluidic devices that are formed from plastics or silicon-based materials. The number of reaction chambers provided varies according to embodiments of the present invention.

The design of the devices enables them to be utilized in combination with a number of different heating systems. Thus, the devices are useful in conducting diverse analyses that require temperature control. Additionally, those microfluidic devices adapted for use in heating applications can incorporate a further design feature to minimize evaporation of sample from the reaction sites. Devices of this type in general include a number of guard channels and/or reservoirs or chambers formed within the elastomeric device through which water can be flowed to increase the water vapor pressure within the elastomeric material from which the device is formed, thereby reducing evaporation of sample material from the reaction sites.

In another embodiment, a temperature cycling device may be used to control the temperature of the microfluidic devices. Preferably, the microfluidic device would be adapted to make thermal contact with the microfluidic device. Where the microfluidic device is supported by a substrate material, such as a glass slide or the bottom of a carrier plate, such as a plastic carrier, a window may be formed in a region of the carrier or slide such that the microfluidic device, preferably a device having an elastomeric block, may directly contact the heating/cooling block of the temperature cycling device. In a preferred embodiment, the heating/cooling block has grooves therein in communication with a vacuum source for applying a suction force to the microfluidic device, preferably a portion adjacent to where the reactions are taking place. Alternatively, a rigid thermally conductive plate may be bonded to the microfluidic device that then mates with the heating and cooling block for efficient thermal conduction resulting.

The array format of certain of the devices means the devices can achieve high throughput. Collectively, the high throughput and temperature control capabilities make the devices useful for performing large numbers of nucleic acid amplifications (e.g., polymerase chain reaction (PCR)). Such reactions will be discussed at length herein as illustrative of the utility of the devices, especially of their use in any reaction requiring temperature control. However, it should be understood that the devices are not limited to these particular applications. The devices can be utilized in a wide variety of other types of analyses or reactions. Examples include analyses of protein-ligand interactions and interactions between cells and various compounds. Further examples are provided throughout the present specification.

The microfluidic devices disclosed herein are typically constructed at least in part from elastomeric materials and constructed by single and multilayer soft lithography (MSL) techniques and/or sacrificial-layer encapsulation methods (see, e.g., Unger et al. (2000) Science 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al. (2000) Science 288:113-116, and PCT Publication WO 02/43615 and WO 01/01025.

The devices provided herein incorporate such pumps and/or valves to isolate selectively a reaction site at which reagents are allowed to react. Alternatively, devices without pumps and/or valves are utilized that use pressure driven flow or polymerization processes to close appropriate channels and thereby selectively isolate reaction sites. The reaction sites can be located at any of a number of different locations within the device. For example, in some matrix-type devices, the reaction site is located at the intersection of a set of flow channels. In blind channel devices, the reaction site is located at the end of the blind channel.

If the device is to be utilized in temperature control reactions (e.g., thermocycling reactions), then, as described in greater detail infra, the elastomeric device is typically fixed to a support (e.g., a glass slide). The resulting structure can then be placed on a temperature control plate, for example, to control the temperature at the various reaction sites. In the case of thermocycling reactions, the device can be placed on any of a number of thermocycling plates.

Because the devices are made of elastomeric materials that are relatively optically transparent, reactions can be readily monitored using a variety of different detection systems at essentially any location on the microfluidic device. Most typically, however, detection occurs at the reaction site itself (e.g., within a region that includes an intersection of flow channels or at the blind end of a flow channel). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

Devices utilizing the matrix design generally have a plurality of vertical and horizontal flow channels that intersect to form an array of junctions. Because a different sample and reagent (or set of reagents) can be introduced into each of the flow channels, a large number of samples can be tested against a relatively large number of reaction conditions in a high throughput format. Thus, for example, if a different sample is introduced into each of M different vertical flow channels and a different reagent (or set of reagents) is introduced into each of N horizontal flow channels, then M×N different reactions can be conducted at the same time. Typically, matrix devices include valves that allow for switchable isolation of the vertical and horizontal flow channels. Said differently, the valves are positioned to allow selective flow just through the vertical flow channels or just through the horizontal flow channels. Because devices of this type allow flexibility with respect to the selection of the type and number of samples, as well as the number and type of reagents, these devices are well-suited for conducting analyses in which one wants to screen a large number of samples against a relatively large number of reaction conditions. The matrix devices can optionally incorporate guard channels to help prevent evaporation of sample and reactants.

Some high-density matrix designs utilize fluid communication vias between layers of the microfluidic device to weave control lines and fluid lines through the device. For example, by having a fluid line in each layer of a two layer elastomeric block, higher density reaction cell arrangements are possible. As will be evident to one of skill in the art, multi-layer devices allow fluid lines to cross over or under each other without being in fluid communication. For example, in a particular design, a reagent fluid channel in a first layer is connected to a reagent fluid channel in a second layer through a via, while the second layer also has sample channels therein, the sample channels and the reagent channels terminating in sample and reagent chambers, respectively. The sample and reagent chambers are in fluid communication with each other through an interface channel that has an interface valve associated therewith to control fluid communication between each of the chambers of a reaction cell. In use, the interface is first closed, then reagent is introduced into the reagent channel from the reagent inlet and sample is introduced into the sample channel through the sample inlet. Containment valves are then closed to isolate each reaction cell from other reaction cells. Once the reaction cells are isolated, the interface valve is opened to cause the sample chamber and the reagent chamber to be in fluid communication with each other so that a desired reaction may take place. One of ordinary skill in the art would recognize many variations, modifications, and alternatives.

Accordingly, a particular design for a microfluidic device provides for a microfluidic device adapted to react M number of different samples with N number of different reagents comprising: a plurality of reaction cells, each reaction cell comprising a sample chamber and a reagent chamber, the sample chamber and the reagent chamber being in fluid communication through an interface channel having an interface valve associated therewith for controlling fluid communication between the sample chamber and the reagent chamber; a plurality of sample inlets each in fluid communication with the sample chambers; a plurality of reagent inlets each in fluid communication with the reagent chambers; wherein one of the sample inlets or reagent inlets is in fluid communication with one of the sample chambers or one of the reagent chambers, respectively, through a via. Certain embodiments include having the reaction cells be formed within an elastomeric block formed from a plurality of layers bonded together and the interface valve is a deflectable membrane; having the sample inlets be in communication with the sample chamber through a sample channel and the reagent inlet in fluid communication with the reagent chamber through a reagent channel, a portion of the sample channel and a portion of the reagent channel being oriented about parallel to each other and each having a containment valve associated therewith for controlling fluid communication therethrough; having the valve associated with the sample channel and the valve associated with the reagent channel in operable communication with each other through a common containment control channel; having the containment common control channel located along a line about normal to one of the sample channel or the reagent channel.

The microfluidic devices utilized in embodiments of the present invention may be further integrated into the carrier devices described in co-pending and commonly owned U.S. Patent Application No. 60/557,715 by Unger filed on Mar. 29, 2004, which is incorporated herein for all purposes. The carrier of Unger provides on-board continuous fluid pressure to maintain valve closure away from a source of fluid pressure, e.g., house air pressure. Unger further provides for an automated system for charging and actuating the valves of the present invention as described therein. An another preferred embodiment, the automated system for charging accumulators and actuating valves employs a device having a platen that mates against one or more surfaces of the microfluidic device, wherein the platen has at least two or more ports in fluid communication with a controlled vacuum or pressure source, and may include mechanical portions for manipulating portions of the microfluidic device, for example, but not limited to, check valves.

Another device utilized in embodiments of the present invention provides a carrier used as a substrate for stabilizing an elastomeric block. Preferably the carrier has one or more of the following features; a well or reservoir in fluid communication with the elastomeric block through at least one channel formed in or with the carrier; an accumulator in fluid communication with the elastomeric block through at least one channel formed in or with the carrier; and, a fluid port in fluid communication with the elastomeric block, wherein the fluid port is preferably accessible to an automated source of vacuum or pressure, such as the automated system described above, wherein the automated source further comprises a platen having a port that mates with the fluid port to form an isolated fluid connection between the automated system for applying fluid pressure or vacuum to the elastomeric block. In devices utilized in certain embodiments, the automated source can also make fluid communication with one or more accumulators associated with the carrier for charging and discharging pressure maintained in an accumulator. In certain embodiments, the carrier may further comprise a region located in an area of the carrier that contacts the microfluidic device, wherein the region is made from a material different from another portion of the carrier, the material of the region being selected for improved thermal conduction and distribution properties that are different from the other portion of the carrier. Preferred materials for improved thermal conduction and distribution include, but are not limited to silicon, preferably silicon that is highly polished, such as the type of silicon available in the semiconductor field as a polished wafer or a portion cut from the wafer, e.g., chip.

As described more fully below, embodiments of the present invention utilize a thermal source, for example, but not limited to a PCR thermocycler, which may have been modified from its original manufactured state. Generally the thermal source has a thermally regulated portion that can mate with a portion of the carrier, preferably the thermal conduction and distribution portion of the carrier, for providing thermal control to the elastomeric block through the thermal conduction and distribution portion of the carrier. In a preferred embodiment, thermal contact is improved by applying a source of vacuum to a one or more channels formed within the thermally regulated portion of the thermal source, wherein the channels are formed to contact a surface of the thermal conduction and distribution portion of the carrier to apply suction to and maintain the position of the thermal conduction and distribution portion of the carrier. In a preferred embodiment, the thermal conduction and distribution portion of the carrier is not in physical contact with the remainder of the carrier, but is associated with the remainder of the carrier and the elastomeric block by affixing the thermal conduction and distribution portion to the elastomeric block only and leaving a gap surrounding the edges of the thermal conduction and distribution portion to reduce parasitic thermal effects caused by the carrier. It should be understood that in many aspects of the invention described herein, the preferred elastomeric block could be replaced with any of the known microfluidic devices in the art not described herein, for example devices produced such as the GeneChip® by Affymetrix® of Santa Clara, Calif., USA, or by Caliper of Mountain View, Calif., USA. U.S. patents issued to Soane, Parce, Fodor, Wilding, Ekstrom, Quake, or Unger, describe microfluidic or mesoscale fluidic devices that can be substituted for the elastomeric block of the present invention to take advantage of the thermal advantages and improvements, e.g., suction positioning, reducing parasitic thermal transfer to other regions of the fluidic device, which are described above in the context of using an elastomeric block.

Utilizing systems and methods provided according to embodiments of the present invention, throughput increases are provided over 384 well systems. As an example, throughput increases of a factor of 4, 6, 12, and 24 and greater are provided in some embodiments. These throughput increases are provided while reducing the logistical friction of operations. Moreover the systems and methods of embodiments of the present invention enable multiple assays for multiple samples. For example, in a specific embodiment 96 samples and 96 assays are utilized to provide a total of 9,216 data points. In a particular example, the 96 assays are components of a TaqMan 5' Nuclease Assay.

Furthermore, embodiments of the present invention provide reduced reaction volumes. In embodiments of the present invention, reaction volumes ranging from 10 picoliters to 100 nanoliters are utilized. In some embodiments, reaction volumes greater than 100 nanoliters are utilized. Merely by way of example, in an embodiment, the methods and systems of the present invention are utilized with reaction volumes of 10 picoliters, 50 picoliters, 100 picoliters, 250 picoliters, 500 picoliters, and 1 nanoliter. In alternative embodiments, reaction volumes of 2 nanoliters, 5 nanoliters, 10 nanoliters, 20 nanoliters, 30 nanoliters, 40 nanoliters, 50 nanoliters, 75 nanoliters, and 100 nanoliters are utilized.

Depending on the geometry of the particular microfluidic device and the size of the microfluidic device and the arrangement of the fluid communication paths and processing site, embodiments of the present invention provide for a range of processing site (or reaction chamber) densities. In some embodiments, the methods and systems of the present invention are utilized with chamber densities ranging from about 100 chambers per $cm^2$ to about 1 million chambers per $cm^2$. Merely by way of example, microfluidic devices with chamber densities of 250, 1,000, 2,500, 10,000, 25,000, 100,000, and 250,000 chambers per $cm^2$ are utilized according to embodiments of the present invention. In some embodiments, chamber densities in excess of 1,000,000 chambers per $cm^2$ are utilized, although this is not required by the present invention.

Operating microfluidic devices with such small reaction volumes reduces reagent usage as well as sample usage. Moreover, some embodiments of the present invention provide methods and systems adapted to perform real-time detection, when used in combination with real-time quantitative PCR. Utilizing these systems and methods, six orders of linear dynamic range are provided for some applications as well as quantitative resolution high enough to allow for the detection of sub-nanoMolar fluorophore concentrations in 10 nanoliter volumes. One of ordinary skill in the art would recognize many variations, modifications, and alternatives.

Methods conducted with certain blind channel type devices involve providing a microfluidic device that comprises a flow channel formed within an elastomeric material; and a plurality of blind flow channels in fluid communication with the flow channel, with an end region of each blind flow channel defining a reaction site. At least one reagent is introduced into each of the reaction sites, and then a reaction is detected at one or more of the reaction sites. The method can optionally include heating the at least one reagent within the reaction site. Thus, for example, a method can involve introducing the components for a nucleic acid amplification reaction and then thermocycling the components to form amplified product. As more fully described below, an optical imaging system adapted to characterize reactions occurring in certain microfluidic devices is provided according to embodiments of the present invention.

As illustrated in FIG. 1A, optical imaging systems provided according to some embodiments of the present invention include fluorescence imaging systems coupled to thermal control modules. Such systems are adapted to collect data from microfluidic chips with N×M geometries. In some embodiments, N is equal to M. For example, embodiments of the present invention utilize microfluidic devices with 48×48 reaction chambers, 96×96 reaction chambers, and other geometries. In a particular embodiment, 96 samples and 96 reagents are utilized in a microfluidic device with a 96×96 reaction chamber geometry. As will be evident to one of skill in the art, the methods and systems provided according to embodiments of the present invention enable one platform to perform multiple applications.

FIG. 1A is a simplified schematic diagram illustrating an optical imaging system according to an embodiment of the present invention. As illustrated in FIG. 1A, an optical source 242 is provided according to embodiments of the present invention. As will be described more fully below, in some embodiments of the present invention, light from optical source 242 is utilized to induce fluorescence in a sample. In other embodiments, chemiluminescence is utilized as a indicator. Depending on the embodiment, system components will be added, removed, or used, as will be evident to one of skill in the art. In various embodiments, optical sources including light emitting diodes (LEDs), lasers, arc lamps, incandescent lamps, and the like are utilized. These sources may be polychromatic or monochromatic. In a particular embodiment, the optical source is characterized by a first spectral bandwidth. In a specific embodiment, the optical source is a white light source producing optical radiation over a spectral range from about 400 nm to about 700 nm. Merely by way of example, a Lambda LS 300 W Xenon Arc lamp, available from Sutter Instruments of Novato, Calif. is utilized as an optical source is some embodiments of the present invention. As will be evident to one of skill in the art, other optical sources characterized by larger or smaller spectral bandwidths are capable of being utilized in alternative embodiments.

Excitation filter wheel 244 is illustrated in FIG. 1A. In some embodiments, for example, those in which the optical source is polychromatic, the excitation filter wheel 244 is utilized to spectrally filter the light emitted by the optical source 242. Of course, multiple filters could also be used. As an example, in an embodiment, the excitation filter wheel provides a number of spectral filters each adapted to pass a predetermined wavelength range as appropriate for exciting specific fluorescence from a sample. As illustrated in FIG. 1A, the excitation filter wheel 244 is coupled to computer 270, providing for computer control of the filters. In a particular embodiment, the excitation filter wheel provides a number of spectral filters:

Filter 1: A filter with a center wavelength of 485 nm and a spectral bandwidth of 20 nm;

Filter 2: A filter with a center wavelength of 530 nm and a spectral bandwidth of 20 nm; and Filter 3: A filter with a center wavelength of 580 nm and a spectral bandwidth of 20 nm.

As will be evident to one of skill in the art, embodiments of the present invention are not limited to these particular spectral filters, but will utilize spectral filters adapted for fluorescence processes for particular samples. Moreover, although the previous discussion related to the use of a filter wheel, this is not required by the present invention. In alternative embodiments, spectral filters are provided in geometries other than a wheel. For example, spectral filters that drop into a filter holder, electro-optic filters, filters placed into the optical path by actuators, and the like are included according to embodiments of the present invention. Moreover, in other embodiments, the optical source is a tunable laser adapted to emit radiation at predetermined wavelengths suitable for excitation of fluorescence. One of ordinary skill in the art would recognize many variations, modifications, and alternatives.

As illustrated in FIG. 1A, excitation shutter 246 is provided according to embodiments of the present invention. The excitation shutter is operated under control of a computer 270 in some embodiments, to block/pass the optical signal generated by the optical source 242 and spectrally filtered by the excitation filter wheel 244. Depending on the application, the excitation source is blocked while samples are inserted and removed from the system as well as for calibration operations. In some embodiments, the excitation shutter is not utilized, for example, in embodiments utilizing laser sources, which provide alternative means to extinguish the optical source.

When the excitation shutter is operated in an open position, the optical excitation signal passes through a fiber bundle 248 and is directed so as to impinge on a microfluidic device 205 provided in chip carrier to a seven. Other embodiments of the present invention utilize quartz light guides, liquid light guides, other scrambling systems, and the like to increase illumination homogeneity. As illustrated in FIG. 1A, the excitation optical signal is directed, through reflection by optical illuminator 250, refraction, or combinations thereof, to impinge on a surface of the microfluidic device 205. As illustrated in FIG. 1A, illumination of the microfluidic device is via optical illuminator 250. In other embodiments illumination maybe coupled to the microfluidic device obliquely from one or more sides of device, via a ring light, or via a portion of the collection optical train (the optical path between the microfluidic device and the detector 260.

In some embodiments, the illumination of the microfluidic device with light produced by the excitation source is provided over a two-dimensional area of the sample. In these embodiments, a large field of view is provided, which enables the performance of fluorescence applications that involve imaging of time resolved chemical processes and reactions. As an example, fluorescent imaging of protein calorimetry and nucleic acid amplification processes are time resolved processes that benefit from embodiments of the present invention. In some of these processes, simultaneously excitation of the fluorescent samples provided in a number of reaction chambers and simultaneous collection of the fluorescent signals produced by the reactions occurring in the number of reaction chambers is desirable. In other processes, for instance, fluorescence lifetime imaging, a brief excitation pulse is followed by detection (and analysis) of the fluorescent signal as it decays in time from an initial level. One of ordinary skill in the art would recognize many variations, modifications, and alternatives.

As an example, nucleic acid amplification processes typically include the target DNA, a thermostable DNA polymerase, two oligonucleotide primers, deoxynucleotide triphosphates (dNTPs), a reaction buffer, and magnesium. Once assembled, the reaction is placed in a thermal cycler, an instrument that subjects the reaction to a series of different temperatures for varying amounts of time. This series of temperature and time adjustments is referred to as one cycle of amplification. Each cycle theoretically doubles the amount of targeted sequence (amplicon) in the reaction. Ten cycles theoretically multiply the amplicon by a factor of about one thousand; 20 cycles, by a factor of more than a million in a matter of hours. In some applications, it is desirable to acquire fluorescent imaging data from a large area (e.g., on the order of several $cm^2$) in a time period ranging from seconds to minutes.

In some embodiments of the present invention, the methods and systems provided by embodiments of the present invention facilitate image capture processes that are performed in a predetermined time period. Merely by way of example, in an embodiment of the present invention a method of imaging microfluidic devices is provided. The method includes capturing an image of a spatial region associated with at least a determined number of chambers of a microfluidic device using an image detection spatial region during a time frame of less than one minute, whereupon the capturing of the image of the spatial region is substantially free from a stitching and/or scanning process.

Embodiments of the present invention provide a variety of time frames for image capture, ranging from 1 millisecond to 1 minute. In some embodiments, time frames for image capture are greater than one minute. Depending on the emission properties associated with the processes performed in the chambers of the microfluidic device, the time frame for image capture will vary. For example, in an embodiment, the time frame is 10 ms, 50 ms, 100 ms, 250 ms, 500 ms, 750 ms, or 1 second. In other embodiments, the time frame is 2 seconds, 5 seconds, 10 seconds, 15 seconds, 20 seconds, 30 seconds, 40 seconds, 50 seconds, or 1 minute. Of course, the time frame will depend on the particular applications.

In some embodiments, the image capture process is performed in a synchronous manner, capturing an image of a determined number of chambers simultaneously. As an example, in an exemplary PCR process, the microfluidic device is maintained at a temperature of 92° C. for a time period of 15 seconds. Subsequently, the microfluidic device is maintained at a temperature of 60° C. for 60 seconds. The heating and cooling cycle is repeated at a one minute cycle period for a number of cycles. Utilizing embodiments of the present invention, images of a determined number of chambers present in the microfluidic device are acquired synchronously, while the chambers are maintained at a uniform temperate as a function of position. For example, a two-dimensional image of an entire microfluidic device may be acquired utilizing a 30 second exposure while the microfluidic device is maintained at the temperature of 60° C. One of skill in the art will appreciate the benefits provided by the present invention over raster scanning or stitching systems, in which images of chambers in a first portion (e.g., an upper left quadrant) of the microfluidic device are acquired prior to images of chambers in a second portion (e.g., a lower right quadrant) of the microfluidic device.

In other embodiments, multiple images are acquired of the determined number of chambers during a time frame of less than one minute. As an example of these embodiments, multiple images associated with multiple fluorophores are acquired in a particular embodiment. During the 60 second time period during which the microfluidic device is maintained at the temperature of 60° C., three consecutive images utilizing exposures of 20 seconds may be acquired for three different fluorophores, for example, Rox™, Vic®, and Fam™. Of course, depending on the application, the exposure times may be shorter, even as short as a second or less. Utilizing these multiple images, differential fluorescence ratios can be calculated and analyzed. Of course, depending on the strength of the fluorescent emissions, the exposure times for the various fluorophores may be modified as appropriate the particular application. In this way, embodiments of the present invention provide for imaging of a microfluidic device in multiple spectral bands while the microfluidic device is maintained a constant temperature. The constant temperature, as illustrated by the previous example, may be a portion of a PCR process including cyclical temperature processes.

Embodiments of the present invention provide methods and systems are also adapted to perform and analyze chemiluminescence processes. In some of these processes, reactions occur on a first time scale and an image of the chemiluminescence process is acquired on a second time scale. In a particular process, the second time scale is less than the first time scale. Thus, embodiments of the present invention are adapted to capture synchronous images of chemiluminescence processes when the samples in the reaction chambers of interest have been reacting for an equal amount of time. In some of these processes, temperature control, including temperature cycling of the samples is provided, whereas in other embodiments, the reaction chambers are maintained at a constant temperature.

As illustrated in FIG. 1A, a thermal controller, also referred to as a temperature controller, 240 is provided according to embodiments of the present invention. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of channels of a microfluidic device).

Figure 1B:
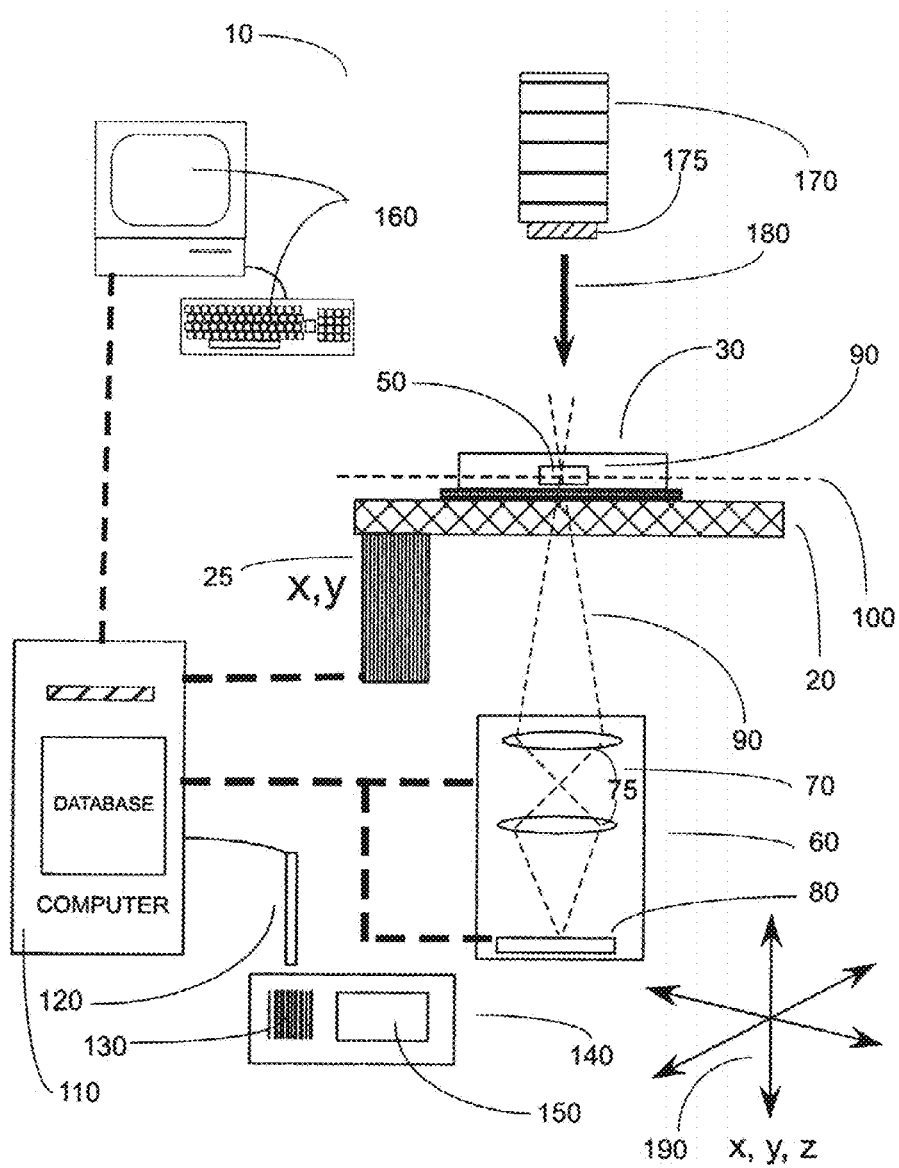
FIG. 1B depicts an overview of an exemplary imaging system according to an alternative embodiment of the present invention.
Figure 1C:
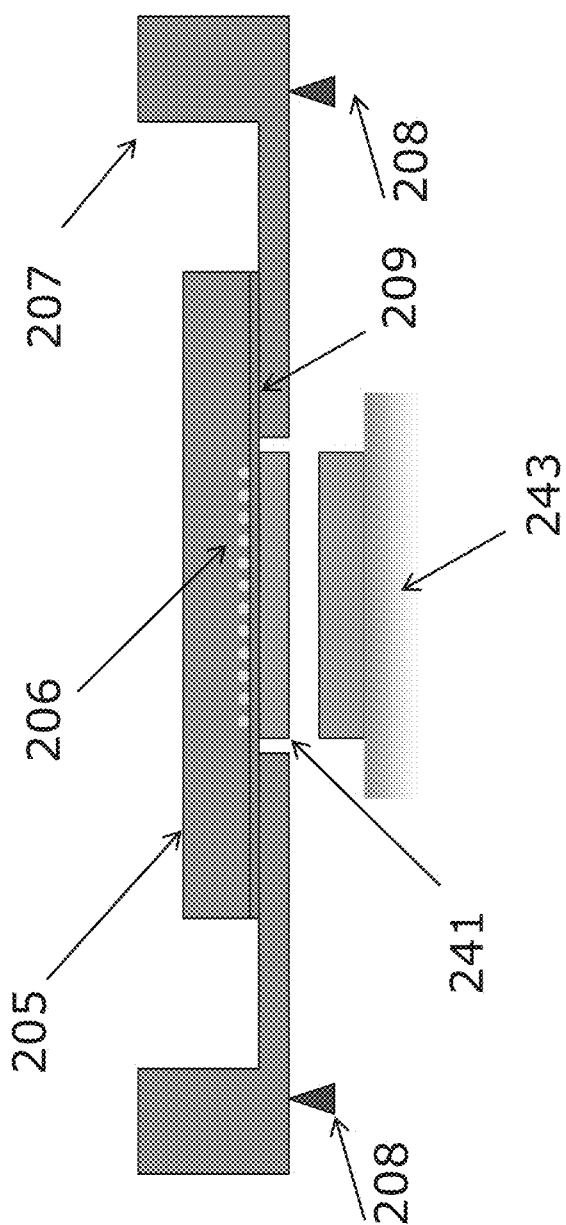
FIG. 1C is a simplified schematic diagram illustrating a thermal control device according to a embodiment of the present invention.

FIG. 1C is a simplified schematic diagram illustrating a thermal control device according to a embodiment of the present invention. As illustrated in FIG. 1C, microfluidic device 205 includes sample array 206. As will be evident to one of skill in the art, although the sample array 206 is illustrated in one dimension, three dimensional sample arrays are provided according to embodiments of the present invention. As an example, in some microfluidic devices utilized in embodiments of the present invention, an array of reaction chambers and fluid communication channels extend into the plane of the figure. The elements of the microfluidic device, including the reaction chambers are characterized by a depth in a third dimension. The microfluidic device 205 is supported by carrier 207, which, in turn, is supported by carrier supports 208. The microfluidic device or chip bottom layer 209, which in some embodiments is compliant, is coupled to the carrier 207 as well as the Integrated Heat Spreader (IHS) 241. Thermal platen 243 is illustrated in FIG. 1C and described more fully below. In some embodiments, a hard contact between the microfluidic device and the IHS/platen is provided. Moreover, as described in more detail below, vacuum techniques are utilized in some embodiments to position and hold the microfluidic device with respect to the carrier.

Generally, the devices are placed on a thermal cycling plate to thermal cycle the device. A variety of such plates are readily available from commercial sources, including for example the ThermoHybaid Px2 (Franklin, Mass.), MJ Research PTC-200 (South San Francisco, Calif.), Eppendorf Part# E5331 (Westbury, N.Y.), Techne Part#205330 (Princeton, N.J.).

In some embodiments, the microfluidic device is contacted with a thermal control device such that the thermal control device is in thermal communication with the thermal control source so that a temperature of the reaction in at least one of the reaction chamber is changed as a result of a change in temperature of the thermal control source. In different embodiments, the thermal transfer device may comprise a semiconductor, such as silicon, may comprise a reflective material, and/or may comprise a metal.

The thermal control device may be adapted to apply a force to the thermal transfer device to urge the thermal transfer device towards the thermal control source. The force may comprise a mechanical pressure, a magnetic force, an electrostatic force, or a vacuum force in different embodiments. For example, in one embodiment, the force comprises a vacuum force applied towards the thermal transfer device through channels formed in a surface of the thermal control device or the thermal transfer device. A level of vacuum achieved between the surface of the thermal control device and a surface (or a portion of a surface) of the thermal transfer device may be detected. Such detection may be performed with a vacuum level detector located at a position along the channel or channels distal from a location of a source of vacuum. When the vacuum does not exceed a preset level, an alert may be manifested or a realignment protocol may be engaged.

The array device may be contacted with the thermal control device by employment of one or more mechanical or electromechanical positioning devices. Carrying out of the method may be automatically controlled and monitored. For example, such automatic control and monitoring may be performed with an automatic control system in operable communication with a robotic control system for introducing and removing the array device from the thermal control device. The progress of the reactions may also be monitored.

A unit may be provided comprising the thermal control device. A system may be provided comprising the array device and the thermal control device. To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152-158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation of appropriate wavelengths (e.g. thermal, infrared, and the like) would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature. Other electrical phenomena, such as capacitance and inductance, can be exploited to detect temperature in accordance with embodiments of the present invention. One of ordinary skill in the art would recognize many variations, modifications, and alternatives.

Imaging system 200 operates, in one embodiment, in the following manner. First, microfluidic device 205 is securely placed on carrier 207. Based on a fixed feature of the microfluidic device 205, for example, an edge of the base support of microfluidic device, computer 270 then causes and x,y drive (not shown) to move the carrier 207 to align the microfluidic device in a first x,y position. In some embodiments, one or more fiducial markings are utilized during the alignment and positioning process. In a specific embodiment, a user of the system then registers the precise coordinate of one or more fiducial marks with the imaging system. In other embodiments, this process is performed automatically as the centroids of the fiducials can be calculated precisely by locating a symmetric XY fiducial object and removing any non-symmetric components. In some embodiments, features of the fiducials, such as edges and corners are utilized during alignment processes. One of ordinary skill in the art would recognize many variations, modifications, and alternatives.

Under the control of computer 270, either adjustments of the carrier 207 to position it in the focal plane of the optical elements 210 and 212 or adjustments of the optical elements 210 and 212 to position the focal plane of the optical elements 210 and 212 to the carrier 207 are performed. In preferred embodiments, the field of view can embrace an entire microfluidic device, including the number of reaction chambers present on the microfluidic device.

Figure 2A:
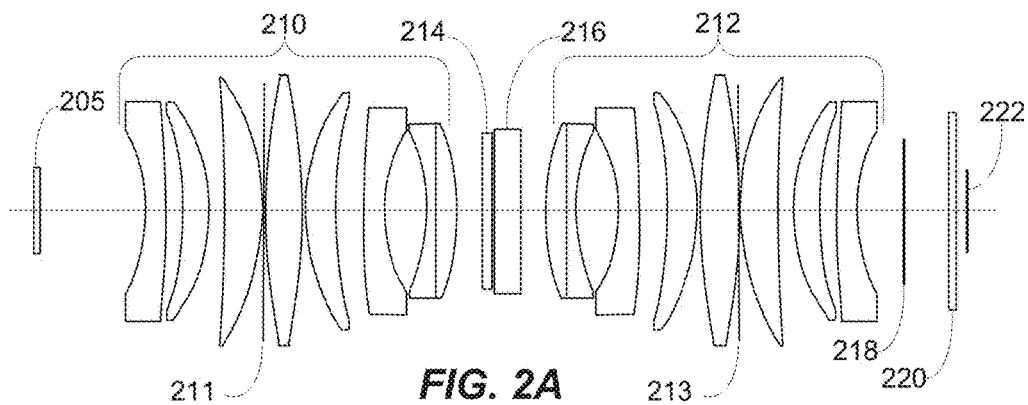
FIGS. 2A-2C are simplified schematic diagrams illustrating a lens assembly according to an embodiment of the present invention.

A fluorescent, chemiluminescent, or optical signal emitted by the chemical processes occurring in the reaction chambers of the microfluidic device is collected by a first lens system 210. In some embodiments of the present invention, the first lens system is a multi-element optical train including one or more lenses and one or more apertures. As illustrated in FIG. 2A, first lens system 210 includes single lens elements as well as doublets, and the like. The optical properties of the first lens system 210 including focal length, f/#, and the like are selected to provide desired optical performance. One of ordinary skill in the art would recognize many variations, modifications, and alternatives. An emission shutter 215 is illustrated in FIG. 1A to provide for blocking of light rays propagating more than a predetermined distance from the optical axis, although this is not required by the present invention.

Referring once again to FIG. 1A, an optical filter device 213 is provided as part of the optical assembly. In some embodiments, the optical filter device is a filter wheel 213 comprising a number of optical elements adapted for passing and optically processing fluorescent or chemiluminescent emissions produced by fluorescently or chemiluminescently labeled reagents. As an example, in an embodiment, a first section of the emission filter wheel is adapted to pass fluorescent emissions produced by a first fluorescent dye, for example, Cy™3 Fluor, available from Amersham Biosciences, part of GE Healthcare of Piscataway, N.J. A second section of the emission filter wheel is adapted to pass fluorescent emissions produced by a second fluorescent dye, for example, Cy™5 Fluor also available from Amersham Biosciences. Of course, the use of these fluorescent dyes is not required by the present invention. In alternative embodiments, Alexa Fluors, available from Invitrogen Corporation of Carlsbad, Calif., are utilized. As an example, in another embodiment, a first section of the emission filter wheel is adapted to pass fluorescent emissions produced by a third fluorescent dye, for example, Alexa Fluor 350, available from Invitrogen Corporation. A second section of the emission filter wheel is adapted to pass fluorescent emissions produced by a fourth fluorescent dye, for example, Alexa Fluor 488, also available from Invitrogen Corporation. Additional details related to the emission filter wheel will be provided below.

In some embodiments, the optical filter device 213 and the emission shutter 215 are located between the first lens system and the second lens system. In some of these embodiments, light rays passing through the optical filter device propagate at small angles with respect to the optic axis. As will be evident to one of skill in the art, spectral filters (e.g., interference filters) placed in regions with small incident ray angle are simpler to design and can potentially provide narrower total spectral bandwidth, through such narrow spectral bandwidth characteristics and/or filter positioning are required by the present invention. As illustrated in FIG. 1A, both the optical filter device and the emission shutter are coupled to computer 270, providing for computer control of these elements. Moreover as will be evident to one of skill in the art, multiple, and possibly multiple identical filters, may be provided in the optical path to increase the blockage of excitation wavelengths. In some embodiments these filters are angled with respect to the optic axis so that light rays reflected off of the filters walk out of the optical path.

In other embodiments, certain intercalation dyes that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

An second lens system 212 is also illustrated in FIG. 1A. Fluorescent or chemiluminescent emission passing through the optical filter device 213 and the emission shutter 215 is focused by the second lens system onto a detector 260. In an embodiment, the detector is a CCD camera array, but this is not required by the present invention. In a particular embodiment, an array detector, approximately the size of the microfluidic device, is utilized. Preferably, the pixel size of the detector array 260 is selected to provide an area smaller than the area of the reaction chambers in the microfluidic device, thereby providing multiple detector pixels per reaction chamber. In a particular embodiment, the detector 260 is a CCD array with approximately 15 µm×15 µm pixels.

A number of different detection strategies can be utilized with the microfluidic devices that are provided herein. Selection of the appropriate system is informed in part on the type of event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization anisotropy, fluorescence lifetime, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

In some embodiments, detection occurs at a "detection section," or "detection region." These terms and other related terms refer to the portion of the microfluidic device at which detection occurs. In some microfluidic devices, the detection section is generally the reaction chambers present in the microfluidic device. The detection section for other devices may be within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by one ore more optical detectors. The optical detector can include one or more photodiodes (e.g., avalanche photodiodes), a fiber-optic light guide leading, for example, to a photomultiplier tube or tubes, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength herein monitored. This feature enables the devices described herein to utilize a number of optical detection systems that are not possible with conventional silicon-based microfluidic devices.

A particular embodiment of the present invention utilizes a detector in the form of a CCD camera and an optical path that provides for a large field of view and a high numerical aperture to maximize the amount of light collected from each reaction chamber, thereby increasing detection sensitivity. In this embodiment, the CCD is used as an array of photodetectors wherein each pixel or group of pixels corresponds to a reaction chamber rather than being used to produce an image of the array. Thus, the optics may be designed or altered such that image quality is reduced or the image is blurred at the detector in order to increase the useable depth of field of the optical system to collect more light from each reaction chamber. Particularly because the assays contemplated in some embodiments of the present invention include biological assays using fluorescent dyes, which dyes photobleach due to exposure to excitation light hence limiting the total number of signal photons obtainable from a given sample, efficient collection of the limited signal photons can be of importance in instruments such as that discussed. Etendue considerations relate the object and image NA (numerical aperture) and total system magnification for any optical system; since image-side NA can be limited (e.g. by reflection losses at the CCD surface for high-incident-angle rays), in general, arbitrarily high object (sample)-side NA is not achievable simultaneously with arbitrary system magnification. In fact, a larger system magnification can allow a higher object-side NA without requiring a simultaneous (and potentially deleterious for reasons described above) rise in image-side NA. Consequently, in the system described, a large CCD (e.g., 30.7 mm×30.7 mm) focal-plane array has been used to allow for a 1:1 optical system (i.e., a system magnification of 1). This allows a collection NA of 0.36 simultaneous with an image-side NA of 0.36 onto the CCD, which provides reasonable performance with respect to surface reflection losses.

In some embodiments, larger object-side NAs result in reduced object-side depth-of-focus, and hence larger blurring at the detector (assuming blur due to depth of focus greater than or equal to blur due to lens aberrations and other issues) for a given depth of reaction chamber in the sample, limiting the allowable minimum spacing between reaction chambers at the sample if low crosstalk in signal between chambers is to be achieved. In conjunction with a 1:1 optical system, this object-side NA consideration is in good keeping with the ~0.5 NA maximum generally desirable NA onto a CCD (or silicon detector) if one is to avoid reflection losses at the surface thereof. The 1:1 imaging lens system is furthermore inherently free of most odd-order aberrations, increasing the advantage of this particular magnification (M=1). The use of a 1:1 optical system with a detector as large or larger than the microfluidic system to be imaged is thus provided by some embodiments of the present invention as a design for the detailed system.

In other embodiments, there may be a cost constraint related to the size of the detector (e.g. a CCD focal-plane array). For example, some current high quantum-efficiency, full-frame CCD arrays have dimensions of 27.6 mm×27.6 mm. This detector is slightly smaller than a microfluidic device with dimensions of 30.7 mm×30.7 mm, resulting in a system magnification of 0.88 as a design for the system described. Being near system magnification M=1, constraints related to the detector (image-side) incident NA described above are satisfied for such a magnification.

In other embodiments, a given XY-plane (perpendicular to the optical axis) spacing and size of the reaction chambers may be specified (e.g. to achieve a desired density of sample-chambers in the XY-plane), while constraints on the minimum total volume of the chambers remain (e.g. to achieve minimum required chemical volumes, for instance to avoid over-large statistical fluctuations due to small numbers of reagent or target molecules, or simply to achieve a required minimum number of fluorescent or otherwise optically-emitting molecules or objects). In such a case, it may be necessary to extend the chambers parallel to the Z (optical)-axis such that the total volume of each chamber remains equal to or greater than some minimum figure. Greater extension along Z (creating high-aspect ratio, or columnar chambers which concentrate the sample to be interrogated along the Z-axis) will generally result in a larger blur of the chamber image at the detector for given object-side NA, due to depth-of-focus considerations, assuming blur due to depth of focus is greater than or equal to blur due to lens aberrations and other issues. In some situations, this will lead to the user of a lower object-side NA. Use of a lower NA lens system allows for greater depth of focus and hence light collection from a chambers extended parallel to the optic axis without generally incurring inordinate crosstalk in the optical signal between adjacent or nearby chambers. In this way, a greater density of chambers in the X-Y plane (the place perpendicular to the optic axis) may be used without inordinate crosstalk, while the total chamber volume may be kept large by extension of the chambers in Z (parallel to the optic axis). In this case, or other cases where a lower object-side NA is acceptable (e.g., cases where a larger XY spacing of reaction chambers allows for more chamber-image blur at the detector without undue crosstalk; in non-light-limited applications, where higher NA is not essential; where there is sufficient sample that photobleaching is not an issue; non-photobleaching samples, circumstances such as lower acceptable system sensitivity), a lower system magnification (M<1) may be suitable, particularly if $M \geq NA_o/0.5$, or more preferably $M \geq NA_o/0.36$, where $NA_o$=object side NA, or more generally $M \geq NA_o/NA_{det}$ where $NA_{det}$=maximum NA allowable onto the detector face without overlarge reflection/insertion losses to the detector ($NA_{det}$=0.36 to 0.5 for a typical CCD).

In cases where object-side depth-of-focus and/or blur requirements do not necessitate an object-side $NA \leq 0.36$, or possibly 0.5, or more generally $NA_o \leq NA_{det}$, a larger detector is desirable since due to Etendue considerations (as discussed above), since a larger M (generally requiring a larger detector for a given sample size) will allow a smaller $NA_i$ (image-side NA) for a given $NA_o$. Hence where light-collection requirements (e.g. to achieve a certain assay sensitivity) call for a large $NA_o$ (defined by $NA_o > NA_{det}$) and depth-of-focus and other design considerations (e.g. cost) allow for a large $NA_o$, a larger M is desirable such that losses are minimized at the detector. In such embodiments it can be useful to use a detector device, for example, one or more CCD devices, having a size of, or larger than, the area of the microfluidic device to be imaged. Use of such a large detector allows an increase in the magnification of the optical system, and hence (via etendue considerations) higher NA light collection from the sample for a fixed incident NA onto the detector (the latter set, e.g., by reflection losses at the CCD surface at high incoming ray incident angles).

A particularly preferred detector uses a CCD camera and an optical path that provides for a large field of view and a high numerical aperture to maximize the amount of light collected from each reaction chamber, thereby increasing detection sensitivity. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber. In some embodiments, it is useful to employ high aspect ratio, or columnar chambers, to concentrate the sample to be interrogated by the detector along the optical axis of the optical system, and preferably by defocussing the image to increase the depth of field. Use of a low NA lens system, preferably a bilaterally symmetrical lens system is used. It is also useful to use a detector device, for example, one or more CCD devices, having a size of, or larger than, the area of the microfluidic device to be imaged. Used in conjunction with the low NA optics, improved detection sensitivity can be realized.

A detector system can include a light source for stimulating a reporter that generates a detectable signal. The type of light source utilized depends in part on the nature of the reporter being activated. Suitable light sources include, but are not limited to, lasers, laser diodes, white light sources, and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

Certain intercalation dyes that that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

As illustrated in FIG. 1A, some embodiments of the present invention provide a 1:1 imaging system adapted to generate and detect fluorescent, chemiluminescent, bioluminescent, and other signals from the microfluidic device. A 1:1 imaging system is provided in some embodiments that utilizes an image detection device as large as the sample to be imaged. By providing 1:1 imaging of a large field of view, on the order of several $cm^2$, embodiments of the present invention provide increased numerical aperture (NA) optical systems. Because light collection efficiency is approximately proportional to $NA^2$, the increase in NA provided by some embodiments of the present invention enable the collection of suitable fluorescent signals from reaction chambers comprising reaction volumes on the order of one to tens of nanoliters and active fluorophore concentrations on the order of 1.0 nanoMolar. In other embodiments, active fluorophore concentrations in picoMolar ranges provide suitable fluorescent signals.

Additionally, embodiments of the present invention provide for imaging systems that are slightly reducing, forming, for example, an image that ranges from about the same size as the object to about half the object size. For example, in an embodiment, an image of a spatial region of a microfluidic device is transmitted and captured, the spatial region being associated with more than 96 chambers. An image detecting device is used to capture the image of the spatial region using an image detection spatial region that is about equal to or slightly less in size than the spatial region of the microfluidic device. Merely by way of example, the ratio of the area of the spatial region of the microfluidic device to the area of the image of the spatial region can be 1:1, 1:0.99, 1:0.95, 1:0.9, 1:0.88, 1:0.85, 1:0.8. 1:0.7, 1:0.6, and 1:0.5. In some embodiments, the ratio is less than 1:0.5. These particular ratios are merely exemplary, as the ratio selected for the imaging system will depend on the particular application.

In some embodiments, the optical imaging system includes a field of view of about 3 cm×3 cm. In other embodiments, the optical imaging system includes a field of view that ranges from about 1 cm×1 cm to about 5 cm×5 cm. In particular embodiments, an object field of view of 2 cm×2 cm, 2.5 cm×2.5 cm, 2.76 cm×2.76 cm, 3.07 cm×3.07 cm, 3.5 cm×3.5 cm, and 4 cm×4 cm, is provided. In general, the field of view of the optical imaging system is selected to correspond to the spatial region of the microfluidic device, for example, an area including a number of reaction chambers of interest.

Moreover, embodiments of the present invention provide optical imaging systems with a range of numerical apertures. As an example, an NA ranging from 0.1 to 0.5 is provided according to various embodiments. In a particular embodiment, NAs of 0.15, 0.18, 0.2, 0.23, 0.25, 0.3, 0.36, and 0.4 are provided.

The spatial resolution of the optical imaging system will generally be a function of the size of the pixels in the image detecting device. In some embodiments of the present invention, the magnification (equal to one for some embodiments) and the size of the pixels present in the detector will determine the number of pixels associated with each reaction chamber. Generally, it is preferable to have multiple detector pixels associated with each reaction chamber. For example, if a reaction chamber is 45 µm on a side, up to nine square pixels having a side dimension equal to 15 µm will overlap with the reaction chamber in the 1:1 imaging system. Thus, according to embodiments of the present invention, the number of pixels associated with each reaction chamber ranges from 1 to 100. For example, 4 pixel regions, 9 pixel regions, 16 pixel regions, 25 pixel regions, 36 pixel regions, 49 pixel regions, 64 pixel regions, and 81 pixel regions are associated with each reaction chamber according to some embodiments of the present invention.

In embodiments of the present invention, a range of pixel sizes from 1 µm² to 900 µm² are utilized. For example, square pixels 1 µm on a side, 2 µm on a side, 3 µm on a side, 4 µm on a side, 5 µm on a side, 10 µm on a side, 13.5 µm on a side, 15 µm on a side, 20 µm on a side, 25 µm on a side, and 30 µm on a side are utilized in various embodiments of the present invention. As will be evident to one of skill in the art, the pixel size, the detector array dimensions, and the number of pixels per array are related. In alternative embodiments, rectangular pixels with pixel areas ranging from 1 µm² to 900 µm² are utilized.

Moreover, detector arrays, also referred to as image detecting devices, including a range of pixel counts are utilized according to various embodiments of the present invention. Array dimensions range from 512×512 pixel regions to 3,000×3,000 pixel regions. Depending on the availability of detector arrays, greater numbers of pixels per array may be provided in some embodiments. In particular embodiments, array dimensions of 1,024×1,024 pixel regions and 2,048 by 2,048 pixel regions are utilized.

Embodiments of the present invention provide an optical imaging system characterized by several system parameters. For example, a working distance of greater than 35 mm, for instance, 45.92 mm is available through embodiments of the present invention. In another embodiment, a Root-Mean-Square (RMS) spot diameter averaging 13.44 µm with a maximum value of 17.85 µm is provided. Moreover, through embodiments of the present invention, an illumination variation of about ±5% is achieved. In some embodiments, the overall length of the optical imaging system is 542.1 mm with a maximum filter AOI of 12.56 degrees, a maximum beam diameter at the filter of 76 mm, a distortion of <0.10%, and a maximum lens diameter of 5.512 inches.

FIG. 1B is a simplified diagram for an imaging system according to an embodiment of the present invention. In some embodiments, the imaging system illustrated in FIG. 1B is utilized for imaging of microfluidic devices including devices adapted to perform protein crystallization processes. Additional details regarding imaging systems as illustrated in FIG. 1B and associated microfluidic devices are found in commonly owned U.S. patent application Ser. No. 10/902, 494 filed Jul. 28, 2004 (now U.S. Pat. No. 7,583,853) and U.S. patent application Ser. No. 10/851,777 filed May 20, 2004 (now U.S. Pat. No. 7,695,683, the disclosures of which are incorporated by reference herein for all purposes. In particular, additional details regarding microfluidic devices provided according to embodiments of the present invention and their use in conjunction with the imaging system as shown in FIG. 1B are found therein. These diagrams are merely examples, which should not unduly limit the scope of the claims herein. One of ordinary skill in the art would recognize many variations, alternatives, and modifications.

Imaging system (10) operates, in one embodiment, in the following manner. First, microfluidic device (30) is securely placed on stage (20). Based on a fixed feature of the microfluidic device (30), for example, an edge of the base support of microfluidic device (30), computer (110) then causes x,y drive (25) to move stage (20) about to align microfluidic device (30) in a first x,y position with a first of a plurality of fiducial markings, wherein the fiducial markings are embedded within the microfluidic device at a known z dimension distance from a chamber center point, comes into focus by imaging device (60) based on dead reckoning from the fixed feature. A user of the system then registers the precise coordinate of the fiducial with the imaging system. Two or more additional fiducial marks are then likewise mapped with the assistance of a user. In other embodiments, this process is automatic as the centroids of the fiducials can be calculated precisely by locating the symmetric XY fiducial object and removing any non-symmetric components. Imaging device (60), under the control of computer (110) then adjusts the z dimension location of focal plane (100) to focus upon the fiducial marking. For example, once focused upon the first fiducial marking, the imaging system then obtains a first x,y coordinate image of microfluidic device (30) looking for additional fiducial markings within the field of view of imaging device (60). In preferred embodiments, the field of view can embrace an entire metering cell. The computer then analyzes the first x,y coordinate image to determine whether the microfluidic device has skew and stretch, and if skew or stretch are determined, transforms the first x,y image to align the image and coordinate map of the microfluidic device to an idealized coordinate map. The idealized coordinate map is used later during image subtraction and masking steps.

In preferred embodiments, with the microfluidic device x,y coordinate image aligned against the ideal coordinate map, the system then determines whether the stretch, distortion or lack of co-registration between the various microfluidic layers is present in the microfluidic device by comparing the location of the fiducial markings in the x,y coordinate image with the fiducial markings locations in the x,y coordinate image of the ideal stored image map. If differences are present between the actual fiducial locations and the imaged fiducial locations, a matrix transformation, preferably an Affine transformation, is performed to transform the imaged shape of the metering cell into a virtual shape of the ideal metering cell shape. By converting the actual image to a known and fixed ideal image using the matrix transformation computed from the differences between the measured actual fiducial locations and the stored ideal fiducial locations, image subtraction and other image analysis are made possible.

By computing the differences between the coordinate maps through matrix analysis, a matrix transformation may be developed to reform the actual image into an ideal image for use in further image processing described herein. By causing the imaged microfluidic device to conform to a standard shape, image subtraction and masking is possible to maximize the viewable area of a metering cell chamber. Moreover, if defects or debris are present within the chamber at time zero in a series of time based images, such defects or debris can be masked out of subsequent images to avoid false signals when applying automated analysis. In addition to masking off areas of the chambers which contain defects or debris, the walls of the chambers may be subtracted from subsequent images, again so as to not cause false readings in the subsequent analysis. The discrepancy between various layers, such as between the control layer and the channel layer, can also be calculated based on the position of a found object in the control layer, such as the control lines themselves. In another example, this correction is determined based on the control layer fiducials themselves. For certain embodiments, this extra transformation is important since the control layer partitions the protein chamber from the rest of the control line.

Figure 2B:
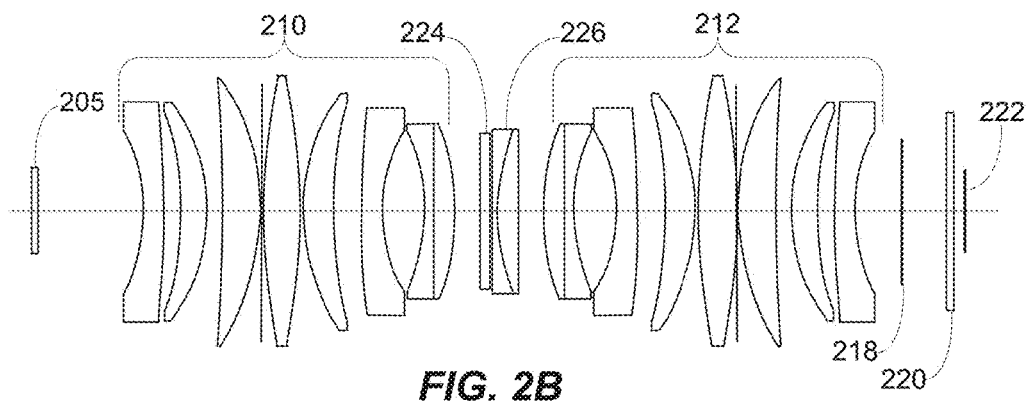
Figure 2C:
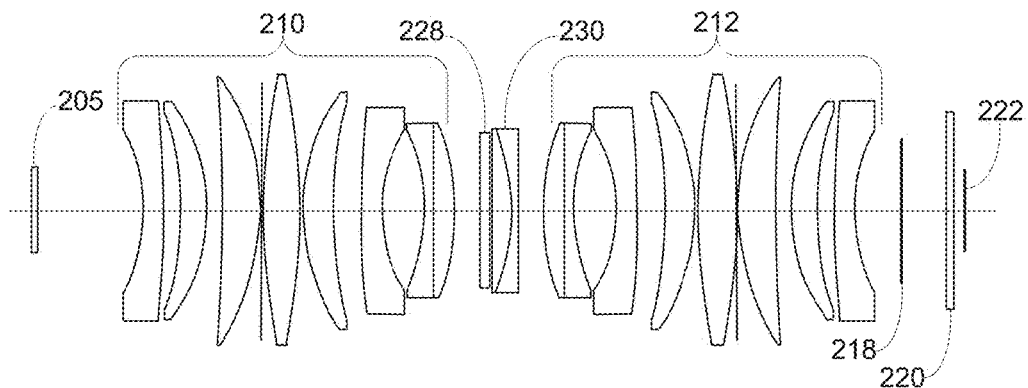

FIGS. 2A-2C are simplified schematic diagrams illustrating a lens assembly according to an embodiment of the present invention. As illustrated in FIGS. 2A-2C, microfluidic device 205 is provided in each of the figures. Although the thermal controller and other system elements are not illustrated in FIGS. 2A-2C, one of skill in the art will appreciate the relationship between the two figures. Accordingly, where appropriate, reference numbers have been carried over from FIG. 1A to further clarify the relationship between the various figures.

First lens system 210 is illustrated in FIG. 2A as including a first aperture 211. As illustrated, the first aperture is positioned between individual lens elements, however, this is not required by the present invention. In other optical designs, the position, size, and other characteristics of the first aperture are selected to achieve predetermined optical design goals. Second lens system 212 is also illustrated in FIG. 2A, including a second aperture 213. As discussed in relation to first lens system 210, the optical elements are arranged in accordance with the predetermined optical design goals.

Referring to FIGS. 1A and 2A-2C, additional details regarding the optical filter device are illustrated. In general, lens systems 210 and 212, along with the optical filter device 213 are provided in a portion of the imaging path. In some embodiments the imaging path is an emission path provided for transmission of one or more fluorescent emission signals from the microfluidic device to that detector. As described more fully below, the optical filter device is adapted to pass a selected spectral bandwidth from the one or more fluorescent emission signals and is adapted to process one or more chromatic aberrations associated with the one or more fluorescent emission signals to a determined level. In some embodiments processing the one or more chromatic aberrations includes reducing such aberrations.

In a particular embodiment, a first spectral filter 214 and a zero-power optical element 216 are provided as illustrated in FIG. 2A. Referring to FIG. 1, the filter/zero-power element combination is present in the optical path between the microfluidic device and the detector when the optical filter device 213 (in some embodiments, an emission filter wheel) is in a first operating position. The optical elements in FIG. 2A are optimized for the transmission and focusing of wavelengths at approximately the center of the optical spectrum. Accordingly, in an embodiment, the spectral filter 214 is centered at a wavelength of 570 nm, associated with the fluorophore Vic®, available from Applied Biosystems of Foster City, Calif. Additionally, the spectral filter is characterized by a spectral bandwidth of 30 nm. As will be described more fully below, in some embodiments, filter/zero-power elements adapted to correct for chromatic aberration are also provided that are centered at other wavelengths, generally at wavelengths shorter and longer than 570 nm.

As discussed in relation to the spectral filter 244 in FIG. 1A, the optical filter device is not limited to the geometry of a wheel. For example, spectral filters, aberration correcting elements, and combinations thereof, that drop into a filter holder are included in embodiments of the present invention. Moreover, electro-optic filters as well as filters placed into the optical path by actuators and the like, combined with aberration correcting elements are also included according to embodiments of the present invention.

FIG. 2B illustrates the first and second lens systems with the emission filter wheel in a second operating position. In the embodiment illustrated in FIG. 2B, the spectral filter 224 is centered at a wavelength of 518 nm (associated with the fluorophore Fam™, available from Applied Biosystems) and is characterized by a spectral bandwidth of 25 nm. Generally, the spectral filter 224 is adapted to transmit fluorescent signals associated with fluorophores emitting at "blue" wavelengths, typically associated with wavelengths near the short wavelength portion of the optical spectrum.

An optical element 226 acting as a zero-power doublet is illustrated in FIG. 2B. In some embodiments, the filter/zero-power doublet is provided as a compound optical element, whereas in other embodiments, the filter and zero power doublet are detached from each other. Moreover, in some embodiments, the emission filter wheel is rotated to modify the position of the filter/zero-power optical elements, transitioning from the first operating position to the second operating position. The zero-power doublet 226 illustrated in FIG. 2B is designed to correct for chromatic aberration introduced by the optical system at "blue" wavelengths. In a specific embodiment, the zero-power doublet is selected to correct for chromatic aberration at the wavelength associated with the emission from a particular fluorophore, for example, Fam™.

In some embodiments, the zero-power doublet is fabricated from separate optical materials with different index of refraction values. Merely by way of example, as illustrated in FIG. 2B, a planar-concave lens is coupled to a convex-planar lens. In a specific embodiment, the zero-power doublet is a Fraunhofer achromat with the optical elements cemented together. In other embodiments, alternative designs are utilized as will be evident to one of skill in the art. In some embodiments, buried doublets as illustrated throughout the specification are utilized to reduce axial chromatic aberration in the blue and red filter bands.

FIG. 2C illustrates the first and second lens systems with the emission filter wheel in a third operating position. In the embodiment illustrated in FIG. 2C, the spectral filter 228 is centered at a wavelength of 645 nm (associated with the fluorophore Rox™, available from Applied Biosciences) and is characterized by a spectral bandwidth of 75 nm. Generally, the spectral filter 228 is adapted to transmit fluorescent signals associated with fluorophores emitting at "red" wavelengths, typically associated with wavelengths near the long wavelength portion of the optical spectrum.

As in FIG. 2B, an optical element 230 acting as a zero-power doublet is illustrated in FIG. 2C. In some embodiments, the filter/zero-power doublet is provided as a compound optical element, whereas in other embodiments, the filter and zero power doublet are detached from each other. Moreover, in some embodiments, the emission filter wheel is rotated to modify the position of the filter/zero-power optical elements, transitioning from the first or second operating positions to the third operating position. The zero-power doublet 230 illustrated in FIG. 2C is designed to correct for chromatic aberration introduced by the optical system at "red" wavelengths. In a specific embodiment, the zero-power doublet is selected to correct for chromatic aberration at the wavelength associated with the emission from a particular fluorophore, for example, Rox™. Comparing FIGS. 2B and 2C, the zero-power doublet illustrated in FIG. 2C comprises a planar-convex lens coupled to a concave-planar lens.

As discussed in relation to FIGS. 2A, 2B, and 2C, the corrective optical elements 216, 226, and 230 associated with their respective filters are designed such that they help correct chromatic aberration at the wavelengths passed by said respective filters. This design allows for more uniform and consistent spot sizes, blur, and other optical characteristics of the lens system across different filters which pass different wavelength regions. These benefits are useful for applications such as that described where tight packing of the reaction chambers in the microfluidic device is utilized. Additionally, design goals for allowable crosstalk between optical signals from different reaction chambers generally places limits on the maximum spot or blur sizes allowed at the image plane. Aberration correction optics reduce the blur or spot size at one wavelength extreme (e.g. a filter passing in the blue wavelength region) and also reduce the blur or spot size at a different wavelength region (e.g. for a filter with a passband in the red wavelength region). This benefit is useful in cases where the overall measurement is a ratiometric one, depending on separate signals detected in, e.g., both the red and blue wavelength regions, thereby improving the sensitivity of the entire assay. The discussion provided above has pertained to specific embodiments, but one of skill in the art will understand that there are many variations of corrective zero-power optics which may be similarly placed in the optical train in conjunction with filters of different wavelength passbands that are included within the scope of the present invention.

Figure 3:
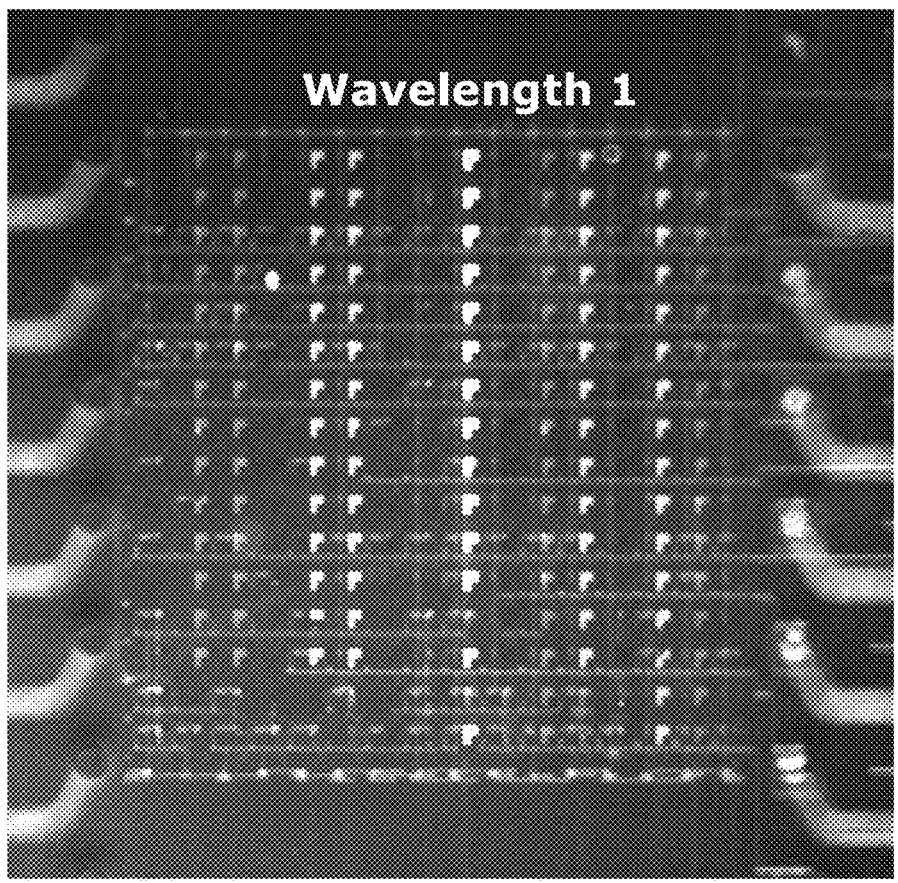
FIG. 3 is a photograph of fluorescent emission centered at a first wavelength produced by a reaction occurring in a number of reaction chambers present in a microfluidic device according to an embodiment of the present invention.

FIG. 3 is a photograph of fluorescent emission centered at a first wavelength produced by a reaction occurring in a number of reaction chambers present in a microfluidic device according to an embodiment of the present invention. As illustrated in FIG. 3, a number of reaction chambers produce emission at a first wavelength, "Wavelength 1." In the embodiment of the present invention illustrated in FIG. 3, a 10×16 array of reaction chambers are imaged. In some embodiments, the first wavelength is associated with a fluorophore as discussed previously. As will be evident to one of skill in the art, the intensity of emission at the first wavelength is a function of the chemical processes occurring in the reaction chambers. As illustrated, a two-dimensional array of 10×16 reaction chambers is imaged by the optical imaging system provided according to an embodiment of the present invention. As discussed previously, the reaction chambers are in fluidic isolation in some embodiments of the present invention. Moreover, according to alternative embodiments the reaction chambers are characterized by volumes on the scale of nanoliters and/or chamber densities on the order of hundreds of chambers per square centimeter.

Figure 4:
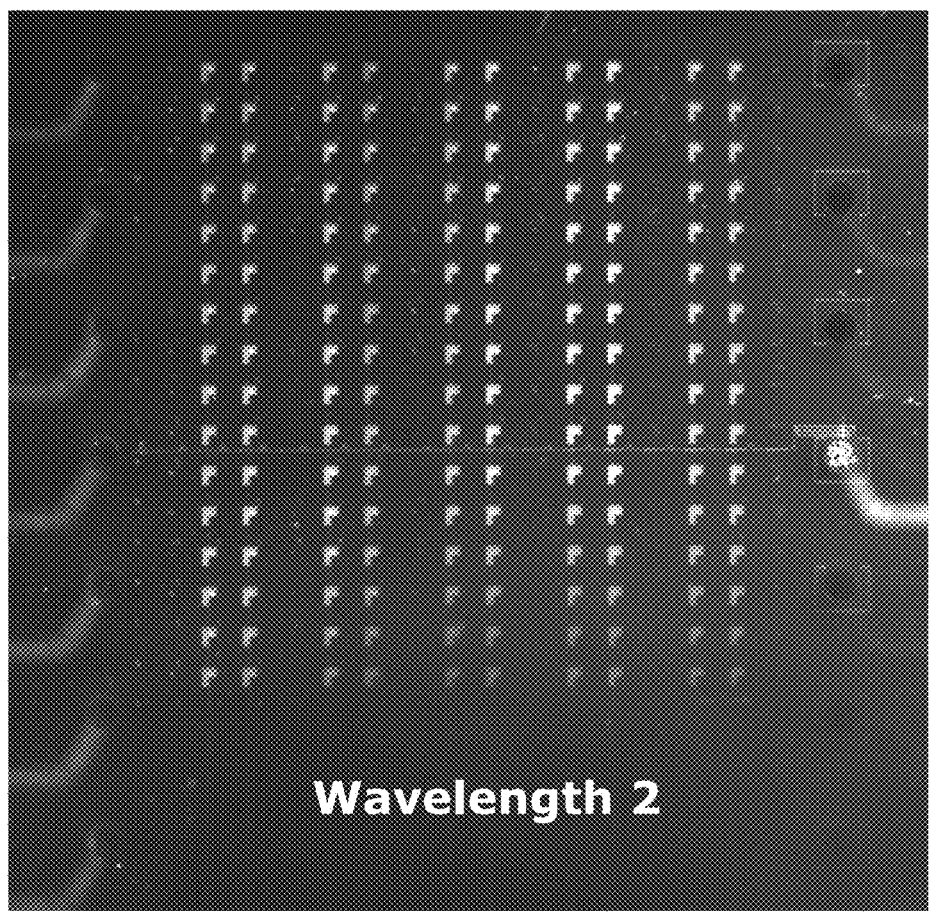
FIG. 4 is a photograph of fluorescent emission centered at a second wavelength produced by a reaction occurring in a number of reaction chambers present in a microfluidic device according to an embodiment of the present invention.

FIG. 4 is a photograph of fluorescent emission centered at a second wavelength produced by a reaction occurring in a number of reaction chambers present in a microfluidic device according to an embodiment of the present invention. As illustrated in FIG. 4, a number of the reaction chambers produce emission at a second wavelength, "Wavelength 2." Comparing FIGS. 3 and 4, some reaction chambers produce little to no light, while other reaction chambers produce light at either the first wavelength, the second wavelength, or both the first and second wavelength. Of course, collection and analysis of the fluorescence activity may yield insight into the nature of the chemical processes occurring in the reaction chambers.

Figure 5:
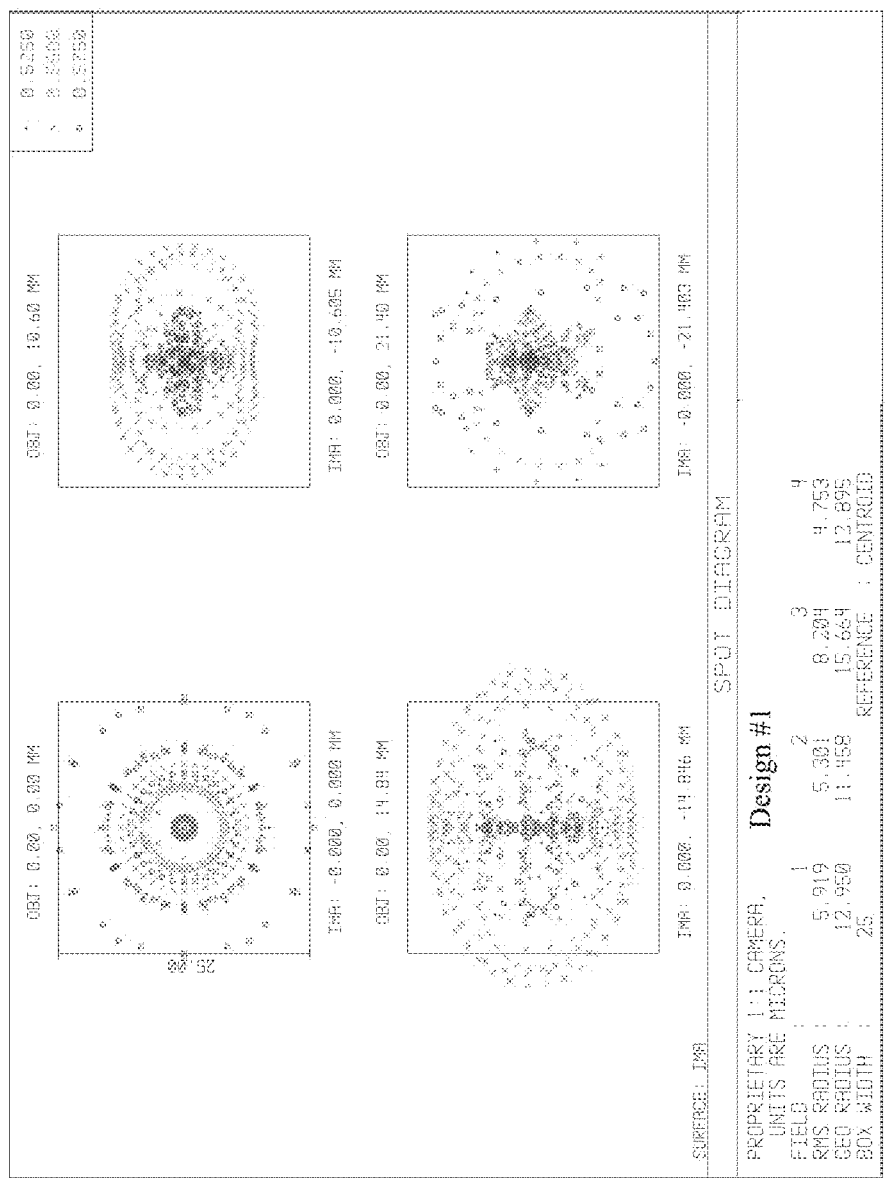
FIGS. 5-7 are spot diagrams for selected wavelengths produced using an embodiment of the present invention.
Figure 6:
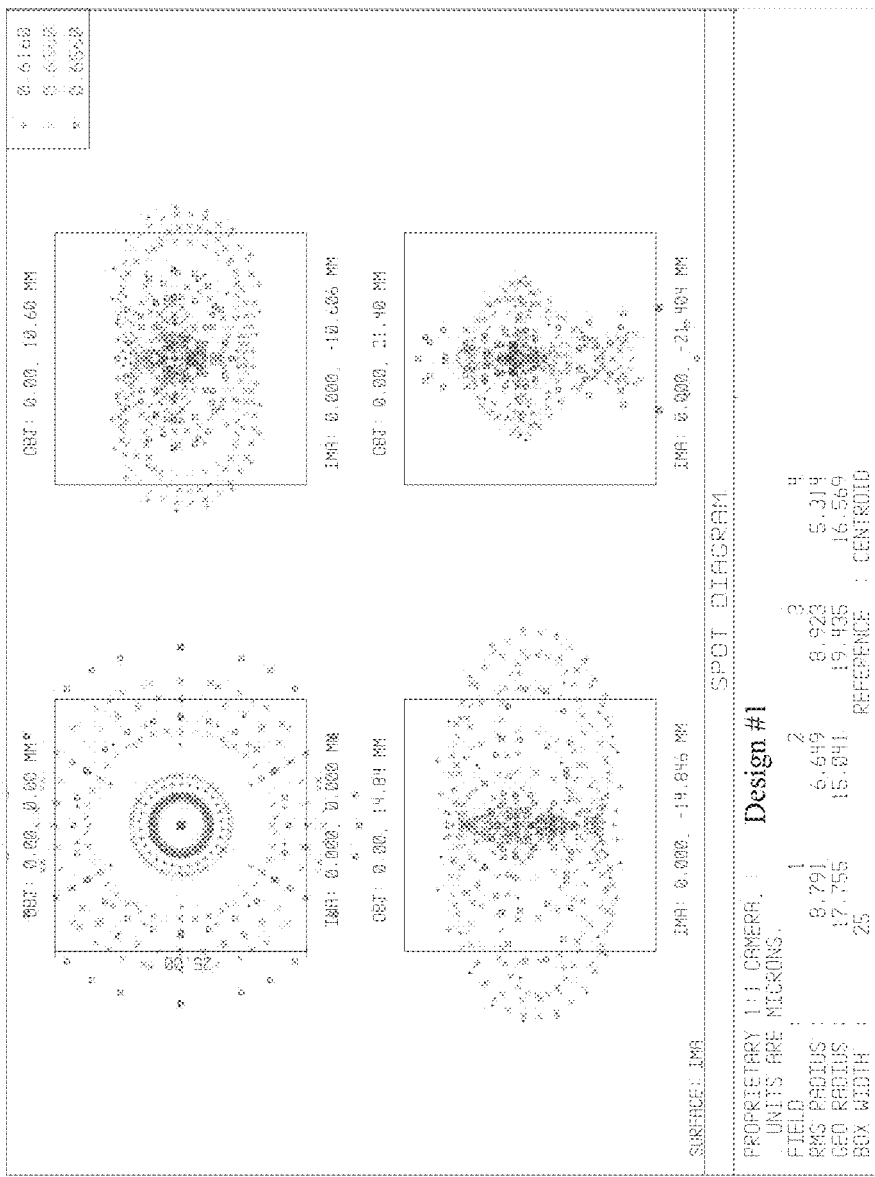
Figure 7:
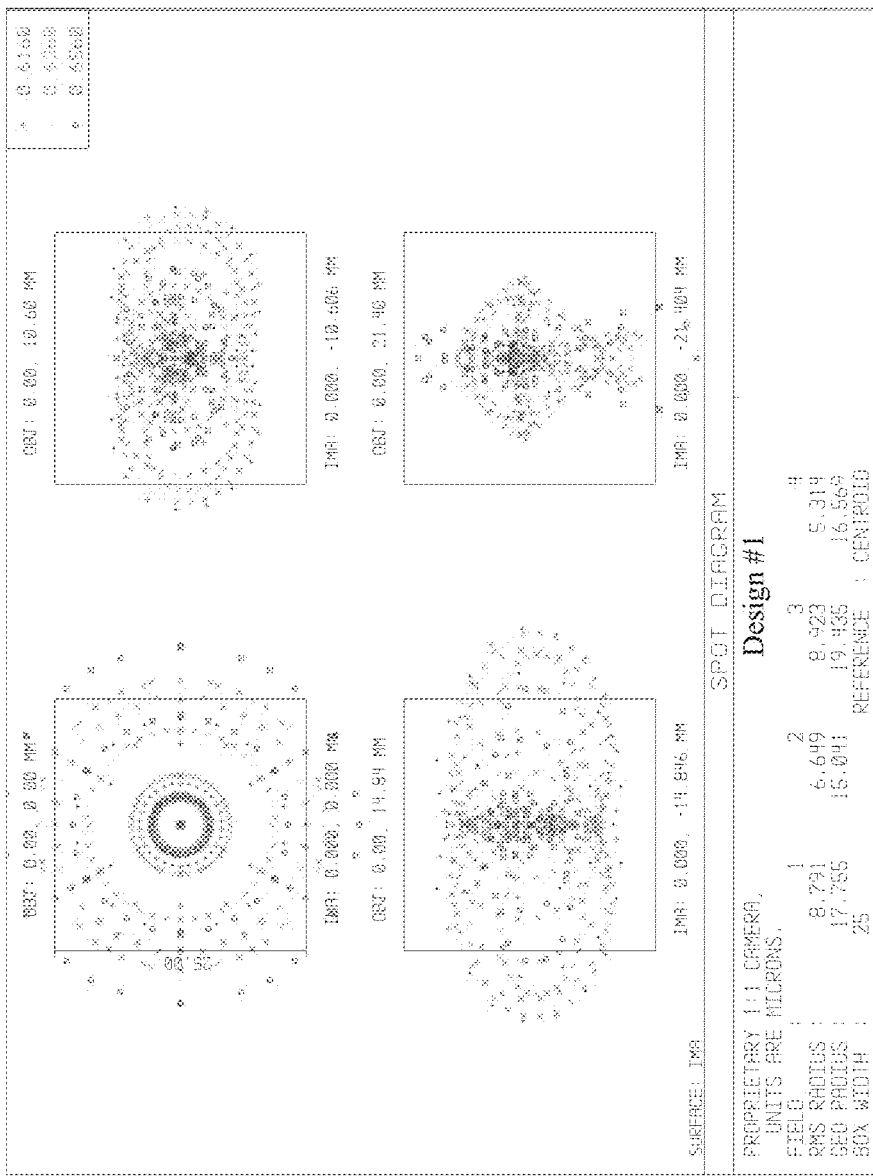

FIGS. 5-7 are spot diagrams for selected wavelengths produced using an embodiment of the present invention. Referring to the legends for the figures, the range of wavelengths illustrated in the figures are generally grouped into three wavelength bands: green, blue, and red wavelengths, respectively. Wavelengths of 525, 550, and 575 nm are illustrated in FIG. 5, generally associated with the green region of the optical spectrum. Wavelengths of 486, 501, and 516 nm are illustrated in FIG. 6, generally associated with the blue region of the optical spectrum. Wavelengths of 616, 636, and 656 nm are illustrated in FIG. 7, generally associated with the red region of the optical spectrum. FIG. 5 is calculated for the lens system illustrated in FIG. 2A, FIG. 6 is calculated for the lens system illustrated in FIG. 2B, and FIG. 7 is calculated for the lens system illustrated in FIG. 2C.

Figure 8:
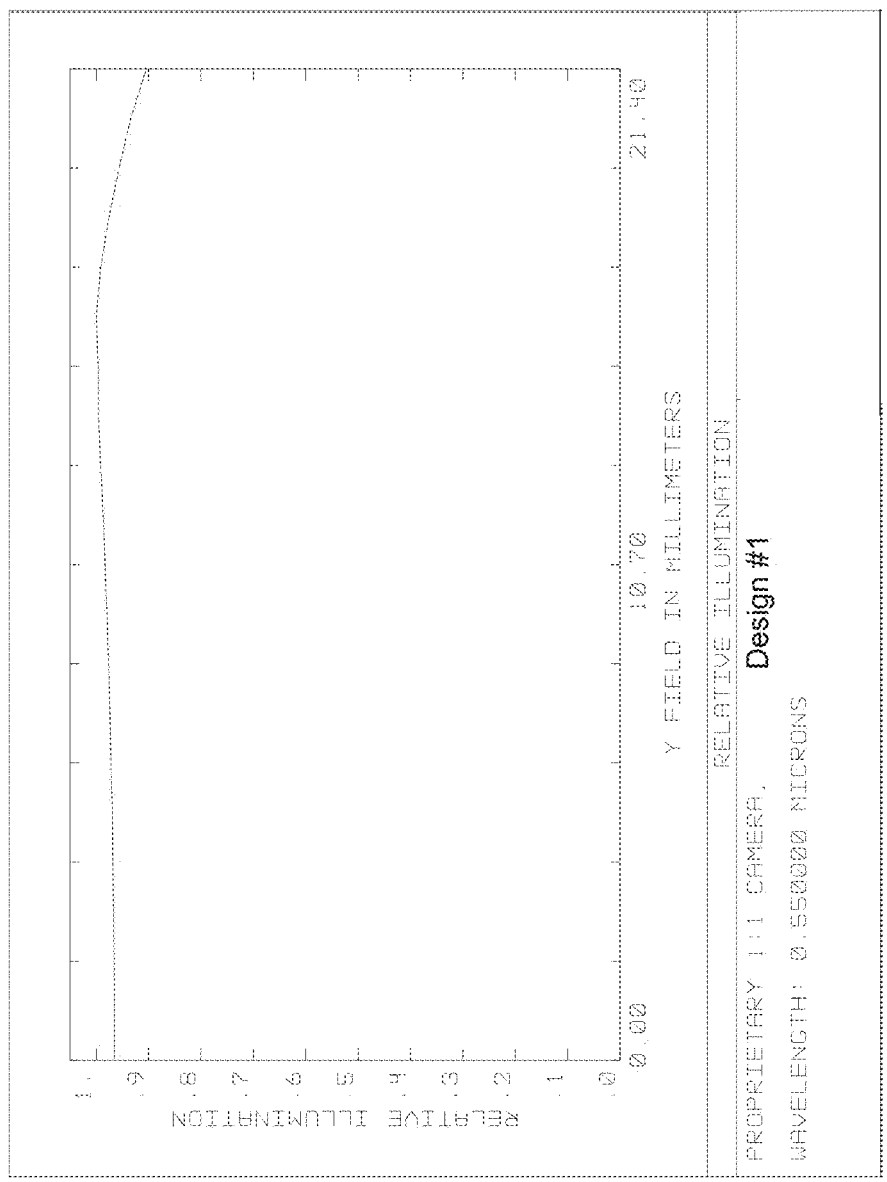
FIG. 8 is an illumination diagram illustrating relative uniformity as a function of position produced using an embodiment of the present invention.

FIG. 8 is an illumination diagram illustrating relative uniformity as a function of position produced using an embodiment of the present invention. In FIG. 8, the relative illumination is plotted as a function of the Y field in millimeters for the optical system illustrated in FIG. 2A. At a wavelength of 0.550 µm, the relative illumination uniformity over a distance of 21.4 mm is greater than 90%.

Figure 9:
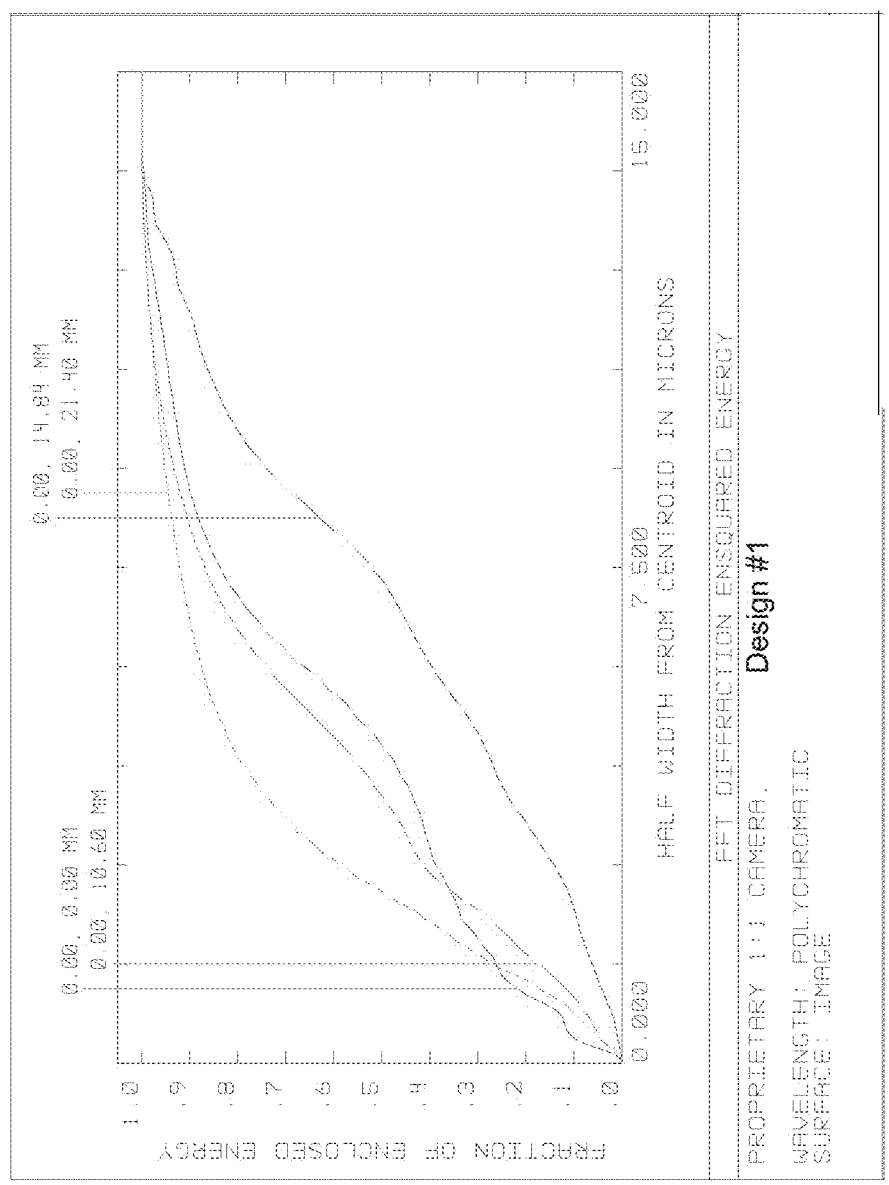
FIGS. 9-11 are ensquared energy diagrams for several embodiments according to the present invention.
Figure 10:
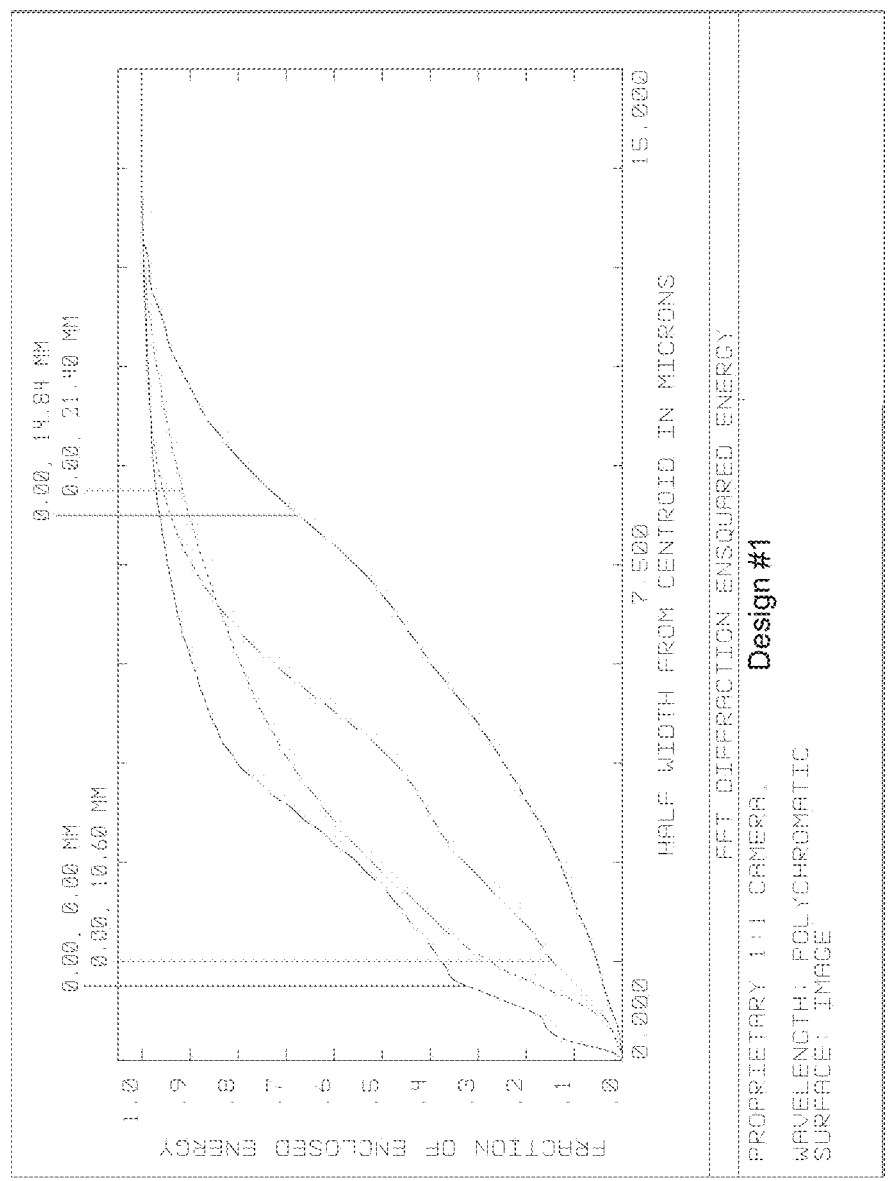
Figure 11:
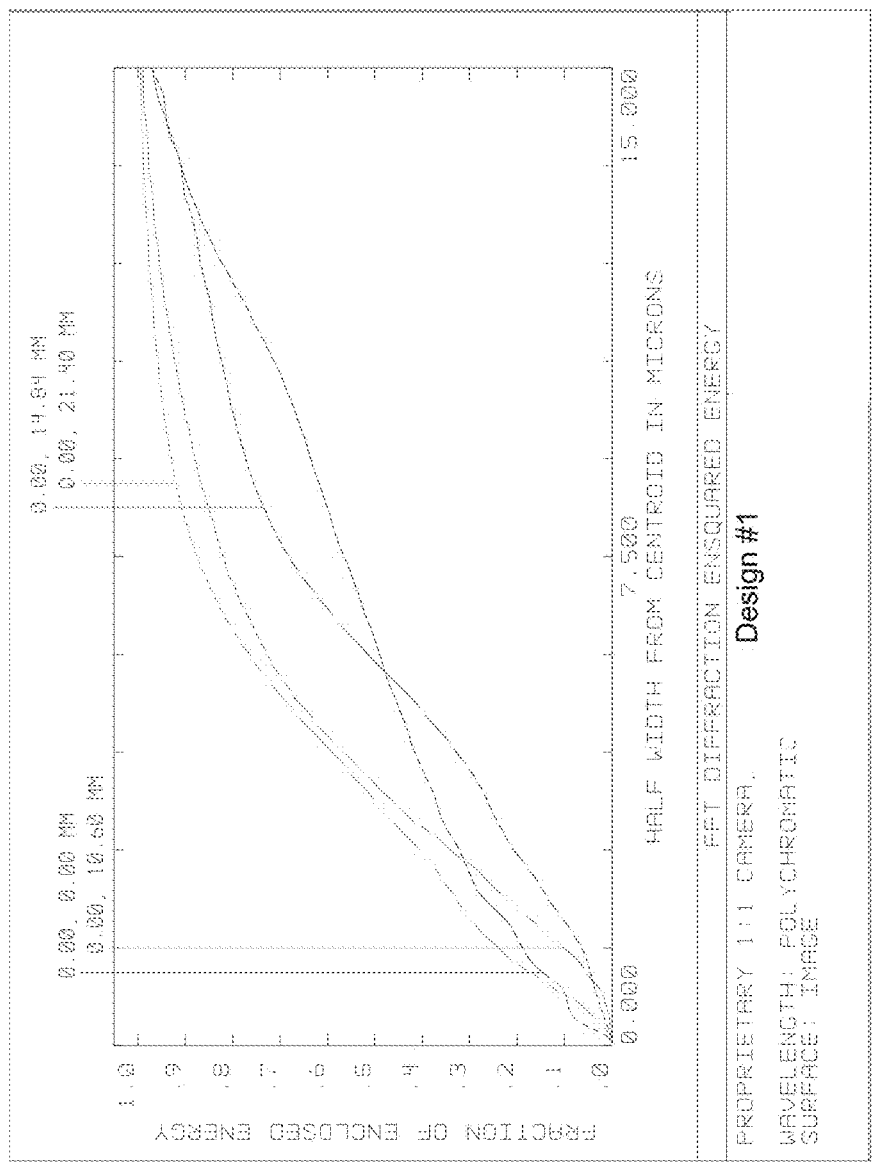

FIGS. 9-11 are ensquared energy diagrams for several embodiments according to the present invention. In some optical systems, a measure of the optical system performance is the ensquared energy percentage, which is the percent of total energy in a specified central region. Referring to FIG. 9, the fraction of the enclosed energy is plotted as a function of the half width from the centroid (in microns) for various positions using the lens system illustrated in FIG. 2A. As an example, for a position 14.8 mm from the center, about 50% of the energy is enclosed at about 7.5 µm from the centroid, whereas for a position 21.4 mm from the center, about 90% of the energy is enclosed at the same distance from the centroid. In FIGS. 9-11, diffraction is included and generally, the calculation is performed using fast Fourier transform (FFT) algorithms. FIGS. 10 and 11 are ensquared energy diagrams for the lens systems illustrated in FIGS. 2B and 2C, respectively. In these figures, as in FIG. 9, diffraction is included.

Figure 12:
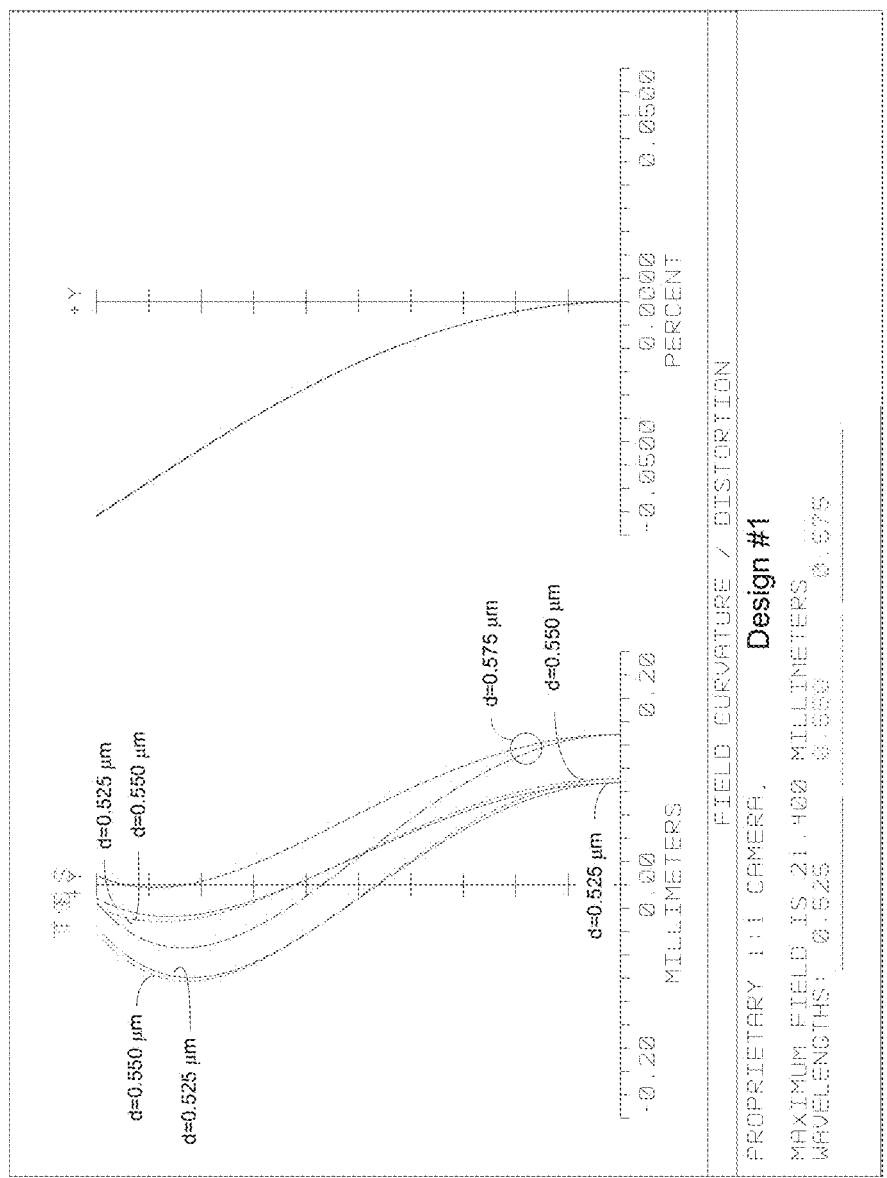
FIG. 12 is a diagram illustrating field curvature and distortion for an optical system provided according to an embodiment of the present invention.

FIG. 12 is a diagram illustrating field curvature and distortion for an optical system provided according to an embodiment of the present invention. Field curvature is illustrated for wavelengths of 0.525 µm, 0.550 µm, and 0.575 µm, as labeled in the figure. The distortion varies for the illustrated wavelengths, with negligible difference between the various wavelengths on the scale of 0.05% as illustrated.

Figure 13:
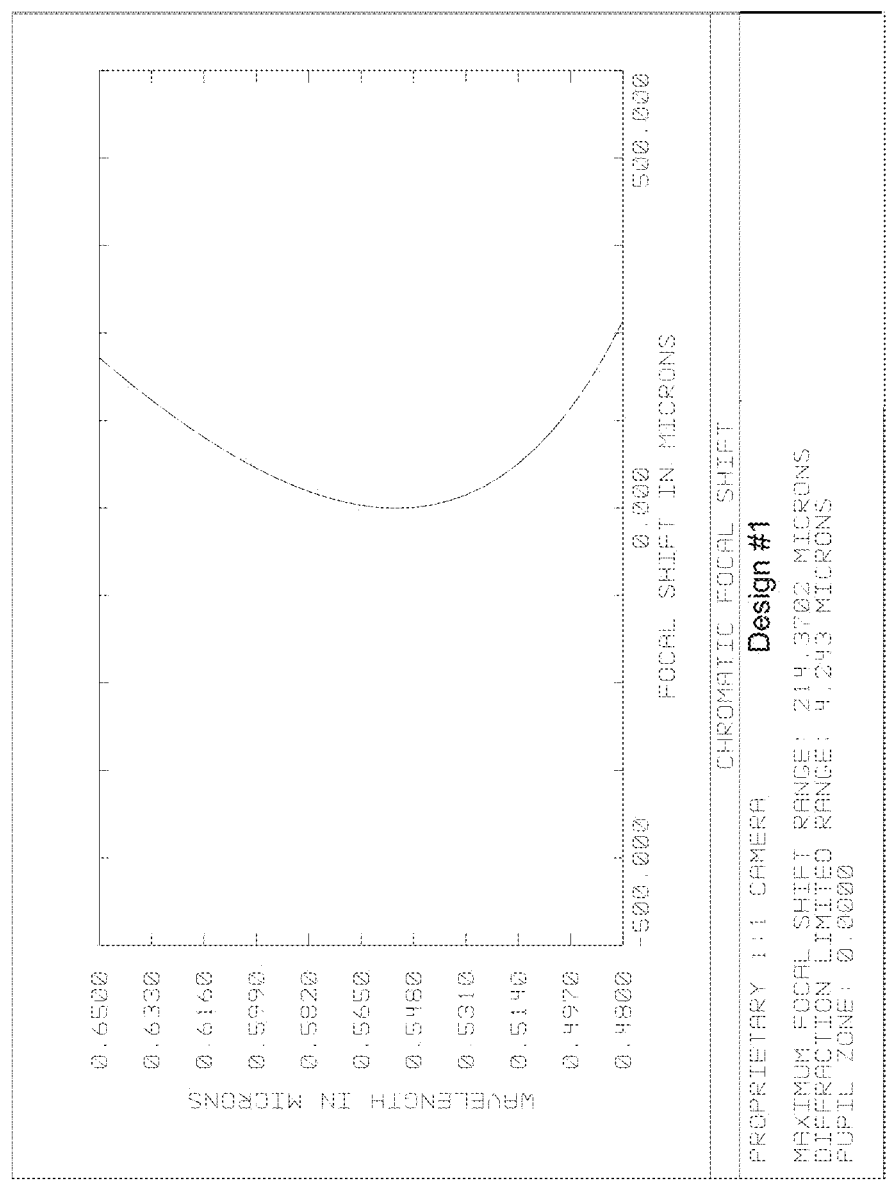
FIG. 13 is a diagram illustrating double wavelength versus focus produced by systems according to an embodiment of the present invention.

FIG. 13 is a diagram illustrating double wavelength versus focus produced by systems according to an embodiment of the present invention. In the figure, the chromatic focal shift is illustrated as a function of the wavelength in microns. The wavelength range plotted in FIG. 13 covers the wavelength range from 480 nm to 650 nm. As illustrated, the maximum focal shift range is 214.3702 µm and the diffraction limited range is 4.243 µm. Referring to FIG. 13, the colors focus over a 214 µm long span over the indicated range. Accordingly, an analysis of the system performance, generally includes consideration of the spot sizes at ±100 µm of defocus. In general, the size of the defocused spots will exceed that of the in-focus spots. According to embodiments of the present invention, axial chromatic aberration is corrected through the use of the buried doublets discussed above. In alternative embodiments, special glass types are utilized to achieve apochromatic performance (generally obtained at an increased cost compared to other glass types).

Figure 14:
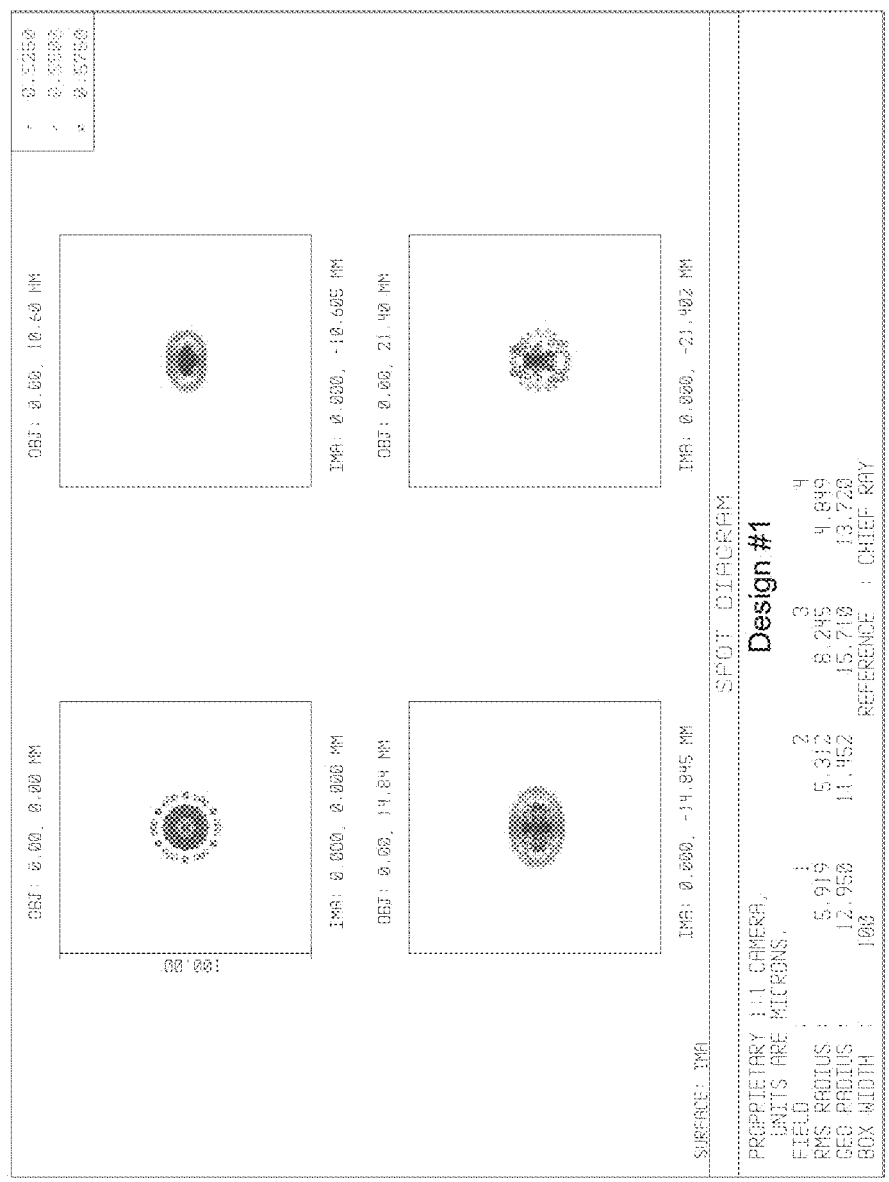
FIGS. 14-16 are spot diagrams for selected wavelengths produced using an embodiment of the present invention.
Figure 15:
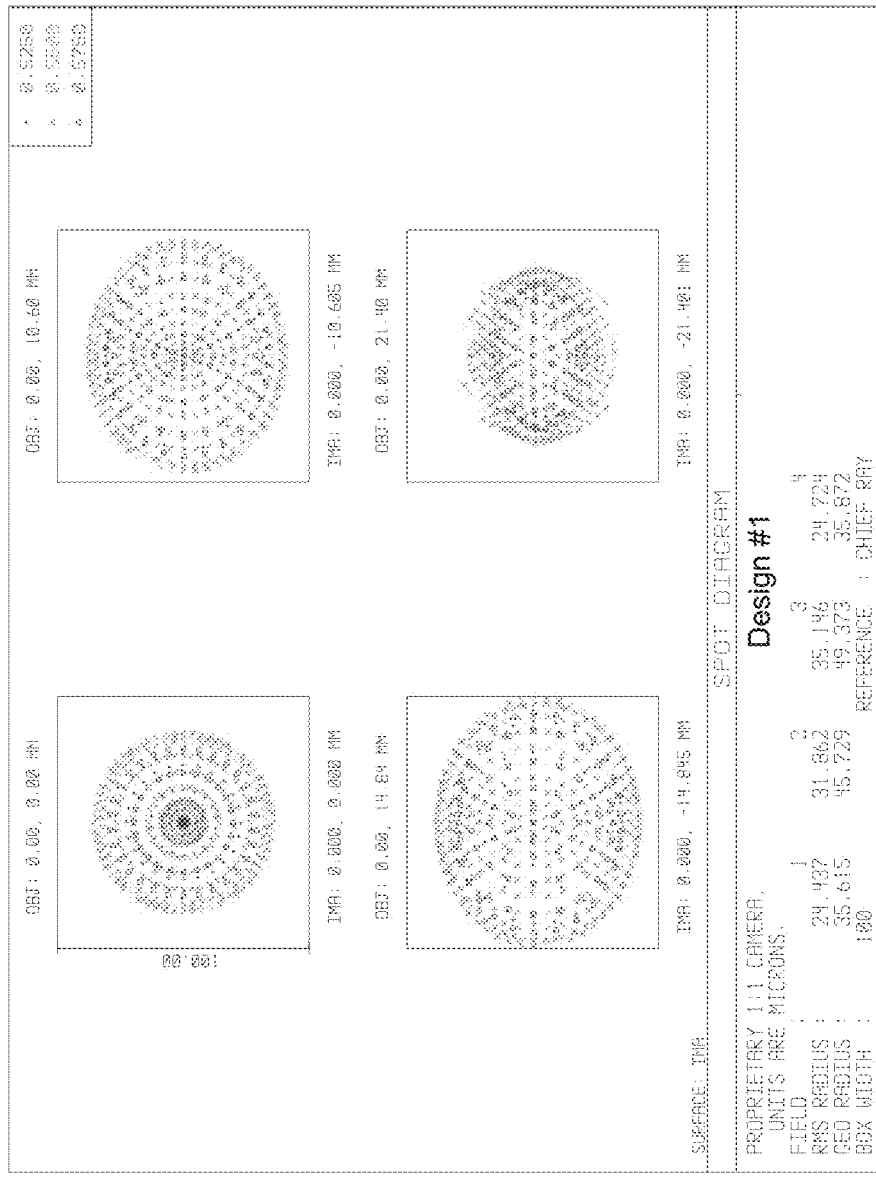
Figure 16:
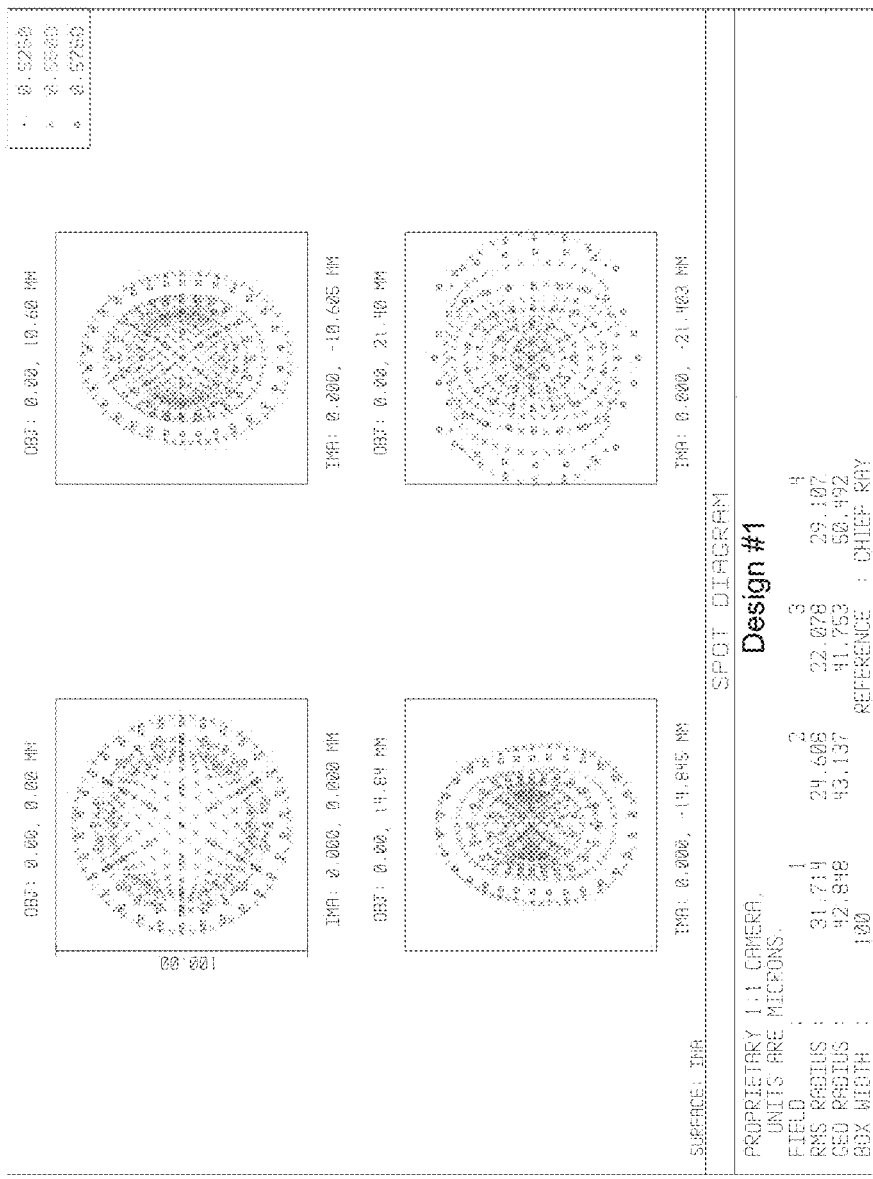

FIGS. 14-16 are spot diagrams for selected wavelengths produced using an embodiment of the present invention. As illustrated in the legend of FIG. 14, spot diagrams for wavelengths in the green region of the optical spectrum (525, 550, and 575 nm) are provided with the system at an optimal focus position. To generate the spot diagrams illustrated in FIGS. 14-16, the lens system illustrated in FIG. 2A was utilized. FIGS. 15 and 16 are spot diagrams calculated at +100 µm of defocus and −100 µm of defocus, respectively. In FIGS. 15 and 16, the same wavelengths in the green region of the optical spectrum are considered.

Figure 17:
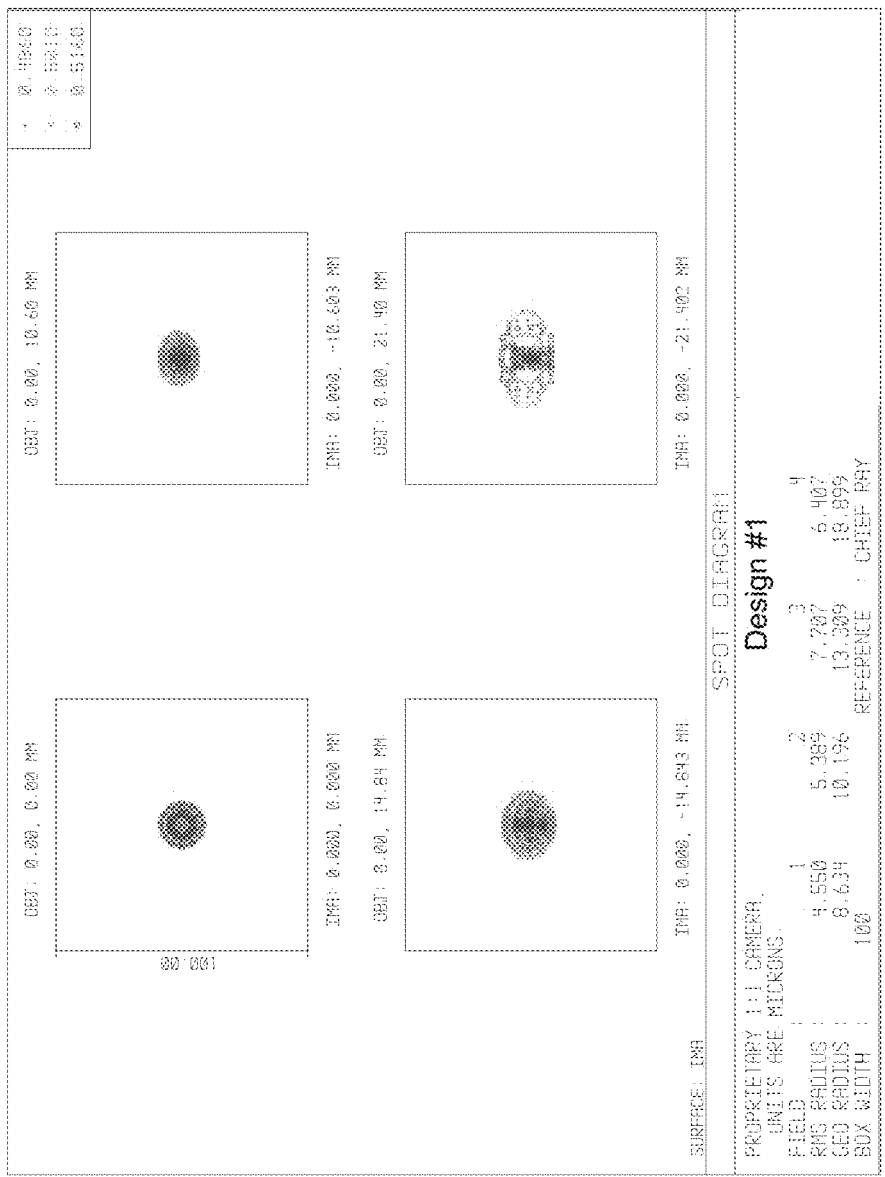
FIGS. 17-19 are spot diagrams for selected wavelengths produced using an embodiment of the present invention.
Figure 18:
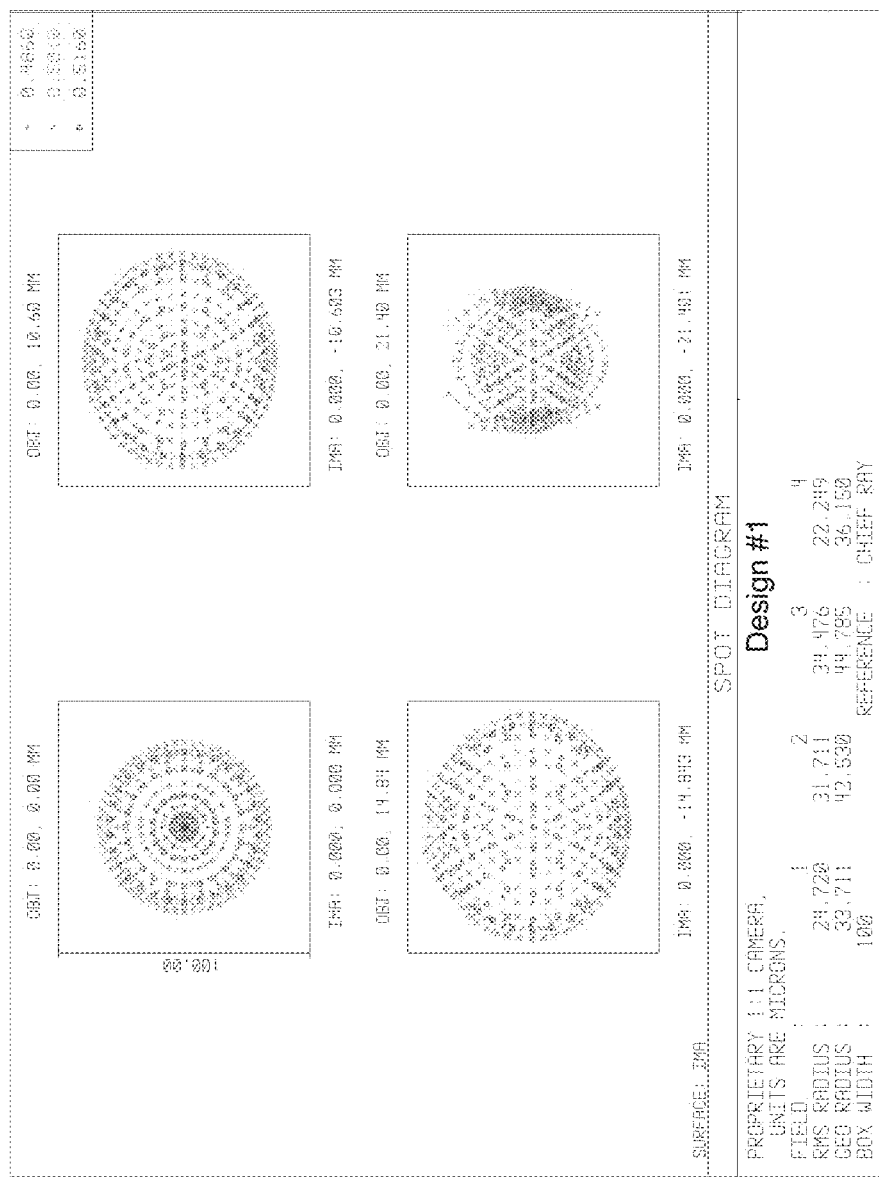
Figure 19:
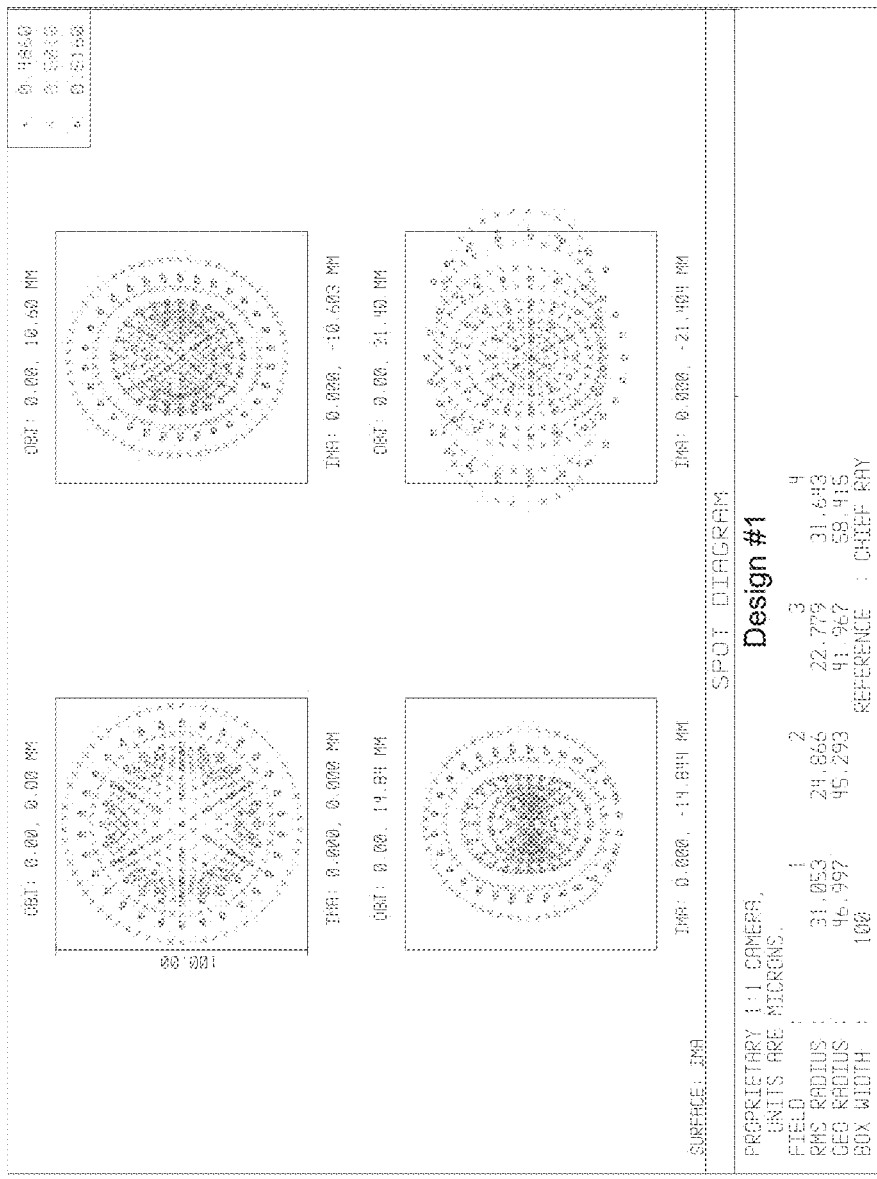

FIGS. 17-19 are spot diagrams for selected wavelengths produced using an embodiment of the present invention. As illustrated in the legend of FIG. 17, spot diagrams for wavelengths in the blue region of the optical spectrum (486, 501, and 516 nm) are provided with the system at an optimal focus position. To generate the spot diagrams illustrated in FIGS. 17-19, the lens system illustrated in FIG. 2B was utilized. FIGS. 18 and 19 are spot diagrams calculated at +100 µm of defocus and −100 µm of defocus, respectively. In FIGS. 18 and 19, the same wavelengths in the blue region of the optical spectrum are considered. As illustrated in FIG. 19, field 4 includes rays at 501 nm extending outside the 100 µm box shown in the figure.

Figure 20:
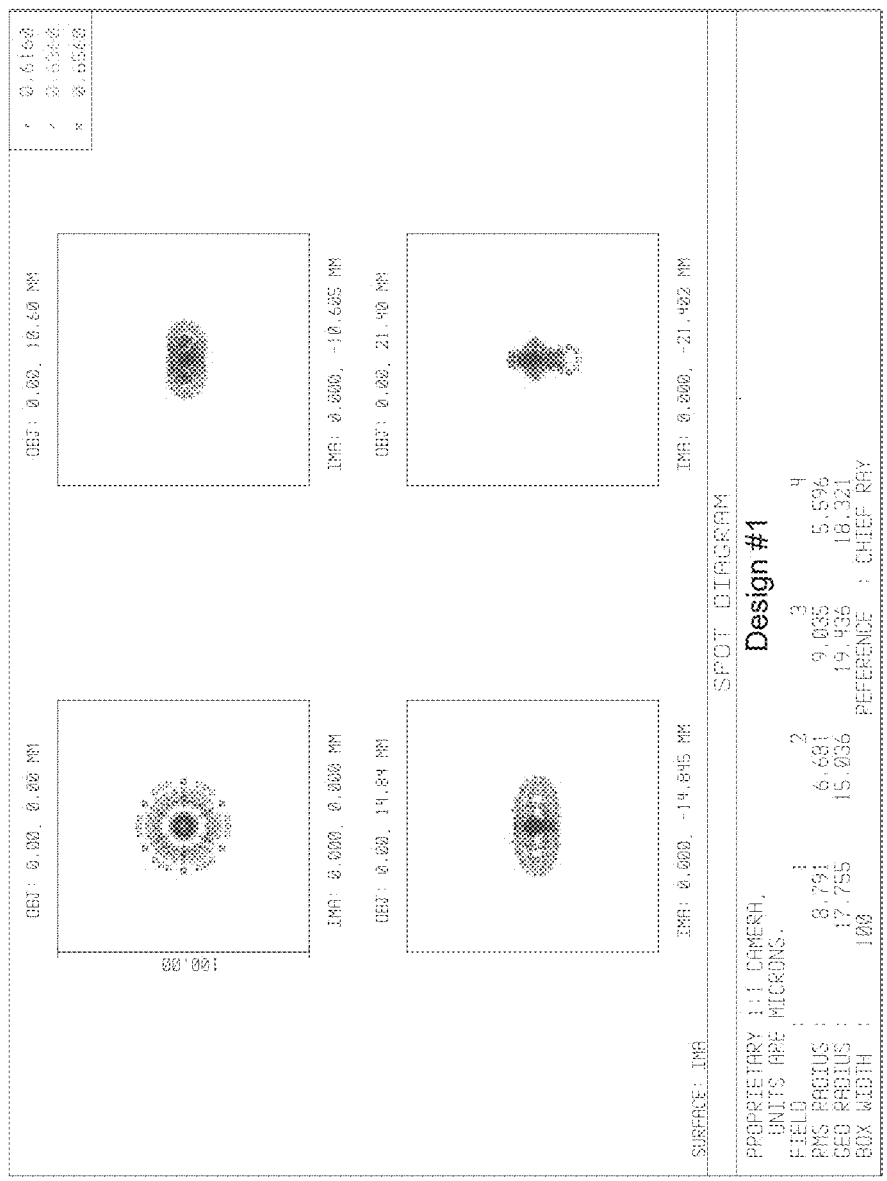
FIGS. 20-22 are spot diagrams for selected wavelengths produced using an embodiment of the present invention.
Figure 21:
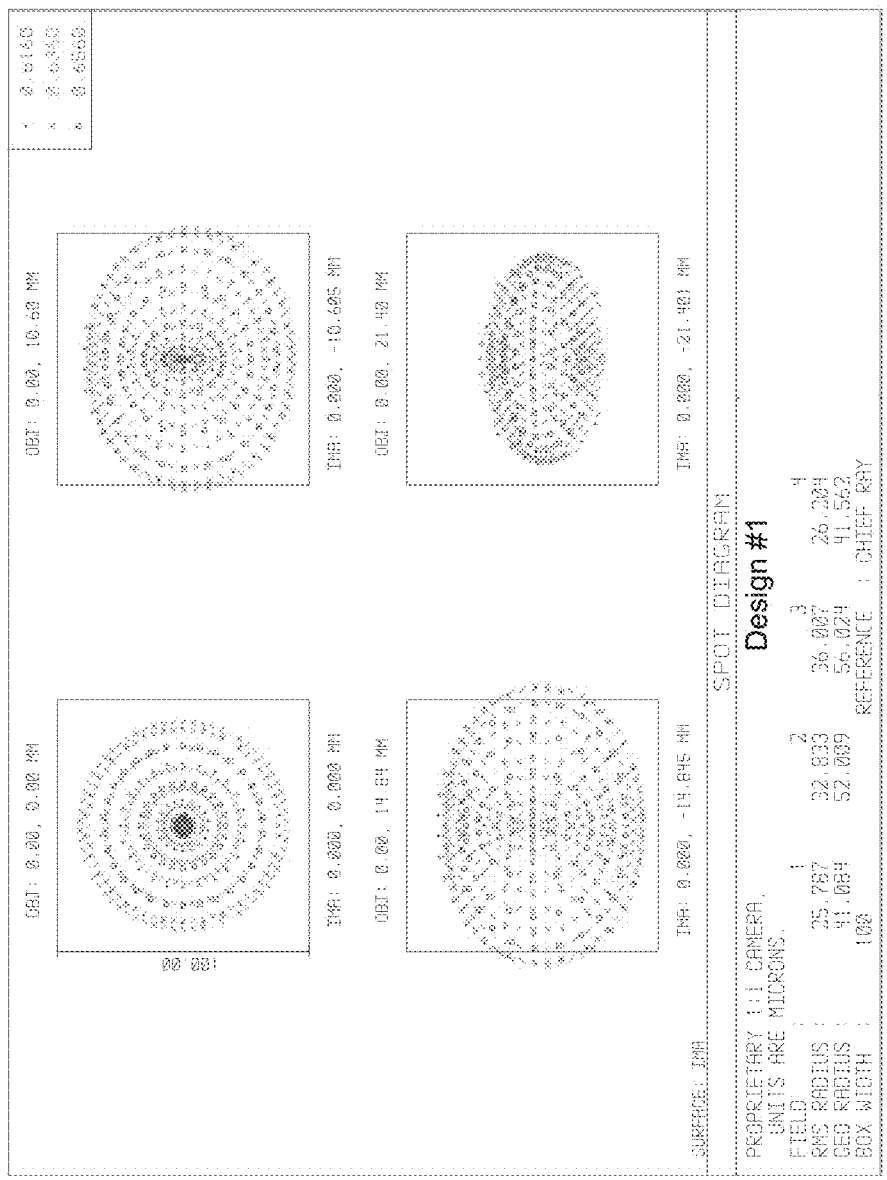
Figure 22:
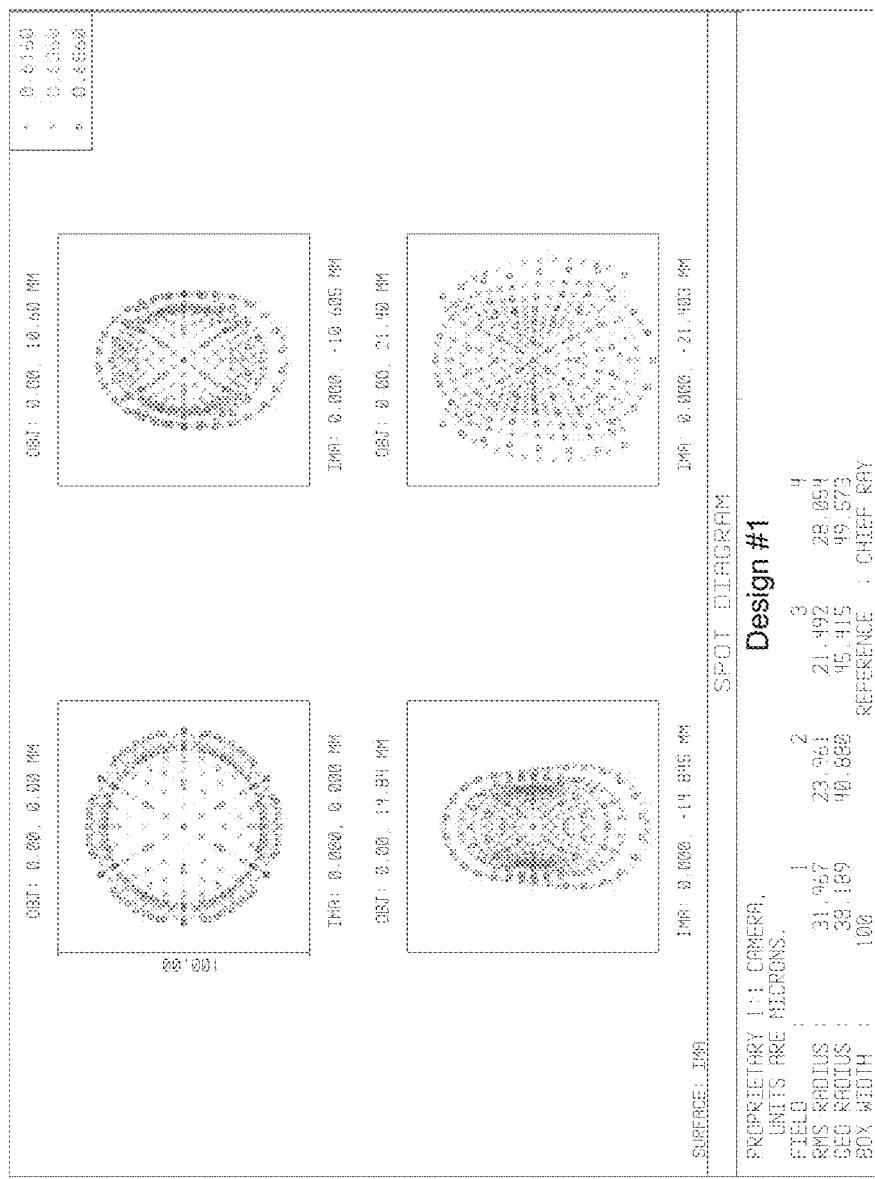

FIGS. 20-22 are spot diagrams for selected wavelengths produced using an embodiment of the present invention. As illustrated in the legend of FIG. 20, spot diagrams for wavelengths in the red region of the optical spectrum (616, 636, and 656 nm) are provided with the system at an optimal focus position. To generate the spot diagrams illustrated in FIGS. 20-22, the lens system illustrated in FIG. 2C was utilized. FIGS. 21 and 22 are spot diagrams calculated at +100 µm of defocus and −100 µm of defocus, respectively. In FIGS. 21 and 22, the same wavelengths in the red region of the optical spectrum are considered.

In an alternative embodiment according to the present invention, another 1:1 optical relay imaging system is provided including modifications to the optical elements illustrated in FIGS. 2A to 2C. Although the general optical train is preserved, characteristics of the particular elements, including the filter/zero-power doublet combination are modified. In this alternative embodiment, a working distance of greater than 35 mm, for example, 46.12 mm is provided. Moreover, an RMS spot diameter averaging 11.28 µm with a maximum value of 14.73 µm is provided, the overall length of the optical imaging system is 542.2 mm, with a maximum filter AOI of 12.59 degrees, and a maximum beam diameter at the filter of 76 mm.

Figure 23:
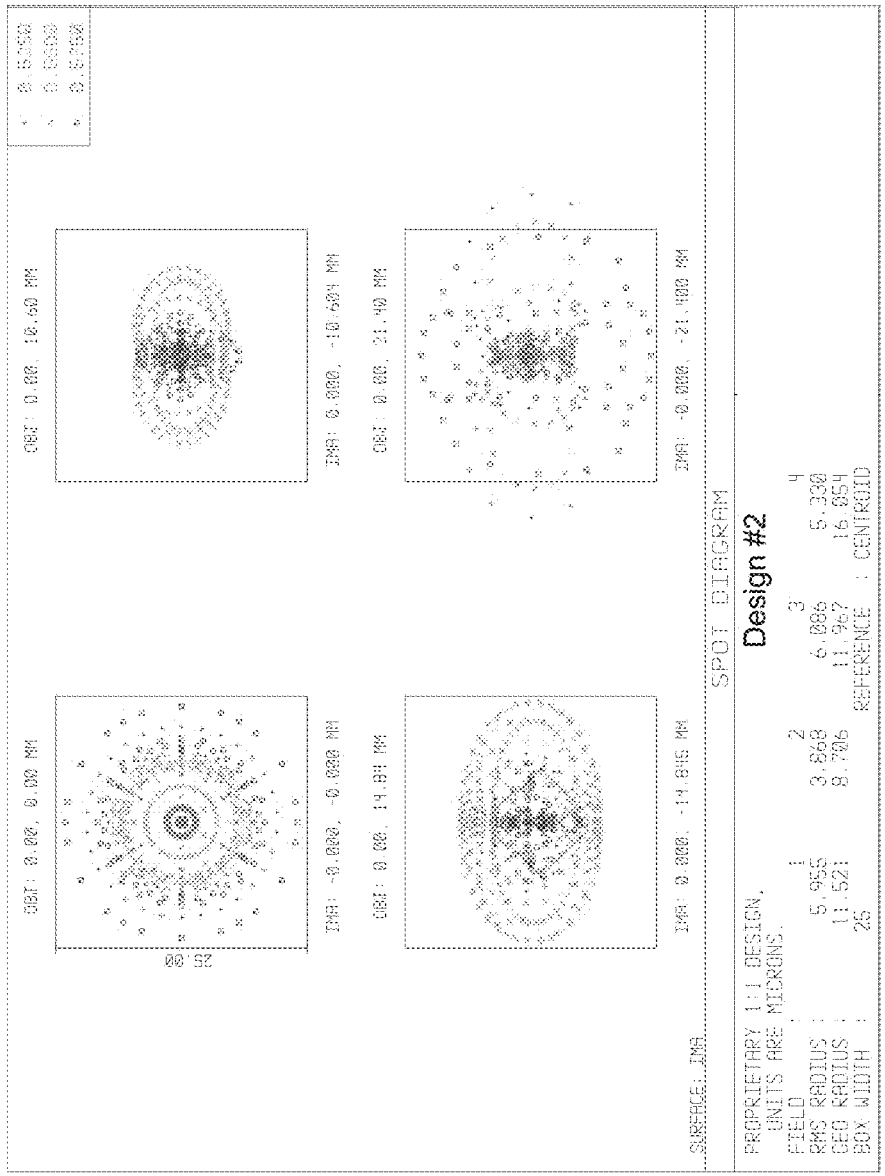
FIGS. 23-25 are spot diagrams for selected wavelengths produced using an embodiment of the present invention.
Figure 24:
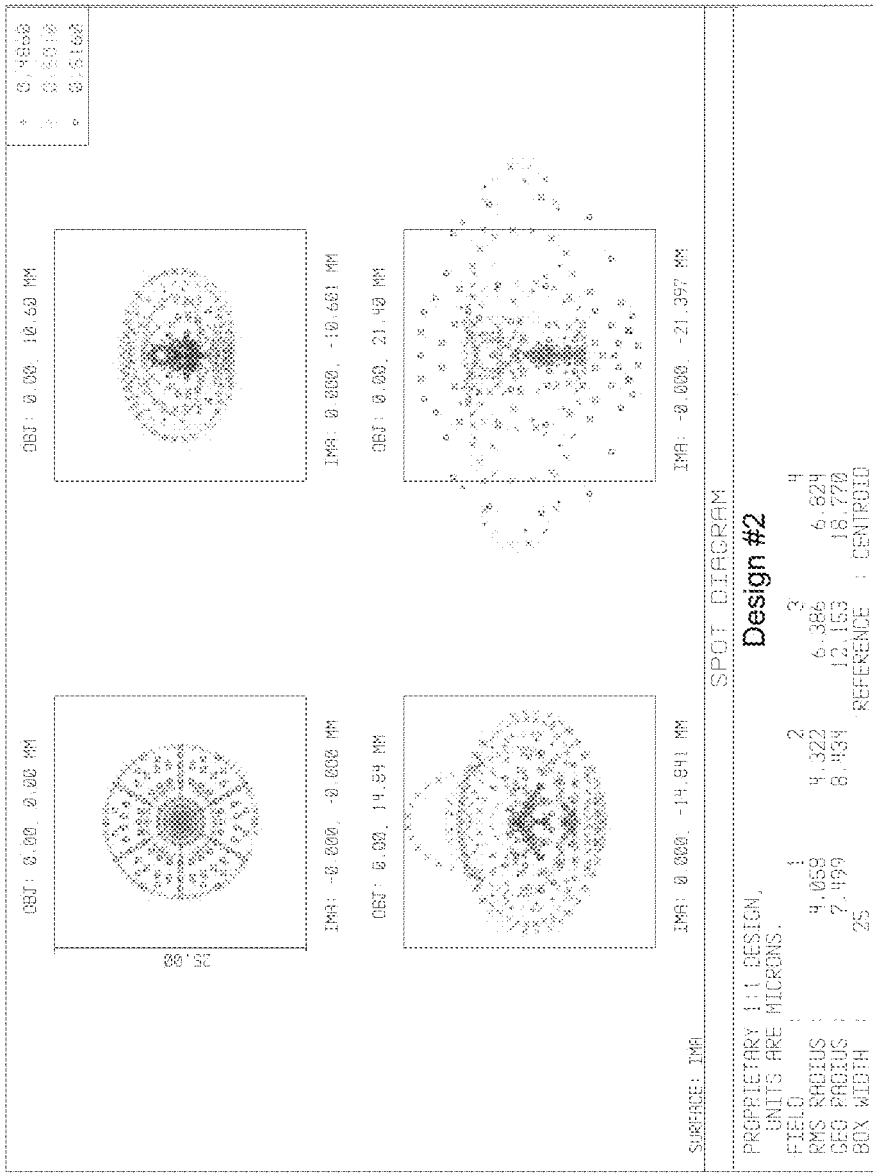
Figure 25:
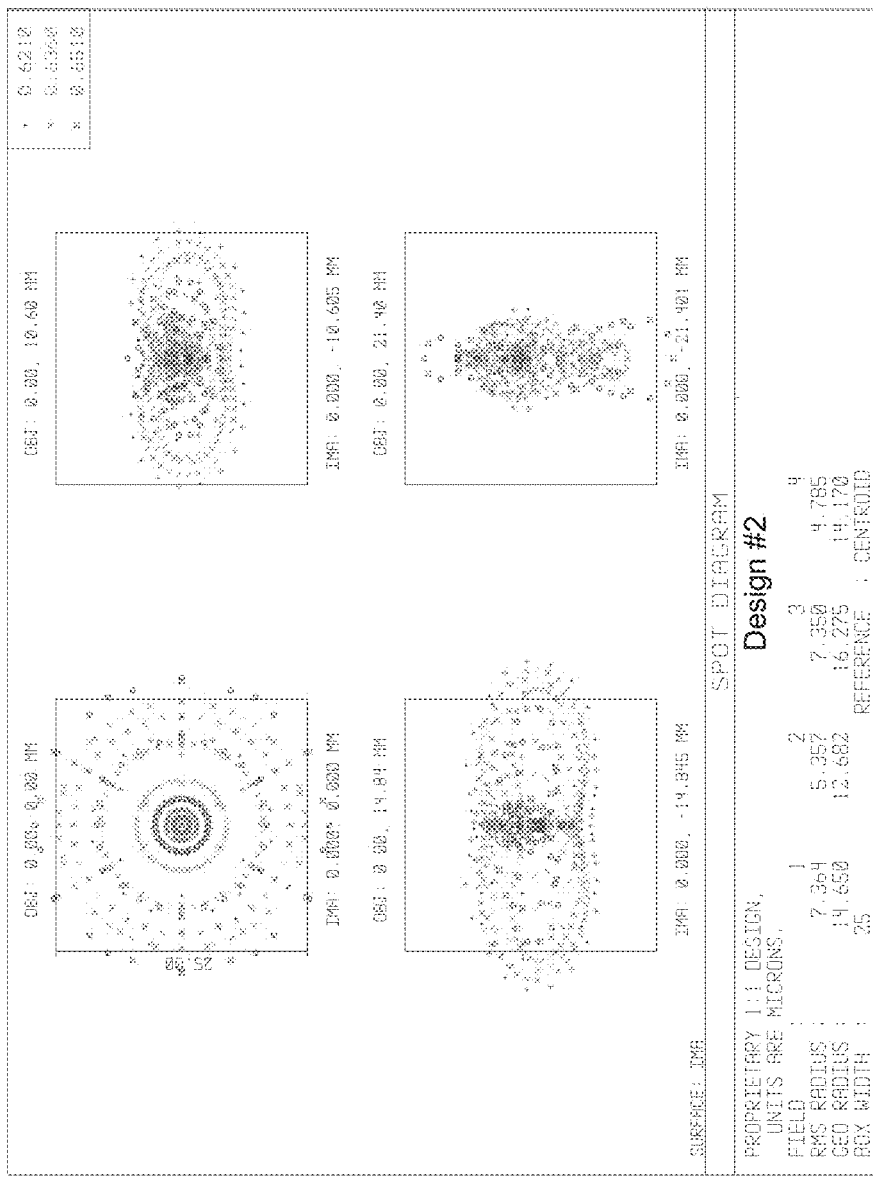

FIGS. 23-25 are spot diagrams for selected wavelengths produced using an alternative embodiment of the present invention. Referring to the legends for the figures, the range of wavelengths illustrated in the figures are generally grouped into three wavelength bands: green, blue, and red wavelengths, respectively. Wavelengths of 525, 550, and 575 nm are illustrated in FIG. 23, generally associated with the green region of the optical spectrum. Wavelengths of 486, 501, and 516 nm are illustrated in FIG. 24, generally associated with the blue region of the optical spectrum. Wavelengths of 621, 636, and 651 nm are illustrated in FIG. 25, generally associated with the red region of the optical spectrum. FIG. 23 is calculated for a lens system based on that illustrated in FIG. 2A, FIG. 24 is calculated for a lens system based on that illustrated in FIG. 2B, and FIG. 25 is calculated for a lens system based on that illustrated in FIG. 2C.

Figure 26:
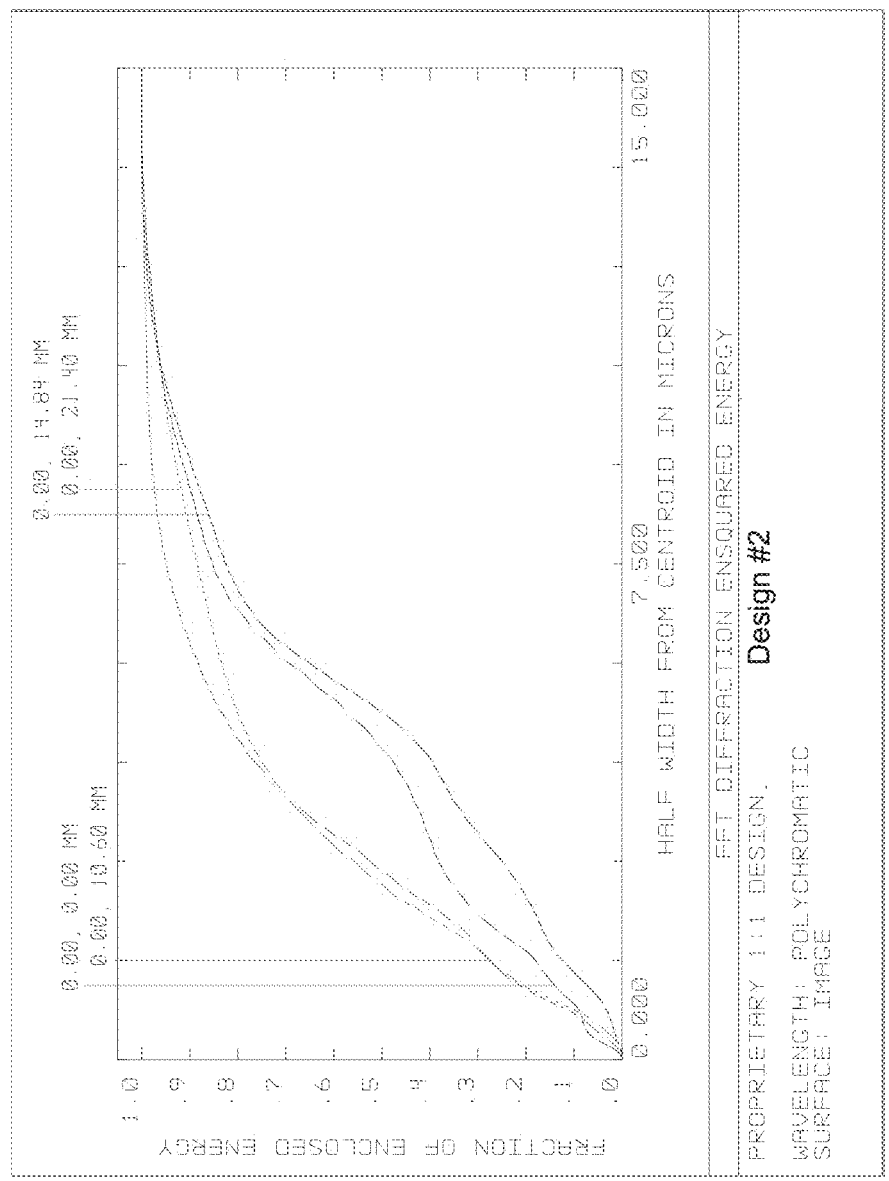
FIGS. 26-28 are ensquared energy diagrams for several embodiments according to the present invention.
Figure 27:
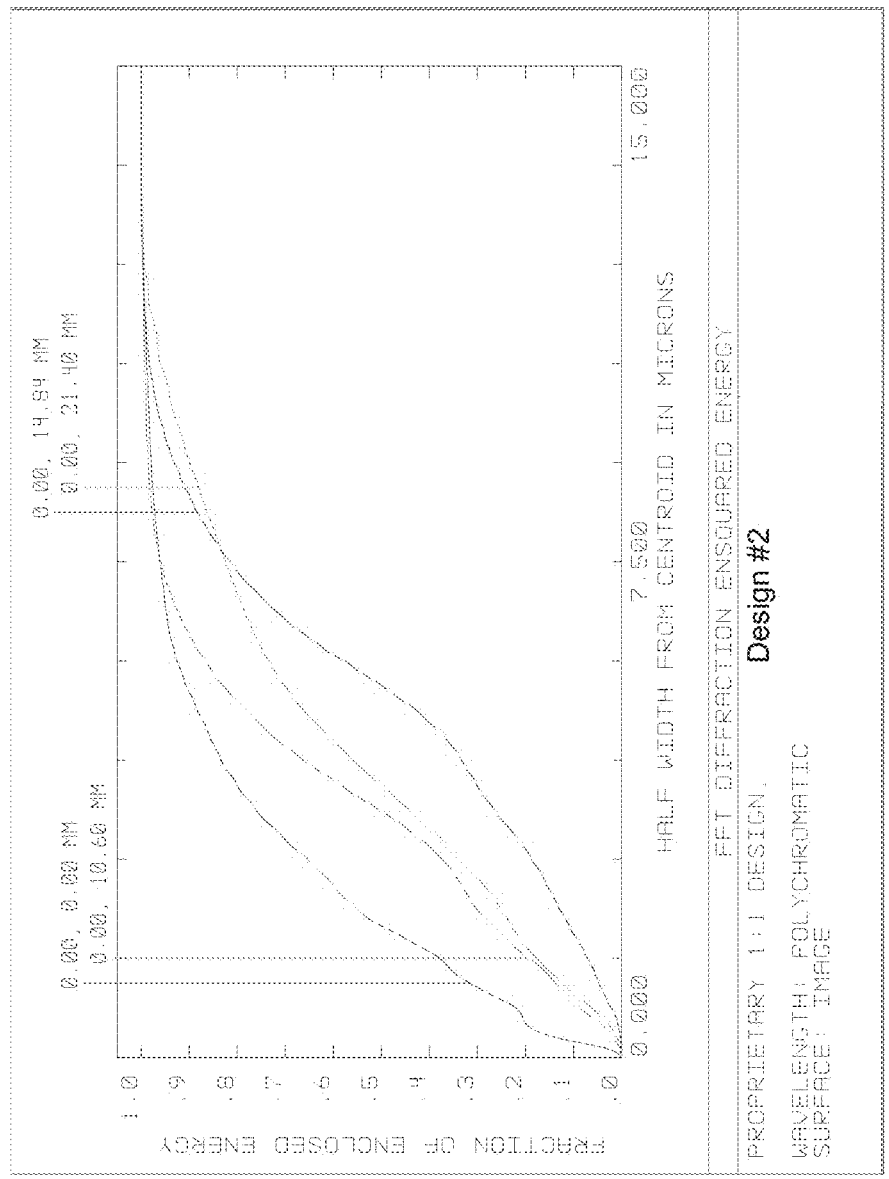
Figure 28:
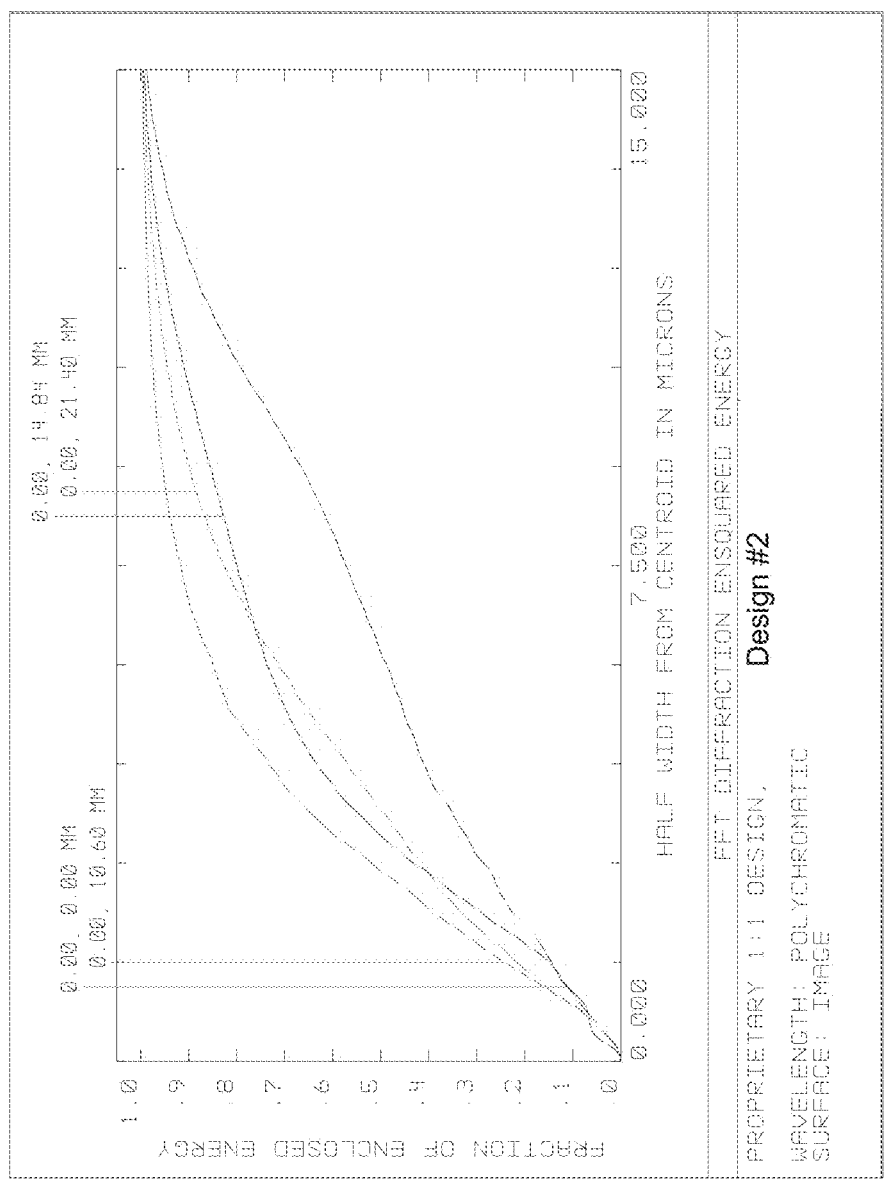

FIGS. 26-28 are ensquared energy diagrams for several embodiments according to the present invention. Referring to FIG. 26, the fraction of the enclosed energy is plotted as a function of the half width from the centroid (in microns) for various positions using the lens system illustrated in FIG. 2A. As an example, for a position 14.8 mm from the center, about 80% of the energy enclosed at about 7.5 µm from the centroid, whereas for a position 21.4 mm from the center, about 90% of the energy enclosed at the same distance from the centroid. In FIGS. 26-28, diffraction is included and generally, the calculation is performed using fast Fourier transform (FFT) algorithms. FIGS. 27 and 28 are ensquared energy diagrams for the lens systems illustrated in FIGS. 2B and 2C, respectively. In these figures, as in FIG. 26, diffraction is included.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of monitoring DNA sequencing, the method comprising:
    providing a fluidic device comprising:
        a plurality of reaction sites having a reaction site density of greater than or equal to 250,000 reaction sites per square centimeter;
        at least one sample introduced to the plurality of reaction sites; and
        at least one amplification reagent introduced to the plurality of reaction sites;
    amplifying the at least one sample at the plurality of reaction sites;
    sequencing the at least one amplified sample at the plurality of reaction sites at a predetermined temperature;
    illuminating the fluidic device with electromagnetic radiation with an illumination system;
    transmitting the electromagnetic radiation along an optical path coupled to the device and an optical lens system;
    reducing chromatic aberration of light with the optical lens system along the optical path;
    capturing an image of a determined number of reaction sites simultaneously; and
    collecting multiple images of the fluidic device, wherein collecting multiple images comprises:
        collecting at least a first image at a first wavelength; and
        collecting at least a second image at a second wavelength different from the first wavelength.

2. The method of claim 1, wherein the plurality of reaction sites has a reaction site density of greater than or equal to 1,000,000 reaction sites per square centimeter.

3. The method of claim 1, wherein reducing chromatic aberration is carried out by at least one zero-power doublet.

4. The method of claim 1, wherein the electromagnetic radiation emitted from the plurality of processing sites is transmitted through a first multi-element optical train and a second multi-element optical train of the optical lens system.

5. The method of claim 1, wherein collecting multiple images further comprises capturing the multiple images over a time frame from about 1 millisecond to about 1 minute.

6. The method of claim 1, wherein collecting multiple images is conducted while maintaining the plurality of reaction sites at the predetermined temperature.

7. The method of claim 1, wherein the optical lens system comprises a wheel or filter holder, wherein the filter wheel or holder is positionable to at least two operating positions.

8. The method of claim 1, wherein amplifying the at least one sample comprises:
    extending a first polynucleotide sample with a first primer to form a hybrid polynucleotide;
    degrading the hybrid polynucleotide to form a second polynucleotide sample; and
    extending the second polynucleotide sample with a second primer to form a double-stranded polynucleotide sample.

9. The method of claim 8, wherein amplifying the at least one sample further comprises:
    transcribing the double-stranded polynucleotide sample; and
    generating multiple anti-sense product of the first polynucleotide sample.

10. The method of claim 1, wherein the electromagnetic radiation transmitted along the optical path comprises electromagnetic radiation emitted from the plurality of processing sites.

11. A system for monitoring DNA sequencing, the system comprising:
    a fluidic device having a plurality of reaction sites with a reaction site density of greater than or equal to 250,000 reaction sites per square centimeter and configured to receive at least one sample and at least one amplification reagent, wherein the reaction sites of the fluidic device are maintained at predetermined temperatures during amplification and sequencing of the at least one sample at the plurality of reaction sites;
    a thermal controller coupled to the fluidic device, the thermal controller configured to provide temperature control to the plurality of reaction sites;
    an illumination system coupled to the fluidic device and configured to illuminate the fluidic device with electromagnetic radiation;
    an optical lens system coupled to an optical path and configured to transmit the electromagnetic radiation along the optical path, wherein the optical lens system is configured to reduce chromatic aberration of light along the optical path; and
    a detector configured to capture multiple images of the fluidic device, wherein each image simultaneously encompasses a determined number of reaction sites, wherein at least a first image is captured at a first illumination wavelength and at least a second image is captured at a second illumination wavelength different from the first illumination wavelength.

12. The system of claim 11, wherein the plurality of reaction sites has a reaction site density of greater than or equal to 1,000,000 reaction sites per square centimeter.

13. The system of claim 11, wherein the optical lens system comprises at least one zero-power doublet.

14. The system of claim 11, wherein the detector is configured to collect multiple images over a time frame of 1 millisecond to 1 minute.

15. The system of claim 11, wherein the optical lens system comprises a wheel or filter holder, wherein the filter wheel or holder is positionable to at least two operating positions.

16. The system of claim 11, wherein the optical lens system comprises a first multi-element optical train coupled to a first portion of the optical path and a second multi-element optical train coupled to a second portion of the optical path.

17. The system of claim 11, wherein the fluidic device is configured to amplify nucleic acids to produce an amplified product.

18. The system of claim 17, further comprising sequencing of the amplified product.

19. The system of claim 11, wherein the system is configured to capture the first and second images while maintaining the fluidic device at a predetermined temperature.

20. The system of claim 11, wherein the electromagnetic radiation transmitted along the optical path comprises electromagnetic radiation emitted from the plurality of processing sites.

* * * * *